US009267948B2

(12) United States Patent
O'Neill et al.

(10) Patent No.: US 9,267,948 B2
(45) Date of Patent: Feb. 23, 2016

(54) COMPOSITIONS AND METHODS FOR CANCER MANAGEMENT USING ANTIBODIES BINDING TO NUCLEOTIDE SALVAGE PATHWAY ENZYMES AND COMPLEXES THEREOF

(75) Inventors: Kim Leslie O'Neill, Provo, UT (US); Robert Alan Whitehurst, Buena Vista, VA (US); Jaden Duss Evans, Centerville, UT (US); Daniel Williar Sharp, Buckeye, AZ (US); Melissa Marie Alegre, Saginaw, TX (US)

(73) Assignee: Brigham Young University, Provo, UT (US)

( * ) Notice: Subject to any disclaimer, the term of this patent is extended or adjusted under 35 U.S.C. 154(b) by 732 days.

(21) Appl. No.: 12/982,250

(22) Filed: Dec. 30, 2010

(65) Prior Publication Data
US 2011/0176996 A1 Jul. 21, 2011

Related U.S. Application Data

(60) Provisional application No. 61/291,351, filed on Dec. 30, 2009.

(51) Int. Cl.
*G01N 33/574* (2006.01)
*G01N 33/53* (2006.01)
*C07K 16/40* (2006.01)
*A61K 39/00* (2006.01)

(52) U.S. Cl.
CPC .......... *G01N 33/57484* (2013.01); *C07K 16/40* (2013.01); *A61K 2039/505* (2013.01); *G01N 2333/9122* (2013.01); *G01N 2333/91142* (2013.01); *G01N 2333/91215* (2013.01)

(58) Field of Classification Search
USPC .......................... 435/7.23, 7.1, 7.92; 530/350
See application file for complete search history.

(56) References Cited

U.S. PATENT DOCUMENTS

| 4,317,877 | A | 3/1982 | Balis et al. |
| 4,474,893 | A | 10/1984 | Reading |
| 4,722,899 | A | 2/1988 | Hamaoka et al. |
| 4,816,567 | A | 3/1989 | Cabilly et al. |
| 5,476,996 | A | 12/1995 | Wilson et al. |
| 5,514,548 | A | 5/1996 | Krebber et al. |
| 5,698,409 | A | 12/1997 | O'Neill |
| 5,869,045 | A | 2/1999 | Hellstrom et al. |
| 6,083,707 | A | 7/2000 | Eriksson et al. |
| 6,331,415 | B1 | 12/2001 | Cabilly et al. |
| 6,372,217 | B1 | 4/2002 | Uckum |
| 7,311,906 | B2 | 12/2007 | Lallatin et al. |
| 7,837,998 | B2 | 11/2010 | Lallatin et al. |
| 2003/0148410 | A1 | 8/2003 | Berger et al. |
| 2006/0039914 | A1* | 2/2006 | Lallatin et al. ............ 424/155.1 |
| 2007/0003990 | A1 | 1/2007 | Schlegel et al. |
| 2007/0172900 | A1 | 7/2007 | Cahill et al. |
| 2009/0253583 | A1 | 10/2009 | Yoganathan |
| 2010/0143244 | A1 | 6/2010 | Lallatin |
| 2010/0143290 | A1 | 6/2010 | Lallatin |

FOREIGN PATENT DOCUMENTS

| EP | 0042482 A1 | 12/1981 |
| EP | 0255431 B1 | 10/1991 |
| EP | 0454478 A1 | 10/1991 |
| WO | WO9306213 A1 | 4/1993 |
| WO | WO9529192 A1 | 11/1995 |
| WO | WO9708320 A1 | 3/1997 |
| WO | WO0039136 A2 | 7/2000 |
| WO | WO2005113000 A2 | 12/2005 |
| WO | WO 2009/036427 | * 2/2006 ............... C12Q 1/68 |

OTHER PUBLICATIONS

Burgess et al. (J. Cell Biol. 111:2129-2138, 1990).*
Lazar et al. (Mol. Cell Biol. 8:1247-1252, 1998).*
Wen et al. (Proc. Natl. Acad. Sci. U.S.A. 98: 4622-4627, 2001).*
Banfi et al. (Clin Chem Lab Med 2007, 45(5): 565-576).*
datasheet ab56200.*
He et al. (International Journal of Oncology 2004, 25: 945-953).*
O'Neill, K.L. et al. (1987), "Elevated serum and mononuclear leukocyte thymidine kinase activities in patients with cancer," Irish Medical Journal 80:264-265.
O'Neill, K.L. et al. (1987), "Serum thymidine kinase levels in cancer patients," Internal Medicine Digest 13-14.
O'Neill, K.L. et al. (1988), "Elevated levels of thymidine kinase in serum and mononuclear leukocytes from patients," Tumour Biology 8:303-304.
O'Neill, K.L. et al. (1992), "Can thymidine kinase levels in breast tumors predict disease recurrence?," Journal of The National Cancer Institute 84(23):1825-1828.
O'Neill, K.L. et al. (1995), "Thymidine kinase: the future of breast cancer prognosis," The Breast, 4:79-83.
O'Neill K.L. (2001), "Thymidine Kinase: diagnostic and prognostic potential" (review) Expert Rev. Mol. Diagn. 1(4):428-433 or 89-94.
O'Neill, K.L et al. (2007 "Thymidine Kinase 1-A prognostic and diagnostic indicator in ALL and AML patients," Leukemia 21:560-563.

(Continued)

*Primary Examiner* — Yan Xiao
(74) *Attorney, Agent, or Firm* — James Sonntag

(57) ABSTRACT

Compositions and methods are provided for the diagnosis, treatment, and medical management of cancers. The methods include the use of antibodies and other binding molecules that specifically bind to one or more nucleotide salvage pathway enzymes (SPEs) selected from the group consisting of adenine phosphoribosyltransferase (APRT), hypoxanthine-guanine phosphoribosyltransferase (HGPRT), deoxycytidine kinase (dCK); and thymidine kinase 1 (TK1) and complexes comprising SPEs, for detection of the SPE(s) on or in cancer cells and/or on or in body fluids and tissues of cancer patients. Binding of SPEs is useful in the methods provided herein for diagnosing cancer, determining prognosis of cancer and assessing the effectiveness of cancer treatments. Immunoassay systems for use in the methods are also provided, including sandwich immunoassays. In addition, an amino acid sequence comprising a novel TK1 binding site is provided, as well as nucleotide sequences encoding it.

2 Claims, 22 Drawing Sheets

(56) References Cited

OTHER PUBLICATIONS

Persson, L. et al. (1985), "Thymidine kinase in brain tumor cysts," J. Neurosurg., 63:568-572.
Ponomarev, V. et al. (2007), "A Human-Derived Reporter Gene for Noninvasive Imaging in Humans: Mitochondrial Thymidine Kinase Type 2," J. Nucl. Med., 48:819-926.
Rasey, J.S. (2002), "Validation of FLT uptake as a measure of thymidine kinase-1 activity in A549 carcinoma cells," J. Nucl. Med. 43(9):1210-1217.
Robertson, J.F.R. et al. (1990), "Thymidine kinase in breast cancer," British Journal of Cancer 62:663-667.
Robinson et al. (2004) "Improving Monoclonal Antibodies for Cancer Therapy," Drug Development Research, 61:172-187.
Romain, S. et al. (2001), "Dna-Synthesizing Enzymes in Breast Cancer (Thymidine Kinase, Thymidylate Synthase and Thymidylate Kinase): Association With Flow Cytometric S-Phase Fraction and Relative Prognostic Importance in Node-Negative Premenopausal Patients," Int. J. Cancer, 95: 56-61.
Rudnick et al. (2009), "Affinity and Avidity in Antibody-Based Tumor Targeting," Can. Biotherp. & Radiopharm. 24:155-162.
Salfeld (2007), "Isotype Selection in Antibody Engineering," Nature Biotech. 25(12):1369-1372.
Schultze, J.L. (2001), "From cancer genomics to cancer immunotherapy: toward second-generation tumor antigens," Trends in Immunology 22(9):516-523.
Schwartz, J.L., et al. (2004), "Effect of p53 activation on cell growth, thymidine kinase-1 activity, 3'-deoxy-3'fluorothymidine uptake," Nuclear Medicine and Biology, 31:419-423.
Seaver et al. (1994), "Monoclonal Antibodies in Industry: More Difficult Than Originally thought," Genetic Engineering News, 14:14 pp. 10 & 21.
Sherley, J.L. et al. (1988), "Human Cytosolic Thymidine Kinase," J. Biol. Chem. 263(1):375-382.
Sherley, J.L. et al. (1988), "Regulation of Human Thymidine Kinase during the Cell Cycle," J. Biol. Chem. 263 (17):8350-8358.
Shintani, M. et al. (2010), "Immunohistochemical characterization of pyrimidine synthetic enzymes, thymidine kinase-1, and thymidylate synthase, in various types of cancer," Oncology Reports, 23:1345-1350.
Stewart, L.H. et al. (1992), "Thymidine Kinase Activities in Bladder Cancer," Journal of Biomedical Sciences 3(1):13-17.
Stites et al. (1991), "Basic and Clinical Immunology," Seventh Edition, p. 584.
Tajima S. et al. (2002), "Increased Serum Thymidine Kinase Activity in Acute Sarcoidosis," Internal Medicine 41(2):129-132.
Tamiya et al. (1989), Co-Purification of Thymidylate Kinase and Cytosolic Thymidine Kinase from Human Term Placenta by Affinity Chromatography: Biochem. Biophys. Acta 995:28-35.
Thomas, W.M. et al. (1995), "Serum thymidine kinase in colorectal neoplasia," European Journal of Surgical Oncology 21:632-634.
Thurber et al. (2008), "Antibody tumor penetration: Transport opposed by systemic and antigen-mediated clearance," Adv. Drug Deliv. Rev. 60:1421-1434.
Topolcan et at. (2005), "Changes of Thymidine Kinase (TK) During Adjuvant and Palliative Chemotherapy," Anticancer Res. 25:1831-1834.
Von Euler, H.P. et al. (2008), "Monitoring therapy in canine malignant lymphoma and leukemia with serum thymidine kinase 1 activity—evaluation of a new, fully automated non-radiometric assay," International Journal of Oncology, 34:505-510.
Voskoglou-Nomikos (2003), "Clinical Predictive Value of the in Vitro Cell Line, Human Xenograft and Mouse Allograft Preclinical Cancer Models," Clin. Can. Res. 9:4227-4239.
Wang, N. et al. (2001), "Investigation on cell proliferation with a new antibody against thymidine kinase 1," Analytical Cellular Pathology, 23:11-19.
White, C.A. (2001), "Antibody-Targeted Immunotherapy for Treatment of Malignancy," Annu. Rev. Med. 52:125-145.
Willingham et at. (1987), "Pseudomonas Exotoxin Coupled to a Monoclonal Antibody Against Ovarian Cancer Inhibits the Growth of Human Ovarian Cancer Cells in a Mouse Model," Proc. Natl. Acad. Sci. USA 84:2474-2478.
Wilson, et al. (1982), "Human Adenine Phosphoribosyltransferase," J. Bioi. Chem. 257(3):1508-1515.
Wu, Chuanjing et al. (2003), "Production and characterization of a novel chicken IgY antibody raised against C-terminal peptide from human thymidine kinase 1," Journal of Immunological Methods 27(1-2):157-169.
Wu, Jianping, et al. (2000), "A New Cell Proliferating Marker: Cytosolic Thymidine Kinase as Compared to Proliferating Cell Nuclear Antigen in Patients with Colorectal Carcinoma," Anticancer Research 20:4815-4820.
Xu, W. et al. (2009), "Serum thymidine kinase 1 concentration in Chinese patients with chronic lymphocytic leukemia and its correlation with other prognostic factors," Int. J. Hematol., 90:205-211.
Xu, X. et al. (2008), "Serum thymidine kinase 1 reflects the progression of pre-malignant and malignant tumors during therapy," Molecular Medicine Reports, 1:705-711.
Yagihashi, Atsuhito et al. (2005), "Detection of autoantibodies to survivin and livin in sera from patients with breast cancer," Clinica Chimica Acta 362:125-130.
Yusa, T. et al. (1988), "Activity of Cytosolic Isozyme of Thymidine Kinase in Human Primary Lung Tumors with Reference to Malignancy," Cancer Res., 48:5001-5006.
Zhang, F. (2000), PhD Thesis, "Production and characterization of a monoclonal antibody to human thymidine kinase 1 (TK1) and the role of TK1 in cancer management and apoptosis," (Brigham Young University, Department of Microbiology).
Zhang, F. (2001), "A Monoclonal Antibody Specific for Human Thymidine Kinase 1," Hybridoma 20(1):25-34.
Zhang, F. et al. (2001), Thymidine Kinase Immunoassay: a potential marker for breast cancer, Cancer Detection and Prevention 25(1):8-15.
Zhang, J. et al. (2006), "Thymidine Kinase 1: A proliferation marker for determining prognosis and monitoring the surgical outcome of primary bladder carcinoma patients," Oncology Reports, 15:455-461.
Zhang, J-Y. et al. (2003), "Enhancement of Antibody Detection in Cancer Using Panel of Recombinant Tumor-associated Antigens," Cancer Epidemiology, Biomarkers & Prevention 12:36-143.
Zhu, C. (2006), "Effect of C-Terminal of Human Cytosolic Thymidine Kinase (Tk1) on In Vitro Stability and Enzymatic Properties," Nucleosides, Nucleotides and Nucleic Acids 25:1185-1188.
Balzarini et al. (1982), Role of Thymidine Kinase in the Inhibitory Activity of 5-Substituted-2'-Deoxyuridines on the Growth of Human and Murine Tumor Cell Lines: Biochem.Pharmacal. 31(6):1089-1095.
Balzarini, J. et al. (2009), "Human Mitochondrial Thymidine Kinase Is Selectively Inhibited by 3'-Thiourea Derivatives of β-Thymidine: Identification of Residues Crucial for Both Inhibition and Catalytic Activity," Molecular Pharmacology. 75(5):1127-1136.
Barnett, Y.A. et al. (1996), "DNA Damage and Mutagenesis," Irish Area Section Meeting held at the University of Ulster, Coleraine, 1012 Sep. 1996. Biochemial Society Transactions 25:303-308.
Baron et al. (1990), "A Rapid Two-Step Purification of Rat Liver Fetal Thymidine Kinase," Preparative Biochem. 20 (3-4):241-256.
Barrett, I.T. (1983), "Textbook of Immunology," p. 249.
Barthel, H. et al. (2004), "The uptake of 3'-deoxy-3'-[18F]fluorothymidine into L5178Y tumours in vivo is dependent on thymidine kinase 1 protein levels," European Journal of Nuclear Medicine and Molecular Imaging, 32(3):257-263.
Beckman et al. (2007), "Antibody Constructs in Cancer Therapy," Cancer, 109:170-179.
Berenstein, D. et al. (2000), "Valine, Not Methionine, is Amino Acid 106 in Human Cytosolic Thymidine Kinase (TK1)," Journal of Biological Chemistry 275(41):32187-32192.
Berk, A.J. et al. (1973), "A Genetically Distinct Thymidine Kinase in Mammilian Mitochondria: Exclusive Labeling of Mitochondrial Deoxyribonucleic Acid," The Journal of Biological Chemistry, 248(8):2722-2729.

(56) References Cited

OTHER PUBLICATIONS

Boivin et al. (2002), "Intranasal Herpes Simplex Virus Type 2 Inoculation Causes a Profound Thymidine Kinase Dependent Cerebral Inflammatory Response in the Mouse Hindbrain," Eur. J. Neurosci. 16(1):29-43.
Bradshaw, H.D. (1983), "Molecular cloning and cell cycle-specific regulation of a functional human thymidine kinase gene," Proc. Natl. Acad. Sci. vol. 80 pp. 5588-5591.
Bristow, H. et al. (1988), "Leakage of thymidine kinase from proliferating cells," Biochemical Society Transactions, 16:55-56.
Brockenbrough, J. S., et al. (2009), "Thymidine Kinase 1 and Thymidine Phosphorylase Expression in Non-Small-cell Lung Carcinoma in Relation to Angiogenesis and Proliferation," J. Histochem. Cytochem. 57:1087-1097.
Bronzert et al. (1981), "Purification and Properties of the Estrogen-Responsive Cytoplasmic Thymidine Kinase from Human Breast Cancer," Cancer Res. 41:604-610.
Calvert, R.J. et al. (1989), "Comparison of plasma and tissue thymidine kinase activities," Br. J. Cancer, 59:660.
Carlsson, L. et al. (2009), "Elevated levels of thymidine kinase 1 peptide in serum from patients with breast cancer," Upsala J. of Medical Sciences, 114:116-120.
Carter et al. (1992), "Humanization of an anti-p185Her2 antibody for human cancer therapy," Proc. Natl. Acad. Sci. USA, 89:4285-4289.
Carter, P. (2001) Review: "Improving the Efficacy of Antibody-Based Cancer Therapies," www.Nature.com, 1(2):118-29.
Cespdes et al. (2006), "Mouse models in oncogenesis and cancer therapy," Clin. Transl. Oncol. 8(5):318-329.
Chang, Z. et al. (1993), "Constitutive Overexpression of DNA Binding Activity to the Distal CCAAT Box of Human Thymidine Kinase Promoter in Human Tumor Cell Lines," Cancer Res. 53:3253-3256.
Chang, Z. et al. (1993), "The Regulation of Thymidine Kinase in HL-60 Human Promyeloleukemia Cells," J. of Bio. Chem. 268(2):1266-1271.
Chang, Z. et al. (1994), "Differential Phosphorylation of Human Thymidine Kinase in Proliferating and M Phase-arrested Human Cells," The Journal of Biological Chemistry, 269(33):21249-21254.
Chang, Z. et al. (1994), "Human Thymidine Kinase CCAAT-binding Protein is NF-Y, Whose a Subunit Expression is Serum-dependent in Human IMR-90 Diploid Fibroblasts," J. of Bio. Chem. 269(27):17893-17898.
Chang, Z. et al. (1995), "Different Regulation of the Human Thymidine Kinase Promoter in Normal Human Diploid IMR-90 Fibroblasts and HeLa Cells," The Journal of Biological Chemistry, 270(45):27374-27379.
Chatterjee et al. (1994), "Idiotypic antibody immunotherapy of cancer," Cancer Immunol. Imunother., 38:75-82.
Chen, C-C. et al (2006), "Combination of Multiple mRNA Markers (PTTG1, Survivin, UbcH10, and TK1) in the Diagnosis and Taiwanese Patients with Breast Cancer by Membrane Array," Oncology, 70:438-446.
Chen, Y. et al. (2010), "Serum thymidine kinase 1 correlates to clinical stages and clinical reactions and monitors the outcome of therapy of 1,247 cancer patients in routine clinical settings," Int. J. Clin. Oncol., 15:359-368.
Clémenceau, B. et al. (2004), "Preparation of Genetically Homogeneous Antigen-Specific Thymidine Kinase Positive T-Lymphocyte Clones for the Control of Alloreactivity Post-Bone Marrow Transplantation," Human Gene Therapy, 15:542-552.
Co et al. (1994), "A Humanized Antibody Specific for the Platelet Integrin gpIIb/IIIa," Journal of Immunology, 152:2968-2976.
Coppock, D.L. et al. (1987), "Control of Thymidine Kinase mRNA during the Cell Cycle," Molecular and Cellular Biology, 7(8):2925-2932.
Cruse et al. (2004), "Atlas of Immunology," Second Edition, CRC Press, pp. 282 and 640.
Daugherty et al. (1991), "Polymerase Chain Reaction Facilitates the Cloning, CDR Grafting, and Rapid Expression of a Murine Monoclonal Antibody Directed Against the CD18 Component of Leukocyte Integrins," Nuc. Acids res. 19(9):2471-2476.

deHarven, E. et al. (1992), "Antibody Drug Carrier for Immunotherapy of Superficial Bladder Cancer: Ultrastructural Studies," Cancer Res 1992;52:3131-3137.
Dennis, C. (2006), "Off by a Whisker," Cancer News Feature, Nature Publishing Co. pp. 739-741.
Di Raimondo, F. et al. (2001), "Retrospective study of the prognostic role of serum thymidine kinase level in CLL patients with active disease treated with fludarabine," Annals of Oncology, 12:621-625.
Edmond, K.C. et al. (1996) "Identification of a Set of Protein Species Approximately 40 kDa as High-Affinity DNA Binding Factor(s) to the Cell Cycle Regulatory Region of the Human Thymidine Kinase Promoter," Cell Growth & Differentiation 7:1741-1749.
Edmond, K.C. et al. (1997), "Positive and Negative Regulation of the Human Thymidine Kinase Promoter Mediated by CCAAT Binding Transcription Factors NF-Y/CBF, dbpA and CDP/cut1," Cell Growth & Differentiation vol. 8, 1329-1338.
Elholm, M. et al. (2001), "Transient Up-Regulation of Liver Mitochondrial Thymidine Kinase Activity in Proliferating Mitochondria," IUBMB Life, 51:99-104.
Ellims, P.H. et al. (1981), "Prognostic relevance of thymidine kinase isozymes in adult non-Hodgkins lymphoma," Blood, 58:926-930.
Ellims, P.H. et al. (1981), "Thymidine Kinase Isoenzymes in Human Malignant Lymphoma," Cancer Res., 41:691-695.
Ellims et al. (1982), Human Thymidine Kinase: Purification and Some Properties of the TK1 Isoenzyme from Placenta: Mol. Cell. Biochem. 45:113-116.
Flemington (1987), "Sequence, Structure and Promoter Characterization of the Human Thymidine Gene," Gene 52:267-277.
Foekens, J.A., et al. (2001), "Thymidine Kinase and Thymidylate Synthase in Advanced Breast Cancer: Response to Tamoxifen and Chemotherapy," Cancer Res. 61:1421-1425.
Frederiksen, H. et al. (2004), "Effect of valine 106 on structure-function relation of cytosolic human thymidine kinase," Eur. J. Biochem 271:2248-2256.
Fujimori et al. (1990), "A Modeling Analysis of Monoclonal Antibody Percolation Through Tumors: a Binding Site Barrier," J. Nuc. Med. 31:1191-1198.
Fujiwaki, R. et al. (2001), "Clinical Value of Thymidine Kinase in Patients with Cervical Carcinoma," Oncology, 61:47-54.
Fundamental Immunology (1996), 242 (William E. Paul, M.D. ed.), 3d ed.
Gaast, A van der et al. (1991), "Prognostic value of serum thymidine kinase, tissue polypeptide antigen and neuron specific enolase in patients with small cell lung cancer," Br. J. Cancer, 64:369-372.
Gan et at. (1983), "Human Thymidine Kinase," J. Biol. Chem. 258:7000-7004.
Gelbard, A. et al. (1971), "The Effect of X-Irradiation on Thymidine Kinase Activity in Synchronous Populations of HeLa Cells," Radiation Research 46(2)334-342.
Lin, P. et al. (1985), "Molecular Cloning and Structural Analysis of Murine Thymidine Kinase Genomic and cDNA Sequences," Molecular and Cellular Biology 5(11)3149-3156.
Glennie, M.J. (2003), "Renaissance of cancer therapeutic antibodies," Drug Discovery Today vol. 8, No. 11 Jun. 2003, pp. 503-510.
Goding et al. (1980), "Antibody Production by Hybridomas," J. Immunol. Methods 39:285-308.
Greipp, PR, et al. (1993), "Plasma cell labeling index and beta 2-microglublin predict survival independent of thymidine kinase and C-reactive protein in multiple myeloma," Blood 81:3382-3387.
Gronowitz et al. (1984), "Application of an In Vitro Assay for Serum Thymidine Kinase: Results on Viral Disease and Malignancies in Humans," Int. J. Cancer 33:5-12.
Gronowitz, J. et al. (1996), "Thymidine kinase: Biochemical Background and Clinical Applications. I. Background and Use in Gene Therapy," http://biovica.com/wp-content/uploads/2011/05/Thymidine_Gene_therapy.pdf.
Gronowitz, J. et al. (1996), Thymidine kinase: Biochemical Background and Clinical Applications. II. The quantitative assay for TK and its clinical use. http://biovica.com/wp-content/uploads/2011/05/Thymidine_Quantitative_assay.pdf.

(56) References Cited

OTHER PUBLICATIONS

Gross, M.K. et al. (1989), "Thymidine kinase synthesis is repressed in nonreplicating muscle cells by a translational mechanism that does not affect the polysomal distribution of thymidine kinase mRNA," Proc. Natl. Acad. Sci., 86:4987-4991.

Gudas, J.M., et al. (1990), "Ordered Splicing of Thymidine Kinase Pre-mRNA during the S phase of the Cell Cycle," Molecular and Cellular Biology, 10(10):5591-5595.

Gura, T. (1997), "Systems for Identifying New Drugs are Often Faulty," Science 278:1041-1042.

Habteyesus, A et al. (1991), "Deoxynucleoside Phosphorylating Enzymes in Monkey and Human Tissues Show Great Similarities, While Mouse Deoxycytidine Kinase Has a Different Substrate Specificity," Biochemical Pharmacology, vol. 42. No. 9. 1829-1836.

Hagberg, H. et al. (1984), "Serum thymidine kinase in acute leukemia," Br. J. Cancer, 49:537-540.

Hallek, M. (1992), "Thymidine Kinase: a tumor marker with prognostic value for non-Hodgkin's lymphoma and a broad range of potential clinical applications," Ann. Hematol. 65:1-5.

Hallek, M. et al. (1997), "Serum thymidine kinase levels are elevated and exhibit diurnal variations in patients with advanced ovarian cancer," Clinica. Chimica. Acta., 267:155-166.

Hallek, M. et al. (1999), "Elevated Serum Thymidine Kinase Levels Identify a Subgroup at High Risk of Disease Progression in Early, Nonsmoldering Chronic Lymphocytic Leukemia," Blood, 93:1732-1737.

Hannigan et al. (1993) "Thymidine Kinase: The Enzymes and Their Clinical Usefulness," Cancer Biother. 8(3):187-197.

Haveman, J. et al. (2006), "Time course of enhanced activity of deoxycytidine kinase and thymidine kinase 1 and 2 in cultured human squamous lung carcinoma cells, SW-1573, induced by Á(y)-irradiation," Oncology Reports, 16:901-905.

He, Q. et al. (2000), "The clinical significance of thymidine kinase 1 measurement in serum of breast cancer patients using anti-TK1 antibody," The International Journal of Biological Markers, 15(2):139-146.

He Q. et al. (2002), "X-irradiation effects on thymidine kinase (TK): II. The significance of deoxythymidine triphosphate for inhibition of TK1 activity," Cell Prolif. 35(2):69-81.

He, Q. et al. (2006), "Thymidine Kinase 1 in Serum Predicts Increased Risk of Distant or Loco-regional Recurrence Following Surgery in Patients with Early Breast Cancer," Anticancer Res. 26:4753-4760.

Hengstschläger, M. et al. (1993), "Cytofluorometric Assay for the Determination of Thymidine Uptake and Phosphorylation in Living Cells," Cytometry 14: 39-445.

Hengstschläger, M. et al. (1994), Different Regulation of Thymidine Kinase During the Cell Cycle of Normal Versus DNA Tumor Virus-Transformed Cells: J. Biol. Chem. 269:13836-13842.

Hengstschläger, M. et al. (1994,) "A Common Regulation of Genes Encoding Enzymes of the Deoxynucleotide Metabolism is Lost After Neoplastic Transformation," Cell Growth Differ. 5(12):1389-1394.

Hohn-Elkarim, K. et al. (1990), "Modification of effects of radiation on thymidine kinase," Int. J. Radiat. Biol., 58(1):97-110.

Huang, D. et al. (2001), "Interaction of human thymidine kinase 1 with p21Waf1," Biochem. J. 356:829-834.

Jain (1994), "Barriers to Drug Delivery in Solid Tumors," Scientific American pp. 58-65.

Jansson et al. (1992), "Mammalian Thymidine Kinase 2, Direct Photoaffinity Labeling with [32P]dCTP of the Enzyme from Spleen, Liver, Heart and Brain," Eur. J. Biochem. 206(2):485-490.

Karbownik, M. et al. (2003), "Expression of Genes for Certain Enzymes of Pyrimidine and Purine Salvage Pathway in Peripheral Blood Leukocytes Collected form Patients with Graves' or Hashimoto's Disease," Journal of Cellular Biochemistry 89:550-555.

Kauffman et al. (1991), "Cell cycle regulation of thymidine kinase: Residues near the carboxyl terminus are essential for the specific degradation of the enzyme at mitosis," Mol. Cell Biol. 11:2538-2446.

Kim, Y.K., et al. (1992), "Identification of a Protein-binding Site in the Promoter of the Human Thymidine Kinase Gene Required for the G1-S-regulated Transcription," The Journal of Biological Chemistry, 267(4):2723-2727.

Knight, G.B. et al. (1987), "Cell-cycle-specific interaction of nuclear DNA-binding proteins with a CCAAT sequence from the human thymidine kinase gene," Proc. Natl. Acad. Sci. USA vol. 84, pp. 8350-8354.

Kohler et al. (1976), "Derivation of Specific Antibody-Producing Tissue Culture and Tumor lines by Cell Fusion," Eur. J. Immunol. 6:511-519.

Kok, M. et al. (2003), "Serum Soluble CD27, but Not Thymidine Kinase, is an Independent Prognostic Factor for Outcome in Indolent Non-Hodgkins Lymphoma," Tumor Biol., 24(1):53-60.

Konoplev, S.N. et al. (2010), "High Serum Thymidine Kinase 1 Level Predicts Poorer Survival in Patients with Chronic Lymphocytic Leukemia," Am. J. Clin. Pathol., 134:472-477.

Lau et al. (1984), "Direct Isolation of the Functional Human Thymidine Kinase Gene with a Cosmid Shuttle Vector," Proc. Natl. Acad. Sci. USA 81:414-418.

Lewiński, A. et al. (2004), "Increased Thymidine Kinase Activity in Human Thyroid Toxic Adenomas: Effects of Exposure to Epidermal Growth Factor In Vitro," Endocrine Research, 30(1):37-46.

Lewiń ski, A. et al. (2004), "Increased Thymidine Kinase Activity in Human Thyroid Toxic Adenomas: Effects of Exposure to Epidermal Growth Factor In Vitro," Endocrine Research, 30(1):37-46.

Luo, P. et al. (2010), "The Proliferation Marker Thymidine Kinase 1 Level is High in Normal Kidney Tubule Cells Compared to other Normal and Malignant Renal Cells," Pathology Oncology Research 16(2):277-283.

Mao, Y. et al. (2002), "A Comparative Study: Immunohistochemical Detection of Cytostolic Thymidine Kinase and Proliferating Cell Nuclear Antigen in Breast Cancer," Cancer Investigation; Marcel Dekker, Inc., 20(7,8):922-931.

May et al. (1991), Intracellular Routing Rather than Cross-Linking or Rate of Internalization Determines the Potency of Immunotoxins Directed Against Different Epitopes of sIgD on Murine B Cells: Cell Immunol. 135:490-500.

McKenna, P.G. et al. (1988), "Thymidine kinase activities in mononuclear leukocytes and serum from breast cancer patients," British Journal of Cancer 57:619-622.

Mikulits, W. et al. (1996), "Overexpression of Thymidine Kinase mRNA Eliminates Cell Cycle Regulation of Thymidine Kinase Enzyme Activity," The Journal of Biological Chemistry, 271(2):853-860.

Munch-Peterson et al. (1990), "Thymidine Kinase in Human Leukemia—Expression of Three Isoenzyme Variants in Six Patients with Chronic Myelocytic Leukemia," Leuk. Res. 14(1):39-45.

Munch-Peterson et al. (1991), "Diverging Substrate Specificity of Pure Human Thymidine Kinases 1 and 2 Against antiviral Dideoxynucleosides," J. Biol. Chem. 266:9032-9038.

Munch-Peterson et al. (1993), "Reversible ATP-Dependent Transition between Two Forms of Human Cytosolic Thymidine Kinase with Different Enzymatic Properties," J. Biol. Chem. 268(21):15621-15625.

Munch-Peterson, B. et al. (2007), "Deoxynucleoside Kinases and Their Potential Role in Deoxynucleoside Cytotoxicity," Cancer Drug Discovery and Development: Deoxynucleoside Analogs in Cancer Therapy, Humana Press Inc., Totowa, NJ pp. 53-79.

Munch-Peterson, B. (2010), "Enzymatic Regulation of Cytosolic Thymidine Kinase 1 and Mitochondrial Thymidine Kinase 2: A Mini Review," Nucleosides, Nucleotides, and Nucleic Acids, 29:363-369.

Nesterova, M. et al. (2006), "Autoantibody biomarker opens a new gateway for cancer diagnosis," Biochimica et Biophysica Acta 1762:398-403.

Öhrvik, A et al. (2004), "Sensitive Nonradiometric Method for Determining Thymidine Kinase I Activity," Clinical Chemistry, 50(9):1597-1606.

Oldham et al. (1993), "Whats the Score," Cancer Biother. 8(3):187-188.

* cited by examiner

US 9,267,948 B2

COMPOSITIONS AND METHODS FOR CANCER MANAGEMENT USING ANTIBODIES BINDING TO NUCLEOTIDE SALVAGE PATHWAY ENZYMES AND COMPLEXES THEREOF

CROSS-REFERENCE TO RELATED APPLICATIONS

This application claims priority to U.S. Provisional Patent Application No. 61/291,351 filed Dec. 30, 2009, which is incorporated herein by reference to the extent not inconsistent herewith.

BACKGROUND

In 2007 it was reported that over half a million people died from cancer and more than 1.4 million new cases were diagnosed in the United States. Thus, it is important to diagnose, assess prognosis for, and monitor treatment of cancer. Improved, noninvasive diagnostic compositions and methods using cancer-specific markers that provide strong discrimination between biological samples from cancer patients and normal individuals are especially needed in the art.

The nucleotide salvage pathway is a pathway in which nucleotides (purines and pyrimidines) are synthesized from intermediates in the degradative pathway for nucleotides. Salvage pathway enzymes are used to recover bases and nucleosides that are formed during degradation of RNA and DNA. This is important because some tissues cannot undergo de novo synthesis. There are two major pathways that lead to the production of nucleotides: the de novo pathway and the salvage pathway. The de novo synthesis of DNA begins with metabolic precursors such as amino acids, ribose 5-phosphate, and others known to the art. Most organisms also synthesize nucleotides through a salvage pathway that utilizes the degraded nucleotides from DNA, recycling nucleic acids rather than destroying them, providing an energy efficient way to produce nucleotides. This is accomplished through the enzymatic activities of adenine phosphoribosyltransferase (APRT) and hypoxanthine-guanine phosphoribosyltransferase (HGPRT), for purines, and thymidine kinase 1 (TK1) and deoxycytidine kinase (dCK) for pyrimidines, producing oligonucleotides which are further digested by phosphodiesterases to yield free nucleosides.

The de novo pathway to deoxythymidine triphosphate (dTTP) synthesis first requires the use of deoxyuridine monophosphate (dUMP) from the metabolism of either uridine diphosphate (UDP) or cytidine diphosphate (CDP). The dUMP is converted to deoxythymidine monophosphate (dTMP) by the action of thymidylate synthase. The methyl group of thymine is donated by N5,N10-methylene tetrahydrofolate (THF), similar to the donation of methyl groups during the biosynthesis of the purines. The unique property of the action of thymidylate synthase is that the THF is converted to dihydrofolate (DHF), the only such reaction yielding DHF from THF. In order for the thymidylate synthase reaction to continue, THF must be regenerated from DHF. This is accomplished through the action of dihydrofolate reductase (DHFR). THF is then converted to N5,N10-THF via the action of serine hydroxymethyl transferase.

Expression of genes related to DNA replication is maximal during early S phase. TK1, APRT, HGPRT and dCK are cellular enzymes involved in a salvage pathway of DNA synthesis. In normal growing cells these salvage pathway enzymes' mRNA levels rise near the G1-S boundary, peak in early S phase, and return in G2 to approximately the level of early G1. They are activated in the G1/S phase of the cell cycle. DNA synthesis is primarily dependent upon salvage mechanisms to supply deoxypyrimidine nucleotides. Antisense inhibition of the de novo pathway of pyrimidine synthesis results in a compensatory stimulation of the less energy-consuming salvage pathways. The salvaged bases and nucleosides can then be converted back into nucleotides.

Thymidine kinase 1 (TK1) is an S-phase-regulated specific protein which is found both in normal individuals and in cancer patients. TK1 catalyses the reaction of thymidine to deoxythymidine monophosphate (dTMP) using adenosine triphosphate (ATP), and dCK works similarly with cytidine as its substrate. APRT and HGPRT both use phosphoribosyl pyrophosphate to phosphorylate adenine and guanine to adenosine monophosphate (AMP) and guanosine monophosphate (GMP) respectively.

Substantial research has been performed on TK1, but comparatively little research has been done on the other nucleotide salvage pathway enzymes as related to cancer. Mammalian cells express two different isoenzymes, TK1 and TK2, originally called fetal and adult TK, respectively. TK1 was originally called fetal TK since it was predominantly found in the fetus. The fetal isoenzyme, TK1, is associated with cell division, and its levels increase as the cell is dividing.

U.S. Pat. No. 5,698,409 (incorporated herein by reference) describes a mammalian TK1 purified from Raji cells and a TK1-specific monoclonal antibody. The monoclonal antibody binds to TK1 and inhibits TK1 activity. The TK1 monoclonal antibody was used for cancer diagnosis. U.S. Pat. Nos. 7,311,906 and 7,837,998, incorporated herein by reference, refer to TK1-specific monoclonal antibodies produced by hybridomas on deposit with American Type Culture Collection (ATCC), 10801 University Blvd, Manassas, Va., under Accession Nos. ATCC HB 11432, HB 11433, HB 11434 and PTA-670.

Other references of interest are listed in the References section below and incorporated herein by reference for purposes of enablement and written description.

SUMMARY

The use of specific antibodies to target tumor cells is an approach which can leave normal, non-malignant tissue unharmed. Specific antibodies can be used to construct therapeutic reagents with selectivity for certain populations of cells. Optionally, monoclonal antibodies (Mabs) or other cell-targeting proteins are linked to bioactive moieties to form biotherapeutic agents referred to as immunoconjugates, immunotoxins or fusion proteins, which can combine the selectivity of the targeting moiety with the potency of the bioactive moiety. Embodiments provided herein are directed to the use of anti-salvage pathway enzyme antibodies to target cancer cells and also inhibit cell proliferation in non-normal cells, such as cancer cells, that synthesize and overexpress these enzymes.

Nucleotide salvage pathway enzymes (SPEs) including adenine phosphoribosyltransferase (APRT), hypoxanthine-guanine phosphoribosyltransferase (HGPRT), deoxycytidine kinase (dCK); and thymidine kinase 1 (TK1) are produced in large quantities by cancer cells but not by normal cells, and they are released into the serum of the cancer patient. We have shown that elevated levels of these enzymes in the serum of cancer patients directly reflect a patient's cancer stage. Higher levels correlate with more advanced cancer stages. Early detection of tumors can be achieved by monitoring the levels of these enzymes in serum samples of a population. One exemplary method for detecting nucleotide salvage pathway enzymes uses sandwich immunoassays, including sandwich enzyme-linked (ELISA) assays, for each of these enzymes or combinations of two, three or all four of these enzymes, allowing for the accurate evaluation and prediction of disease severity when measured individually, and especially when measured collectively.

Embodiments of the methods and materials provided herein meet a need in the art for compositions and methods useful to diagnose, assess prognosis for, and monitor treatment of cancer. Improved, noninvasive diagnostic compositions and methods using nucleotide salvage pathway enzymes (SPEs) as cancer-specific markers that provide strong discrimination between biological samples from cancer patients and normal individuals are provided.

SPE activity levels correlate with the aggressiveness of tumor cells. Malignant cells have lost the strict regulation of SPE that is observed in normal cells. SPE activity levels are a major biochemical marker of cell proliferation, and SPE levels are elevated in malignancies. The elevation of SPE levels in malignancies is not simply the result of cellular proliferation, but is directly caused by alteration of regulatory mechanisms in cancer cells, which constitutively express SPE mRNA.

The compositions and methods disclosed herein include antibodies and other binding molecules that specifically bind to SPEs and complexes comprising SPEs, used in methods for detection of one or more SPEs on the surfaces, and inside, of cancer cells and/or in the body fluids and tissues of cancer patients. Embodiment hereof provide binding partners having both improved specificity and selectivity for the SPEs, for example, when contacting the SPEs in patient samples, including fluid samples such as serum or other biological fluid samples. Additional embodiments hereof are directed to methods of diagnosing cancer and/or determining prognosis and/or assessing the effectiveness of cancer treatments via estimation of SPE levels on the surfaces of cancer cells and/or in the serum of cancer patients, with elevated levels indicating cancer, and increasingly elevated levels indicating a poor prognosis for the disease, or an insufficiently effective treatment regimen.

Embodiments disclosed herein relate to the diagnosis and medical management of cancer, including assessing prognosis, visualizing, monitoring and treating cancer using monoclonal and polyclonal antibodies and/or other binding partners with specificity for SPEs and complexes found on the surface of cancer cells and/or in circulation or other bodily fluids, i.e., TK1, APRT, HGPRT, and dCK. As used herein, the terms "nucleotide salvage pathway enzyme" and "salvage pathway enzyme" are synonymous.

To diagnose the presence of cancer in a mammal suspected of having cancer, a single measurement of one or more SPEs can be sufficient. If one or more of these enzymes are significantly elevated over normal (e.g., as shown in FIGS. 2-4, 6-8, and 13-19 hereof), this is diagnostic of the presence of cancer. The methods hereof comprise testing for the presence and amount of one or more salvage pathway enzymes (SPEs) in a biological sample from the mammal. Testing is done by first contacting a biological sample from the mammal with one or more SPE-binding molecules that specifically bind to an SPE target selected from the group consisting of one or more APRT, HGPRT), dCK, and TK1, combinations of any two, three or four of these SPEs; and complexes comprising any one, two, three or four of these SPEs; wherein, when TK1 is the only target tested for, at least one binding molecule specific to TK1 is used, which binding molecule is not an antibody that binds to the C-terminal of TK1. The TK1-binding site to which the binding molecule binds can be a binding site having an amino acid sequence comprised in the sequence: QYKCLVIKYAKDTRYSSSFCTHDRNT-MEALPACLLRDVAQEALGVAVIGIDEGQFFPDIVEF CEAMANAGKTVIVAALDGTFQRKPF-GAILNLVPLAESV [SEQ ID NO. 1] or comprised in a sequence 85%, 90% 95%, 97% or 99% homologous to SEQ ID NO:1. Next, the presence and amount of the SPEs in the sample are determined by detecting the presence and amount of binding of the SPE-binding molecules to the SPE targets; and cancer is diagnosed when the targets are present in a cancer-diagnostic amount.

The TK1 can be in active (tetrameric) or less active dimeric or monomeric) forms.

The term "SPE-binding molecule" includes antibodies, antibody fragments, and other molecules such as synthesized molecules, fusion proteins, and other molecules known to the art that are capable of binding to the SPEs and complexes thereof.

The term "specifically binds" with respect to an SPE-binding molecule means that the SPE-binding molecule bind to one SPEs and not to other targets. When the SPEs are complexed, binding sites not present on a single SPE can be formed by protein folding in the complex such that adjacent portions of a binding site are portions of different SPEs. SPE-binding molecules specific to the complex will bind to the complex but not to individual SPEs. The binding is strong enough to form an SPE-binding molecule-target complex that persists through subsequent method steps.

A "cancer diagnostic amount" of SPEs or of complex(es) of one or more SPEs, is an amount greater than the average range of the SPEs or complexes in a sample of the same material taken from a normal mammal that does not have cancer. To determine whether or not SPE-binding molecule binding is present in a biological sample in a cancer-diagnostic amount, any means known to the art, including the methods disclosed herein, can be used for comparing the amount of binding detected in the sample with the amount of binding detected in normal samples of the same type. In an embodiment, samples are taken from a normal population of mammals who do not have cancer and from a population of mammals of the same type who have cancer, and standard curves or data tables prepared showing the amount of binding for each sample. To determine a cancer-diagnostic amount of binding, the binding in a particular sample is compared to the standard curves or data tables. Standard curves or data tables specific to different cancers and to different stages of cancers are prepared in the same way to provide more accurate diagnoses.

The term "biological sample" as used herein refers to a sample from a mammal, including, but not limited to, any fluid obtained from a mammal, for example, blood, plasma, serum, cerebrospinal fluid, urine, peritoneal exudate, saliva, tears, snot, lymph fluid, seminal fluid, milk, milk duct fluid, tissue, and liquefied tissue; or it can be a material, especially a liquid sample, homogenate, exudate or cytoplasmic sample prepared from a body organ, tissue, cell, fluid, or other body component, in either normal or diseased condition and presented in any form, for example, as a fresh or preserved specimen, including a histological slide specimen. In embodiments the biological sample is present on a slide, and detecting the presence and amount of the SPE(s) is performed by contacting the sample with antibody(ies) labeled with a stain.

The "C-terminal of TK1" as used herein refers to the portion of the C-terminal end of TK1 to which previously-known antibodies such as CB001 bind. The C-terminal as used herein consists of the 40 amino acids at the end of the polypeptide, typically amino acids 194-234. If a TK-1 binding molecule binds to any amino acids in the C-terminal end even if the binding site is only partially within amino acids 194 to the end of the protein, the molecule is considered to bind the C-terminal. For example, if a binding molecule binds to amino acids on TK1 that are not on the C-terminal, but also binds to amino acids that are on the C-terminal, it is considered to bind to the C-terminal.

The use in some methods hereof of certain anti-TK1 antibodies that bind to the C-terminal of TK1 by themselves, i.e., in methods not requiring the use of antibodies to other SPEs or SPE complexes, or not requiring the use of antibodies that bind to other sites on TK1, is taught in U.S. Pat. Nos. 5,698,409 and 7,837,998, which are incorporated by reference to the extent not inconsistent herewith. As disclosed herein, the present methods utilize combinations of anti-TK1 antibodies that bind to different sites on TK1, and combinations of anti-TK1 antibodies with one or more antibodies to other SPEs, and utilize antibodies to other SPEs singly or in combination with each other.

Any means for testing binding of the SPE-binding molecules known to the art can be used, including enzyme-linked-immunosorbent serologic assay (ELISAs) such as direct, indirect, sandwich, competitive and multiplex ELISAs, immunoassays in kit formats, such as in cartridge or dipstick format, Western blots, and cell-sorting and separation devices. Detection of elevated SPEs in samples or patients can be done by any means known to the art, including radioassay, chromatography, fluorescence-activated cell sorting, imaging of the body with appropriately labeled SPE-binding molecules specific to one or more individual SPEs, and other methods known to the art including assaying SPE activity utilizing ELISA methods as disclosed herein or other means known to the art such as methods using radio-labeling to measure SPE levels.

The methods provided herein can also comprise incubating the biological sample with a chelating agent, a reducing agent, and/or a detergent known to the art in an amount sufficient to release one or more individual SPEs from a complex with other molecules in which it can exist in the sample. As specifically exemplified, the chelating agent can be, but is not limited to, EDTA (ethylenediaminetetraacetic acid) or it can be EGTA (ethylene glycol-bis(β-aminoethyl ether)-N,N,N',N'-tetraacetic acid) or DTPA (diethylenepentaacetic acid), BAPTA (1,2-bis(2-aminophenoxy)ethane-N,N,N',N'-tetraacetic acids tetrakis) or DMPS (sodium 2,3 dimercaptopropanesulfonate monohydrate). In embodiments, the reducing agent is selected from the group consisting of 1,4-dithiothreitol (DTT), tris(2-carboxyethyl)phosphine (TCEP), dithioerythritol (DTE), and β-mercaptoethanol (BME); or it can be another reducing agent known in the art. Suitable detergents are known to the art and include, but are not limited to, polysorbate 20 (Tween 20), octyl phenyl ether (Triton-X), polysorbate 80 (Tween 80), hexadecyltrimethylammonium bromide (CTAB), polyethylene glycol ether (POE(10)L), tetradecyltrimethylammonium bromide (TTAB), and n-Tetradecyl-N,N-dimethyl-3-ammonio-1-propanesulfonate (Zwittergent 3-14).

The antibodies used can be monoclonal antibodies or polyclonal antibodies, or when more than one antibody is used in the method, a combination of monoclonal and polyclonal antibodies can be used.

The mammal can be a human or any other animal taxonomically designated as a mammal.

The cancer can be any cancer known to the art. Because all cancers involve cell proliferation, and the SPEs are overexpressed on cancer cell surfaces and in body fluids and cancer tissues during cell division (proliferation), all cancers can be identified by detecting SPEs on cancer cell surfaces as well as in biological fluid and cancer tissue samples in cancer-diagnostic amounts specific to different cancers and to different stages of cancers. Some specific cancers that can be diagnosed, treated and visualized by the methods disclosed herein are selected from the group consisting of lung cancer, bone cancer, pancreatic cancer, skin cancer, cancer of the head or neck, cutaneous and intraocular melanoma, uterine cancer, ovarian cancer, rectal cancer, cancer of the anal region, stomach cancer, colon cancer, liver cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer, and combinations thereof. In embodiments, the cancers are selected from the group consisting of lymphoma, breast, liver, cervical and pancreatic cancers.

Medical management of cancers requires information not only about the existence of cancer in a patient, but also its presence or absence in various tissues and organs, i.e., its extent. In addition, it is useful to know how aggressive the cancer is, i.e., how quickly and how much it has spread in the past, and how responsive it is to various treatments, for example, how quickly the spreading can be stopped or reduced by selected treatments.

To determine the extent of the cancer, samples can be taken from different organs and tissues, and the presence of cancer in these organ and tissues determined by detecting the presence of one or more SPEs in each sample. To determine the extent of the cancer, binding molecules such as antibodies specific to one or more SPEs can be linked with detectable labels such as fluorescent, magnetic or radioactive moieties, and then visualized in vitro or in the patient's body by methods such as Positron Emission Tomography (PET), Magnetic Resonance Imaging (MRI), Computed Tomography (CT), Single Photon Emission Computed Tomography (SPECT), and others known to the art.

To assess the aggressiveness of a cancer or its responsiveness to a given treatment, measurements of one or more SPEs or complexes thereof can be taken at different times and compared. The prognosis of a patient's cancer can be assessed by comparing the amounts of one or more SPEs or complexes thereof present in the earlier and later samples, so that it can be predicted whether the cancer will further spread, recur, or disappear. For example, if the same amount of one or more SPEs or complexes thereof is present in a patient sample taken at a later time than in a sample taken earlier, in the absence of intervening treatment, this would indicate that the cancer is not rapidly worsening and a conservative treatment might be prescribed. If a lesser amount of one or more SPEs or complexes thereof is present in a patient sample taken later than in a sample taken earlier, this would indicate that the cancer may be in remission, and a wait-and-see approach might be prescribed. If a greater amount of one or more SPEs or complexes thereof is present in a patient sample taken later than in a sample taken earlier, this would indicate that the cancer is worsening at a rate that can be calculated based on the amount of the increase over the period of time between the measurements, i.e., the rate of change in severity of the cancer is determined by a method comprising assessing the change in amount of antibody complexes over the period of time elapsed between a first time T1 when said first sample is taken and a second time T2 when said second sample is taken. The rate of change can be extrapolated into the future to predict the time of remission of cancer or death of the mammal. Methods are known to the art for calculating such rates of change from data and extrapolating them into the future to determine an expected cancer severity at a later time. In the case of a rapidly-worsening cancer, an aggressive treatment would be indicated, or if the cancer is already widespread, it might be considered untreatable, and only palliative measures prescribed.

When the methods hereof are used to monitor the effectiveness of a cancer treatment, that is, if the patient has been treated during the interval between the measurements, the same or a greater amount of one or more SPEs or complexes thereof found to be present at the later time would indicate that a more aggressive treatment should be prescribed. If the later measurement indicates a decrease in SPEs or complexes thereof in the patient sample, and the rate of decrease is considered satisfactory, the same treatment could profitably be continued, or less aggressive treatments prescribed. In addition to monitoring the effectiveness of treatments in a patient over time, the relative effectiveness of different treatments can be compared across a patient population by comparing samples from different patients. When TK1 is the only SPE measured in these methods, at least one TK-1 binding molecule should be used that is not an antibody that binds to the C-terminal of TK1.

The methods of medical management provided herein are methods for comparing the severity of cancer shown by at least two different biological samples taken from a mammal. The methods comprise: a) contacting a first biological sample from a mammal with at least one first SPE-binding molecule specific for a target which is a target selected from the group consisting of TK1, APRT, HGPRT, and dCK; and combinations of any two, three or four of the SPEs; and complexes comprising any one, two, or three, or four of the SPEs; to form one or more first SPE-binding molecule complexes comprising the SPE-binding molecule(s) and the target(s); b) detecting the presence and amount of the first SPE-binding molecule complex(es) in the sample by detecting the presence and amount of binding of the SPE-binding molecule(s) to said target(s); wherein the severity of said cancer is proportional to the presence and amount of the SPE-binding molecule complex(es) in the samples; and c) testing for the presence and amount of the SPE target(s) in a second biological sample of the same material as the first biological sample, by contacting the second biological sample with one or more second SPE-binding molecule(s) that specifically bind to the first target(s) to form one or more second SPE-binding molecule complexes comprising the second SPE-binding molecule(s) and the SPE target(s); and d) comparing the amount of the first SPE-binding molecule complex(s) in the first sample with the amount of the second SPE-binding molecule complex(s) in the second sample, wherein a greater amount of SPE-binding molecule complex(es) in one of the samples indicates a greater severity of cancer in the mammal from which that sample was taken; and wherein when TK1 is the only target, at least one of said first or second SPE-binding molecules is not an antibody that specifically binds to the C-terminal of TK1. The TK1 can be in tetrameric (active), dimeric, or monomeric (less active) form. The first and second SPE-binding molecules for each SPE can be the same, except in the case of the TK1-binding molecules.

In embodiments, the method also comprises, prior to contacting said first and second biological samples with said SPE-binding molecule(s), incubating said samples with a chelating agent, and/or a reducing agent, and/or a detergent in an amount sufficient to release said SPE from a complex with other molecules in which it can exist in the samples.

The method can be used to compare multiple samples, taken from the same mammals at different times, or can be taken from multiple different mammals. The term "multiple samples" as used herein refers to two or more samples.

Any combination of SPEs can be tested for in the samples. In an embodiment, only TK1 and APRT are tested for in the samples.

In embodiments, the rate of change in severity of the cancer is determined by a method comprising assessing the change in amount of antibody complexes over the period of time elapsed between a first time T1 when the first sample is taken and a second time T2 when the second sample is taken from the same mammal. In embodiments, multiple samples are taken at multiple times (T1-Tn), and the rate of change in cancer severity is extrapolated into the future to predict the time of remission of cancer or death of the mammal.

In embodiments, the prognosis of the cancer is assessed in the absence of intervening treatment between a first time T1 when said first sample is taken and a second time T2 when said second sample is taken.

In embodiments, the effectiveness of a cancer treatment is assessed, wherein the cancer treatment is conducted between a first time T1 when the first sample is taken and a second time T2 when the second sample is taken.

Sandwich immunoassays can be used in the methods described above for medical management of cancers. Methods using sandwich immunoassays can comprise: a) contacting a first biological sample taken from a mammal at a time T1 with at least one first SPE-binding molecule specific to at least one target selected from the group consisting of APRT, HGPRT, dCK, TK1; combinations of any two, three or four of said SPEs; and complexes comprising any one, two or three or four of said SPEs; to form a first SPE-binding molecule complex comprising the first SPE-binding molecule and the SPE target; b) contacting the first antibody complex with a second SPE-binding molecule, which binds specifically to a different binding site on the SPE target than the first SPE-binding molecule, to form a second SPE-binding molecule complex comprising the first SPE-binding molecule, the second SPE-binding molecule and the SPE target; c) detecting the presence and amount of the second SPE-binding molecule complex in the sample; d) contacting a second biological sample taken from said mammal at a time T2 different from T1, or taken from a different mammal, with a third SPE-binding molecule specific for the SPE target; to form a third SPE-binding molecule complex comprising the third SPE-binding molecule and the SPE target; e) contacting the third SPE-binding molecule complex with a fourth SPE-binding molecule, which binds to a different binding site on the third SPE-binding molecule complex than the third SPE-binding molecule, to form a fourth SPE-binding molecule complex comprising the fourth SPE-binding molecule, the third SPE-binding molecule, and the target; and f) comparing the amount of the fourth SPE-binding molecule complex with the amount of the second SPE-binding molecule complex, wherein a greater amount of SPE-binding molecule complex in a sample indicates a greater severity of cancer in the mammal providing the sample at the time the sample was taken; and wherein, when TK1-binding molecules are the only SPE-binding molecules in the immunoassay, at least one of the SPE-binding molecules is not an anti-TK1 antibody that binds to the C-terminal of TK1.

Also provided herein are immunoassay systems, which can be integrated immunoassay devices, for detecting a cancer-diagnosing level of one or more SPEs or complexes thereof in a biological sample from a mammal. An "integrated immunoassay device" as used herein is one in which the elements of the system are physically connected, e.g., by means of a connecting material, such as a fluid in a flow path, or by being disposed within the same housing.

The immunoassay system comprises one or more SPE-binding molecules specific for a target selected from the group consisting of APRT, HGPRT, dCK; and TK1, combinations of any two, three or four of said SPEs; and complexes comprising one, two, three or four of said SPEs present in a biological sample from the mammal, and means operationally connected with the SPE-binding molecule(s) for detecting binding of the SPE-binding molecule(s) to the SPE target(s) at a level diagnostic of cancer. The operational connection can comprise: a) a flow path capable of flowing a sample and/or said SPE-binding molecules into contact with each other; and b) means for flowing a sample containing a complex comprising the SPE-binding molecules and the SPE target and the means for detecting binding into contact with each other.

The means for detecting binding at a level diagnostic of cancer can comprise any such means known to the art including masking means for masking non-cancer-diagnostic levels of SPE-molecule binding in the sample, such as filter means having the same color or tone as indicators showing non-cancer levels, or means for measuring intensity of color or luminescence or radioactivity, or other means known to the art, including electronically comparing said detected levels with levels in a database containing cancer and normal levels stored in a computer processor.

The immunoassay can be a sandwich assay comprising capture and detection SPE-binding molecules as is known to the art, and can be in the form of a dipstick or cartridge and can be included in a kit such as a kit containing required reagents and instructions for use.

When TK1 is the only target tested for, at least one binding molecule specific to TK1 is used which is not an antibody that binds to the C-terminal of TK1. The anti-TK1 binding molecule can be an antibody or other binding molecule specific to a binding site having an amino acid sequence comprised in SEQ ID NO:1, or comprised in a sequence having at least 85%, 90%, 95%, 97% or 99% homology to SEQ ID NO:1. When this immunoassay is a sandwich immunoassay comprising different TK1-binding molecules that are respectively used for capture and detection of TK1, one of the binding molecules can bind to the C-terminal of TK1 and one can bind to an amino acid sequence comprised in SEQ ID NO:1 or comprised in homologous sequences as defined above.

A method of treating cancer by inhibiting proliferation of cancer cells that overexpress one or more SPEs selected from the group consisting of APRT, HGPRT, dCK and TK1, in a mammal is provided herein, wherein said SPE(s) is/are found on surfaces of said cells, said method comprising administering to said mammal a pharmaceutical composition comprising an anticancer agent comprising one or more binding molecules that bind specifically to a target selected from the group of said SPE(s); combinations of any two, three, or four of said SPEs; and complexes comprising any one, two, three or four of said SPEs; wherein said pharmaceutical composition is administered to said mammal in an amount sufficient to inhibit proliferation of said cells, whereby proliferation of said cancer cells is inhibited; and wherein when TK1 is the only target, an SPE-binding molecule is used that is not an antibody that binds to the C-terminal of TK1.

The SPE-binding molecules can be polyclonal or monoclonal antibodies or fragments thereof or other binding proteins as described above. Monoclonal antibodies can be humanized or fully human antibodies and can be IgG, IgM, IgE, or other types of antibodies known to the art, and can be of subtypes 1, 2, 3, or 4.

The pharmaceutical composition can further comprise a second anti-cancer agent such as a cytotoxic agent, or can comprise micelles containing cytotoxic agents, as taught in Ghaleb, A. H. et al. (2005), "The Comet Assay to Determine the Mode of Cell Death for the Ultrasonic Delivery of Doxorubicin to Human Leukemia (HL-60 Cells) from Pluronic P105 Micelles," Technology in Cancer Research & Treatment 4(6):1-15.

In embodiments, the SPE-binding molecules are conjugated to the cytotoxic agent(s). The second anti-cancer agent can be a nucleoside analog, which can be any nucleoside analog anti-cancer agent known to the art, e.g., a nucleoside analog selected from the group consisting of: 5' fluorouracil, fludarabine, cladribine, cytarabine, gemcitabine, capecitabine, troxacitabine, zidovudine/lamivudine (Combivir®), emtricitabine (Emtriva®), emtricitabine (Epivir®), zalcitabine (Hivid®) zidovudine (Retrovir®), abacavir/zidovudine/lamivudine (Trizivir®), didanosine (Videx®, VidexEC®), tenofovir disoproxil fumarate (Viread®), stavudine (Zerit®), and abacavir (Ziagen®). In embodiments, the second anti-cancer agent is selected from the group consisting of pokeweed antiviral protein (PAP), ricin, abrin, gelonin, saporin, and alpha-sarcin.

The pharmaceutical composition can be administered by any means known to the art, and can be formulated with carriers and excipients known to the art.

In embodiments, prior to administering the pharmaceutical composition, the mammal is treated with sufficient radiation at a tumor site to up-regulate expression of said SPE(s) at said site.

Cancer cells whose proliferation can be inhibited by the methods described above include cells of cancers selected from the group consisting of lung cancer, bone cancer, pancreatic cancer, skin cancer, cancer of the head and/or neck, cutaneous or intraocular melanoma, uterine cancer, ovarian cancer, rectal cancer, cancer of the anal region, stomach cancer, colon cancer, liver cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer, and combinations thereof; and in embodiments, the cancer cells can be cells of cancers selected from the group consisting of lymphoma, breast, liver, cervical and pancreatic cancer cells.

Methods for visualizing cancer in a mammal to determine the location and extent of neoplastic tissue in a mammal are provided herein. The methods comprise: a) administering one or more labeled SPE-binding molecules that specifically bind to an SPE target selected from the group consisting of: TK1, APRT, HGPRT, dCK; combinations of any two, three or four of said SPEs; and complexes comprising any one, two, three or four of said SPEs; wherein when TK1 is the only target being tested for, the binding molecule is not an anti-TK1 antibody that binds to the C-terminal of TK1; and b) visualizing the labeled SPE-binding molecules, thereby determining the location and extent of neoplastic tissue in the mammal.

The visualization of the labeled SPE-binding molecules can be done by any means known to the art. In embodiments, the visualization is done by PET, MRI, CT, or SPECT. In embodiments, the SPE-binding molecules are labeled with a fluorescent, radioactive, or radio-opaque dye.

In embodiments the method is conducted in the context of a surgical procedure to allow the physician to visually differentiate neoplastic tissue from normal tissue.

The present disclosure also provides methods of making new anti-TK1 antibodies or other binding molecules that bind to a TK1-binding site that is not located, or partially located, on the C-terminal of TK1. A method, for making an antibody capable of binding to thymidine kinase 1 (TK1) at a binding site other than the C-terminal, comprises: a. providing a polypeptide of TK1 comprising a binding site for a TK1-binding molecule which is not on or partially on the C-terminal of TK1; and b. preparing a binding molecule that specifically binds to said polypeptide. Methods for screening binding molecules to ensure specificity to the desired binding site are known to the art. The binding molecule can be a monoclonal antibody, which can be a humanized or fully human monoclonal antibody, and which can be of any type, including IgG, IgM, IgE, or others known to the art, and of any subtype. The binding molecule can also be a polyclonal antibody such as a polyclonal antibody made in a rabbit or in a mouse, goat or human. The binding molecules can also be antibody fragments or synthetic proteins prepared by methods known to the art. The polypeptide used to make the antibodies or other binding molecules has a sequence which is, or is comprised in (i.e., is a fragment of) the sequence of SEQ ID NO:1 of human TK1 or is or is comprised in a sequence having at least 85%, 90%, 95%, 97% or 99% homology to SEQ ID NO:1.

Anti-TK1 binding molecules made by the above methods that bind specifically to TK1 at a site that is not on the C-terminal are also provided. Such antibodies can bind specifically to a binding site comprised in SEQ ID NO:1, or comprised in a sequence having at least 85%, 90%, 95%, 97% or 99% homology to SEQ ID NO:1, or can bind specifically to another binding site. These antibodies can be monoclonal or polyclonal antibodies as described above. In embodiments, the antibodies are capable of inhibiting TK1 enzymatic activity in vitro or in vivo, including in tumor tissue.

Also provided herein is an isolated polypeptide having the amino acid sequence of SEQ ID NO:1 or a sequence having at least 85%, 90%, 95%, 97% or 99% homology therewith.

Further provided herein is an isolated nucleotide molecule having a sequence encoding the polypeptide having a sequence of SEQ ID NO:1 or a polypeptide having a sequence at least 85%, 90%, 95%, 97% or 99% homology to SEQ ID NO:1. In embodiments, the isolated nucleotide sequence has the sequence: CAGTACAAGTGCCTGGTGATCAAGTATGCCAAAGACACTCGCTACAGCAGCAGCTTCT GCACACATGACCGGAACACCATGGAGGCACTGCCCGCCTGCCTGCTCCGAGACGTGGCCCAGGAGGCCCTGGGCGTGGCTGTCATAGGCATCGACGAGGGGCAGTTTTTCCC TGACATCGTGGAGTTCTGCGAGGCCATGGCCAACGCCGGGAAGACCGTAATTGTGGC TGCACTGGATGGGACCTTCCAGAGGAAGCCATTTGGGGCCATCCTGAACCTGGTGCC GCTGGCCGAGAGCGTG [SEQ ID NO:2], or has a sequence having at least 85%, 90%, 95%, 97% or 99% homology thereto.

BRIEF DESCRIPTION OF THE DRAWINGS

These and other features of the present methods, kits and compositions will now be described with reference to the drawings, which are intended to illustrate and not to limit the invention.

FIG. 10A: Western blot of an immunoprecipitation using CB001 (anti-TK1 antibody) and stained using an anti-APRT antibody. This indicates that there was a complex that was pulled down using an antibody to TK1 that can be detected using an antibody to APRT, indicating the complex contained TK1 and APRT.

FIG. 10B: Western blot of an immunoprecipitation using CB001 (anti-TK1 antibody) and stained using an anti-HGPRT antibody. This indicates that there was a complex that was pulled down using an antibody to TK1 that can be detected using an antibody to HGPRT, indicating the complex contained TK1 and HGPRT.

FIG. 10C: Western blot of an immunoprecipitation using CB001 (anti-TK1 antibody) and stained using an anti-dCK antibody. This indicates that there was a complex that was pulled down using an antibody to TK1 that can be detected using an antibody to dCK, indicating the complex contains TK1 and dCK. These results confirm that TK1, APRT, HGPRT, and dCK formed a complex that is released into the serum of cancer patients. The complex was found only in cancer serum but not in normal serum.

FIG. 23A: HT29 cells stained with a primary antibody to HGPRT, and a secondary conjugated with FITC. FIG. 23B: H460 cells stained with a primary antibody to NA+/K+ ATPase, and a secondary conjugated with FITC (positive control). FIG. 23C: H460 cells stained with an antibody to HGPRT and a secondary conjugated to FITC. FIG. 23D: H460 cells stained with an antibody to dCK and a secondary conjugated to FITC. FIG. 23E: MCF7 cells stained with an antibody to APRT and a secondary conjugated to FITC. FIG. 23F: H435 cells stained with a secondary antibody conjugated to FITC (Negative control). FIG. 23G: H435 cells stained with an antibody to APRT and a secondary conjugated to FITC. FIG. 23H: H435 cells stained with an antibody to APRT and a secondary conjugated to FITC. FIG. 23I: HT29 cells stained with an antibody to APRT and a secondary conjugated to FITC, overlaid with a 4',5-diamidino-2-phenylindole (DAPI) stain. FIG. 23J: HT29 cells stained with an antibody to dCK and a secondary conjugated to FITC, overlaid with a DAPI stain. FIG. 23K. H358 cells stained with an antibody to dCK and secondary conjugated to FIKTC. FIG. 23L. Raji cells stained with an antibody to TK1 and a secondary conjugated with FITC.

DETAILED DESCRIPTION

Figure 1:
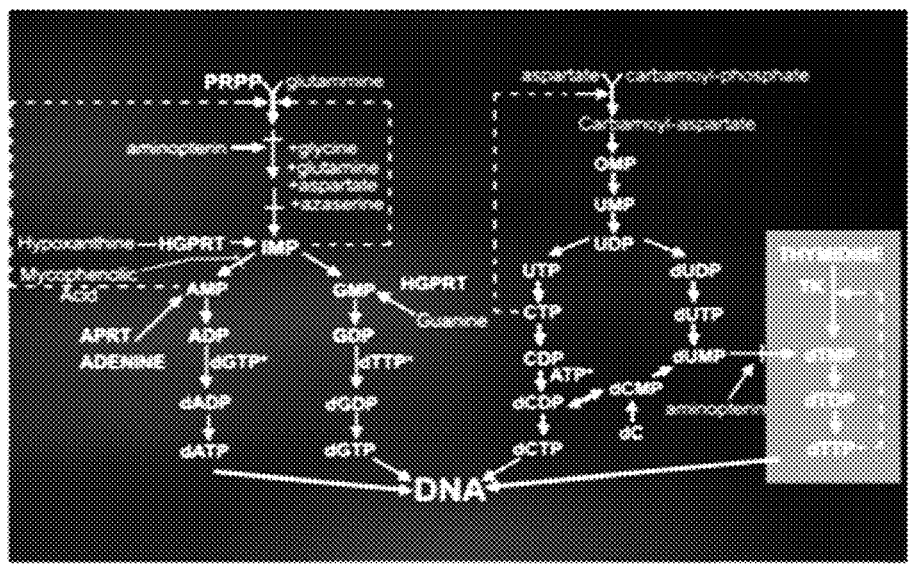
FIG. 1 provides the reactions of the four nucleotide salvage pathway enzymes APRT, HGPRT, dCK and TK1.

While certain specific descriptions are provided herein, it is to be understood that modifications will occur to those skilled in the art without departing from the spirit of the present methods, systems, kits and compositions.

TK1 levels are over-expressed in most cancers throughout the cell cycle. TK1 is linked with the p53 pathway. TK1 and other nucleotide salvage pathway enzymes (individually or in combination) are very good targets for cancer diagnosis, prognosis, and therapy. The salvage pathway enzymes including TK1 are overly expressed on the plasma membrane and inside the cancer cells, and are released into biological fluids, including but not limited to serum.

Embodiments hereof are directed to a method for treating cancer in a mammal by administering to the mammal, an amount of a pharmaceutical composition which includes an antibody or combinations of antibodies specific to one, all, or combinations of the salvage pathway enzymes, or a fragment(s) thereof, sufficient to target cancer cells and inhibit cell proliferation in the mammal. Combinations of antibodies specific to the four salvage pathway enzymes are useful in the present methods. Where the antibody is specific to TK1, the anti-TK1 antibody can be monoclonal antibody CB001, or a polyclonal or monoclonal antibody produced using a polypeptide having the sequence: QYKCLVIKY-AKDTRYSSSFCTHDRNTMEALPACLLRD-VAQEALGVAVIGIDEGQFFPDIVEF CEAMANAGK-TVIVAALDGTFQRKPFGAILNLVPLAESV [SEQ ID NO:1] or a sequence having at least 85%, 90%, 95%, 97% or 99% homology therewith, or produced using a binding sequence comprised in SEQ ID NO:1, or comprised in a sequence having at least 85%, 90%, 95%, 97% or 99% homology therewith, or fragment of said antibody capable of binding to a binding site comprised in SEQ ID NO:1 or comprised in a sequence having at least 85%, 90%, 95%, 97% or 99% homology to SEQ ID NO:1. When TK1 is the only SPE being tested for in the methods and devices hereof, an anti-TK1 antibody that specifically binds to the C-terminal of TK1 cannot be the only anti-TK1 antibody used.

APRT-specific, HGPRT-specific, and dCK-specific, antibodies are commercially available from many sources such as AbCam, Cambridge, Mass. The APRT-specific antibody can be ABCAM ab72782, or ABCAM ab91428; the HGPRT-specific antibody can be ABCAM ab55260 or ABCAM ab10479; and the dCK-specific antibody can be ABCAM ab38012 or ab83046. Other monoclonal or polyclonal antibodies specifically designed to bind different epitopes of the salvage pathway enzymes, APRT, HGPRT, and dCK, are also useful herein. Antibodies specific to complexes of any two or more salvage pathway enzymes are also useful herein, and can be produced by means known to the art using the complexes to produce antibodies and screening for antibodies that are specific to the complexes rather than to individual SPEs. Anti-TK1 antibodies are also commercially available, and an anti-TK1 antibody that binds to a different epitope from previously-known anti-TK1 antibodies is provided herein. Advantageously, the antibody(ies) is (are) produced in the same species as that being treated or tested, or the antibody is adapted to be immunologically compatible with that species, for example, a humanized antibody for use in a human. In embodiments, the anti-salvage pathway antibodies are humanized or fully human monoclonal antibodies.

Another embodiment is the treatment of cancer using a pharmaceutical composition comprising an effective amount of one or more antibodies specific to a salvage pathway enzyme selected from the group consisting of APRT, HGPRT, and dCK. Antibodies specific to all the salvage pathway enzymes or complexes containing one or more of said enzymes, (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of the foregoing are useful for the treatment of cancer. Antibodies specific to TK1 are useful for the treatments hereof in combination with one or more of the other salvage pathway enzymes. A single antibody specific to TK1 that binds to the C-terminal of TK1 by itself in a method hereof is not used.

Also encompassed herein are compositions for and methods of treatment of cancer in a mammal. Compositions useful for such treatment comprise antibody(ies) or other binding molecules specific for at least one salvage pathway enzyme (but not antibodies that bind to the C-terminal of TK1 by themselves); antibodies or other binding molecules specific to each of all four salvage pathway enzymes; or antibodies or other binding molecules specific to any combination of salvage pathway enzymes; or antibodies or other binding molecules specific to complexes containing one or more SPEs.

In embodiments, the anti-salvage pathway enzyme antibodies can be humanized antibodies or fully human monoclonal antibodies (especially for use in the human body). An embodiment hereof is the treatment of cancer using a pharmaceutical composition comprising one or more antibodies specific to all the salvage pathway enzymes or combinations of two, three or four thereof, or complexes containing one or more of said enzymes (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of any of the foregoing. Antibodies specific to TK1 that bind to the C-terminal of TK1, or to another binding site on TK1 are also useful for the purposes hereof in combination with one or more of the other salvage pathway enzymes. Methods using only a single antibody specific for TK1 that binds to the C-terminal of TK1, by itself and not in combination with antibodies that bind to other sites on TK1, are not claimed herein.

In certain embodiments, the pharmaceutical composition also includes one or more additional anti-cancer agents, for example, a nucleoside analog. The nucleoside analog can be 5' fluorouracil, fludarabine, cladribine, cytarabine, gemcitabine, capecitabine, troxacitabine, zidovudine/lamivudine (Combivir®), emtricitabine (Emtriva®), emtricitabine (Epivir®), zalcitabine (Hivid®), zidovudine (Retrovir®), abacavir/zidovudine/lamivudine (Trizivir®), didanosine (Videx®, VidexEC®), tenofovir disoproxil fumarate (Viread®), stavudine (Zerit®), abacavir (Ziagen®), or others known to the art.

In some embodiments, the salvage pathway enzyme-specific antibody(ies) are conjugated to a cytotoxic agent, including but not limited to pokeweed antiviral protein (PAP), ricin, abrin, gelonin, saporin, alpha-sarcin, or other toxin used in the art for antineoplastic treatments. This targets the toxin to the cancer cells with the salvage pathway enzyme(s) on their surfaces.

In embodiments, a method for diagnosing cancer in a mammal is provided, including the steps of obtaining a sample from the mammal; incubating the sample with at least one anti-salvage pathway enzyme antibody or fragment thereof; detecting an amount of antibody-enzyme complex; quantifying the concentration of each salvage pathway enzyme in the sample by comparing the detected amount of antibody-enzyme complex with a standard curve generated using known amounts of each of the salvage pathway enzymes or all of them together; and diagnosing the presence of cancer in the mammal based on the concentration of each or combinations of the levels of salvage pathway enzymes in the sample (when the concentration, of each enzyme or combination of enzymes, is significantly greater in the sample than in a corresponding sample from a normal subject). Antibodies specific to all the salvage pathway enzymes or complexes containing one or more of said enzymes, (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of the foregoing are useful in the method for diagnosing cancer. Antibodies specific to TK1 that bind to the C-terminal of TK1, or to another binding site on TK1 are also useful for the purposes hereof in combination with one or more of the other salvage pathway enzymes. Methods using only a single antibody specific for TK1 that binds to the C-terminal of TK1, by itself and not in combination with antibodies that bind to other sites on TK1, are not claimed herein.

Certain embodiments are directed to antibodies specifically binding to TK1, APRT, HGPRT, and dCK or complexes containing these enzymes. When the patient being evaluated is human, the salvage pathway enzymes to which the antibodies are specific are human salvage pathway enzymes. An antibody of single specificity can be used, or an antibody to a combination of anti-salvage pathway enzyme antibodies, including antibodies to combinations such as anti-TK1, anti-APRT, anti-HGPRT and/or anti-dCK. Antibodies specific to all the salvage pathway enzymes or complexes containing one or more of said enzymes (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of the foregoing are provided. Antibodies specific to TK1 that bind to a site other than the C-terminal of TK1, including a site having the sequence comprised in the sequence of SEQ ID NO:1, or comprised in a sequence having at least 85%, 90%, 95%, 97% or 99% homology to SEQ ID NO:1, are also provided herein. While single salvage pathway enzyme-specific antibodies can be used, improved sensitivity and accuracy can be achieved with a combination of antibodies, for example, antibodies to TK1 and APRT, or HGPRT and dCK.

Embodiments are directed to a method of determining location and spread of neoplastic tissue in a patient including the steps of administering a labeled antibody or antibodies specific to all the salvage pathway enzymes or combinations thereof containing antibodies specific for two or more SPEs, or to complexes containing one or more of said enzymes, (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of the foregoing to a patient; detecting and/or visualizing the labeled antibody or antibodies; and thereby determining the location and extent of spread of neoplastic tissue in the patient. In embodiments antibody specific for APRT, HGPRT or dCK can be used. Antibodies specific to TK1 that bind to the C-terminal of TK1, or to another binding site on TK1 are also useful for the purposes hereof in combination with one or more of the other salvage pathway enzymes. Methods using only a single antibody specific for TK1 that binds to the C-terminal of TK1, by itself and not in combination with antibodies that bind to other sites on TK1, are not claimed herein.

The visualization, detection, and determining the location (localization) of cancer in a patient's body can be by PET, MRI, CT, or SPECT or other detection method known to the art. The antibody or antibodies is/are labeled with a radioactive moiety or radio-opaque dye or other directly or indirectly detectable moiety, as known to the art, to enable detection, visualization, and/or localization.

Further embodiments are directed to methods for diagnosing cancer in a mammal, including the steps of: obtaining a biological sample from the mammal; optionally incubating the biological sample with a chelating agent, and/or a reducing agent and/or a detergent to allow identification of different SPEs that are complexed together, and simultaneously or subsequently, contacting the sample with an anti-salvage pathway enzyme antibody or other SPE-binding partner capable of binding specifically to the SPE or complex containing the SPE, wherein the binding partner can be an antibody, a fragment thereof, or another binding protein known to the art, to form a first complex, binding the first complex with a second anti-salvage pathway enzyme antibody or other SPE-binding partner to form a second complex, wherein the first anti-salvage pathway enzyme antibody or first binding partner thereof and the second anti-salvage pathway enzyme antibody or second binding partner thereof bind to different sites of the salvage pathway enzyme protein(s); detecting an amount of the second complex; assessing the amount of second complex in the biological sample in comparison to the amount of salvage pathway enzyme(s) in a corresponding biological sample of a normal mammal; wherein the mammal is diagnosed as being afflicted with cancer when the amount of the second complex is greater in the mammal from which the biological sample is taken than the amount of second complex in a corresponding sample from a normal mammal.

The antibody or antibodies specific to at least one salvage pathway enzyme or complex containing one of these SPEs (but, again, not a single anti-TK1 antibody that binds to the C-terminal of TK1 as the only binding partner) or all four or any sub-combination (TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; TK1, APRT, and dCK; or TK1, HGPRT, APRT and dCK) or complex containing at least one of said SPEs, can also be labeled with a detectable label and administered to a patient; followed by detecting and/or visualizing the labeled antibody or antibodies; whereby the location and extent of spread of neoplastic tissue in the patient can be determined.

In another embodiment, a method is provided for assessing the progress of cancer therapy in a mammal afflicted with cancer. A biological sample is obtained from the mammal prior to (or during cancer therapy) and the amount of SPE or SPE complex in the sample is determined, or the sample or a part thereof is retained for later analysis. During or after cancer therapy a biological sample of the same type is taken and optionally incubated with a chelating agent and/or a reducing agent and/or detergent, and simultaneously or subsequently, with a first anti-SPE or anti SPE-complex antibody or other binding molecule, to form a first complex, the first complex is detected with a second anti-SPE or anti-SPE-complex antibody or other binding molecule under conditions which allow formation of a second complex, wherein the first anti-SPE or anti SPE-complex antibody or other binding molecule and the second first anti-SPE or anti SPE-complex antibody or other binding molecule bind to different sites on an SPE protein or complex in the sample, and then an amount of the second complex is determined; allowing assessment of the amount of SPEs or complexes thereof in the biological sample in comparison to the amount of SPEs or complexes thereof in a corresponding biological sample from the same mammal at a previous time before or during treatment, wherein the progress of cancer therapy is assessed, whereby a decrease in the relative amount of second complex indicates successful therapy or wherein an increase or no change in the relative amount of the second complex indicates failure of the cancer therapy. Although one salvage pathway enzyme-specific antibody can be used, for example specific to APRT, HGPRT or dCK, or complexes containing one of these enzymes, as above, it is believed that greater sensitivity can be achieved using antibodies specific to all four salvage pathway enzymes or complexes thereof together or a sub-combination thereof (TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; TK1, APRT, and dCK, especially TK1 and APRT; or TK1, HGPRT, APRT and dCK) or complexes containing the foregoing. The greater reduction in salvage pathway enzyme(s) detected, the greater the response to the treatment. Again, methods using antibodies to TK1 that bind to the C-terminal by themselves, and not in combination with binding molecules that bind to other SPEs or other sites on TK1, are not claimed herein.

Prognosis of a mammal afflicted with cancer based on the concentration of one or more salvage pathway enzymes, especially TK1 and/or APRT in the sample can be assessed using the methods of the present disclosure in that, for example, an increase in the relative amount of the second complex can indicate progression of the cancer, with a relatively negative prognosis for the patient. The medical or veterinary practitioner can then elect to pursue a more aggressive treatment of the cancer in an attempt to improve the patient's survival and/or quality of life. Generally, the higher the level of cell surface salvage pathway enzymes and/or released salvage enzymes and/or salvage enzyme complex, the more advanced the cancer in the patient, and thus, the poorer the prognosis. As above, it is believed that greater sensitivity can be achieved using antibodies specific to all four salvage pathway enzymes together or complexes containing one or more of these enzymes, or a sub-combination thereof (TK1 and APRT; TK1 and HGPRT; TK1 and dCK; HGPRT and dCK; APRT and HGPRT; APRT and dCK; TK1, APRT, HGPRT; APRT, HGPRT and dCK; TK1, HGPRT and dCK; TK1, APRT, and dCK, especially TK1 and APRT; or TK1, HGPRT, APRT and dCK) or complexes of the foregoing. The lower the level of salvage pathway enzyme(s) detected on the cancer cell surface and/or released from cancer cells, for example, into biological fluid, the better the prognosis for the patient. Methods using antibodies to TK1 that bind to the C-terminal by themselves, and not in combination with binding molecules that bind to other SPEs or other sites on TK1, are not claimed herein.

The amount of the second antibody can be estimated using a variety of detectable signals associated with the second anti-savage pathway enzyme antibody or second SPE-binding molecule. In an embodiment, the second antibody can be conjugated with an enzyme which, when incubated with a substrate under appropriate conditions, produces a detectable, and preferably quantifiable signal. The substrate can be chromogenic, fluorogenic, chemiluminescent or other substrate known to the art that produces a detectable signal when acted upon by the enzyme. In other embodiments, the second anti-salvage pathway antibody or second binding fragment thereof can have a detectable moiety associated with it to allow detection and quantification, such as a radio-nucleotide, a fluorescent or chemiluminescent moiety, or a moiety such as biotin or a biotin-binding moiety.

The sample used in the methods described herein is a biological sample, and it can be a blood, plasma, serum, cerebrospinal fluid, urine, peritoneal exudate, saliva, lymph fluid, seminal fluid, milk, milk duct fluid, tissue homogenate, biopsy sample, or other sample taken from a mammal suspected of having a cancerous condition or from a mammal afflicted with cancer, or it can be a sample of medium in which cancer or other cells have been grown. In other embodiments the sample can be a biopsy or tissue sample or other biological material, and it can be in the form of a histological slide specimen for microscopic examination, for example, a specimen which has been contacted with an SPE-specific antibody or other SPE-binding molecule preparation as described herein, and in embodiments, after being contacted with a binding molecule which is attached to a directly or indirectly detectable signal. Such signals include a fluorescent, chemiluminescent, radioactive and other labels or chromogenic or other detectable product of an enzyme linked to a first or second antibody.

In an embodiment, the method utilizes a monoclonal (or polyclonal) antibody to a salvage pathway enzyme, for example, APRT or an APRT-binding partner thereof. Preferably, the salvage pathway enzyme is a mammalian salvage enzyme, for example a TK1, APRT, HGPRT or dCK. In embodiments the immunizing antigen (SPE or portion thereof) to which the antibody or other antigen-binding derivative is made is from the same species as the sample is from. The salvage enzyme-specific first and second antibodies or fragments thereof can be specific to an active or an inactive salvage pathway enzyme, and in embodiments, can bind both forms, including those complexed on the surfaces of cancer cells or released into biological fluids such as serum. In embodiments, antibodies can be polyclonal or monoclonal, one can be a monoclonal antibody, or in embodiments where two antibodies are used, both can be monoclonal antibodies, or both can be polyclonals. Antibodies used herein can be chimeric, humanized, or fully human monoclonal antibodies, Fab fragments, single-chain recombinant antibodies, or other antigen-binding derivatives, as is known in the art. As indicated above, it is advantageous for first and second SPE-specific antibodies to recognize different sites of the enzyme(s). Antibodies (including certain monoclonal and polyclonal antibodies) specific for TK1, HGPRT, APRT, and dCK are commercially available, and others can be made according to art-known methods. When more than one specific antibody is used, the specificities for salvage enzyme binding can be to all four or to any subcombination of the enzymes, or to complexes containing any of the enzyme(s).

An embodiment hereof relates to the detection of SPEs or SPE complexes on the surfaces of cancer cells or in the bloodstream (or samples derived from blood, such as serum samples) of a cancer patient. An immunoassay can be used to detect the SPEs or complex(es) via antibodies or other binding molecules specific for APRT, HGPRT, TK1 and/or dCK, or complexes containing any of them, or any combination of two or more antibodies specific to nucleotide salvage enzymes. In embodiments, antibody(ies) or other binding molecules specific for APRT and TK1, or for APRT alone are used. Improved results can be achieved using antibodies specific to all the SPEs or complexes containing one or more of said enzymes, or combinations of any two, three or four SPEs (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of the foregoing) are useful. Immunofluorescence, radioimmunoassay, fluorescence-activated cell sorting or enzyme-linked immunoassays can be used to detect these complexes or components thereof. If used in vitro, imaging technology as known to the art can be used to detect binding with the use of appropriate direct or indirect detection. Again, methods using antibodies to TK1 that bind to the C-terminal by themselves, and not in combination with binding molecules that bind to other SPEs or other sites on TK1, are not claimed herein.

In an improved immunoassay for salvage pathway enzyme or salvage pathway enzyme complex, for example, a sandwich immunoassay or a sandwich enzyme linked immunoassay, the biological sample is optionally treated with a chelating agent selective for divalent cations and/or a reducing agent and/or a detergent to separate enzymes from complexes containing them. The inventors' work indicates that cancer-specific complexes of proteins including the salvage pathway enzymes are present on the surface of cancer cells and are released into the extracellular environment, including, for example, into the bloodstream or other biological fluids. Antibodies specific for an SPE selected from the group consisting of APRT, HGPRT, and dCK, or complexes containing one or more of said enzymes, (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPRT; APRT, HGPRT and dCK; TK1, HGPRT and dCK; or TK1, APRT, and dCK or complexes of the foregoing are useful for the treatment of cancer. Antibodies specific to TK1 are also useful. Immunoassays containing only a single antibody specific to TK1 that binds to the C-terminal of TK1 by itself are not claimed herein.

A sandwich assay for TK1 has been developed in which polyclonal antibodies made using a polypeptide having the sequence of SEQ ID NO:1 have been used for the capture and the detection ("chase") antibodies.

Salvage pathway enzyme levels have been shown to be elevated in most forms of cancers, including but not limited to breast, colon, prostate, lung, leukemia, lymphoma, and others. Also provided herein are methods for the determination of the different stages of the patient's cancer. Salvage pathway enzyme levels in serum and other fluid samples correlate to the extent of metastasis and progression of cancer, with higher levels correlating with more severe or more advanced cancer. For example, serum samples from a patient that was classified as a "pre-leukemic" individual by the physician have been analyzed by TK1 radio-assay; the results indicated increased levels of TK1 in serum from leukemia patients compared to TK1 levels in serum of normal individuals. Such results show that the salvage pathway enzyme levels can be measured as an effective early diagnostic tool.

An ELISA comprising a capture anti-salvage pathway enzyme antibody, or binding partner of said enzyme, and a detection anti-salvage pathway antibody, or binding partner, wherein, in embodiments, the capture and detection antibodies bind to different epitopes on the salvage pathway enzyme, is also provided herein. Antibodies specific to a salvage pathway enzyme selected from the group consisting of APRT, HGPRT, and dCK are used. Antibodies specific to all the SPEs or combinations containing two, three or four of the SPEs) or complexes containing one or more of the SPEs (specific for each of TK1, APRT, HGPRT, and dCK) or antibodies specific to TK1 and APRT; TK1 and HGPRT; TK1 and dCK; HGPRT and dCK; APRT and HGPRT; APRT and dCK; TK1, APRT, and HGPR; APRT, HGPRT and dCK; TK1, HGPRT and dCK; or TK1, APRT, and dCK or complexes of the foregoing) are useful. Antibodies specific to TK1 that bind to the C-terminal of TK1 are also useful but only in combination with antibodies specific to one or more of the other salvage pathway enzymes or specific to a binding site other than the C-terminal of TK1. The use of a single antibody specific to TK1 that binds to the C-terminal of TK1 by itself is not claimed herein.

Also provided herein is an immunoassay system for detecting the levels of salvage pathway enzymes in a sample comprising: a) optional means for incubating a fluid sample from a mammal with a reducing agent and/or means for incubating the sample with the chelating agent, or means for incubating the sample with a detergent, which can be any means known to the art including wells, containers, droplets and optional fluid transfer equipment such as tubes, pipettes, and other such means known to the art, wherein the incubating means for the reducing, chelating and detergent agents can be the same or different, and when these means are different, they are in fluid communication with each other; b) a capture protein such as an antibody or other binding partner of said enzyme or of a complex comprising said enzyme that specifically binds to a first epitope of the salvage pathway enzyme to form a first antibody complex, said capture antibody or other binding partner being in fluid communication with the sample; c) a mechanism for fluid communication of the sample with the capture antibody or other binding partner to form a first antibody complex; d) a detection antibody or other binding partner to said enzyme or complex containing said enzyme, that specifically binds to a second epitope of the salvage pathway enzyme or complex containing it, which second epitope can be the same or different from the first epitope, in fluid communication with said first antibody complex; e) means for contacting the first antibody complex with a detection antibody or binding fragment thereof, such as transfer means described above and/or flow path architecture, to form a second salvage pathway enzyme complex; and f) means for detecting the second antibody or other binding molecule complex, which means can include labels that bind to the complex and can be detected by eye or by sensors such as optical and radiation sensors. Alternatively, detection can be via an antibody specific to the first antibody or to a second salvage pathway enzyme complexed with the first enzyme, or via an enzyme reaction that yields a detectable product. Antibodies to all four salvage pathway enzymes and combinations thereof, and to complexes containing one or more of these enzymes can be used in this system. Specifically excluded are systems in which TK1 is the only SPE detected, and the detection is via an anti-TK1 antibody that binds only to the C-terminal of TK1. Not all of the above elements a) through f) are required for the immunoassay system, so long as the elements include a binding molecule for one or more SPEs and means for detecting binding of the binding molecule with the SPE(s).

Further aspects, features and advantages of the present methods, kits and compositions will become apparent from the detailed description of certain embodiments, which follow.

As used herein, salvage enzymes, salvage pathway enzymes and nucleotide salvage enzymes are thymidine kinase 1 (TK1), adenine phosphoribosyl transferase (APRT), hypoxanthine guanine phosphoribosyl transferase (HGPRT), and deoxycytidine kinase (dCK), as expressed as a complex and/or individually on the surface of cancer cells or as released from cancer cells into a biological fluid, e.g., serum.

The term "purified" as used herein with respect to the SPEs refers to nucleotide salvage pathway enzymes isolated from any source, e.g., isolated from any organism including a mammal, including, but not limited to, a mammalian body organ, tissue, cell, fluid or other body component, in either normal or diseased condition, and presented in any form, for example, as a fresh or preserved specimen, such as in the form of a histological slide, a cell tissue culture, a cell line, a hybridoma, and other forms known to the art. TK1, APRT, HGPRT, or dCK prepared from a virus or virally-infected cell is also specifically included in the term TK1, APRT, HGPRT, or dCK. These salvage pathway enzymes can also be prepared by recombinant methods in an appropriate host cell or can be chemically synthesized. TK1, APRT, HGPRT, and dCK sequences are known and available to the art including sequence information for human salvage pathway enzymes. One or more of these enzymes can be detected in single form or complexed with any of the others and/or with other proteins on the surface of cancer cells. They occur individually and in a cell-free complex with each other and/or other proteins in fluids in animals, especially mammals including humans.

The term "mammal" as used herein refers to a human or other animal classified taxonomically as a mammal.

The term "body tissue" as used herein refers to any normal or diseased tissue obtained from a mammal, for example, organ tissue, biopsy tissue, tumors, etc. A body tissue can be presented in any form as a fresh or preserved (e.g., frozen) sample, a histological slide preparation, or other form known to the art.

The term "biological sample" as used herein refers to a sample from a mammal, including, but not limited to, any fluid obtained from a mammal, for example, blood, saliva, serum, seminal fluid, semen, urine, cerebrospinal fluid, tears, peritoneal fluid, and others known to the art, or it can be a liquid sample which is a homogenate, exudate or cytoplasmic sample prepared from a body organ, tissue, cell, fluid, or other body component, in either normal or diseased condition and presented in any form, for example, as a fresh or preserved specimen, including a histological slide specimen.

The term "body fluid" or "biological fluid" as used herein refers to any fluid obtained from a mammal, for example, blood, serum, urine, spinal fluid, tears, a histological slide specimen, or other fluid sample known to the art. Also encompassed within the term "biological fluid" is a conditioned culture medium from cultured cancer cells.

The terms "SPE-binding molecule," "antibody" or "immunoglobulin" are used generally to include polyclonal and monoclonal antibodies and antigen-binding fragments thereof, recombinant single chain or two chain antibodies and fragments thereof which exhibit the desired binding specificity and affinity, regardless of the source or immunoglobulin type (i.e., IgG (of any subtype), IgE, IgM, and others known to the art.). The term "antibody" referring to antibodies to TK1, HGPRT, APRT, or dCK, or any of them, or the term "anti-TK1 antibody," "anti-HGPRT antibody," "anti-APRT antibody," or "anti-dCK antibody" as used herein refers to an antibody or fragment thereof that binds to an SPE, as appropriate to the usage of the term. The term "monoclonal antibody" is used in accordance with its ordinary meaning to denote a homogenous immunoglobulin resulting from the proliferation of a single clone of cells (e.g., hybridoma cells, eukaryotic host cells transfected with DNA encoding the homogenous immunoglobulin, prokaryotic host cells transformed with DNA encoding the homogenous immunoglobulin, and others known to the art.), and which is generally characterized by heavy chains of a single class and subclass, and light chains of a single type. It is contemplated that in some applications a polyclonal antibody to a purified TK1, HGPRT, APRT, or dCK of the present methods, kits and compositions can be utilized in place of an anti-SPE monoclonal antibody herein. To inhibit the SPE enzymatic activity, the SPE-specific antibodies should bind to a site(s) necessary for catalytic activity of the enzyme(s).

The term "SPE-binding molecule" as used herein refers to a molecule such as an antibody, an antibody fragment, or other moiety known to the art that binds to TK1, APRT, HGPRT, and/or DCK, or complexes of any of them with each other or other proteins with sufficient strength to withstanding the processes described herein.

The Western blots described herein show that immunoprecipitation of a complex using one salvage pathway enzyme-specific antibody, e.g., ARPT-specific antibody, allows subsequent reaction with antibody(ies) specific to one or more of the other salvage pathway enzymes, indicating that the complex contains all four salvage pathway enzymes.

The term "therapeutic application" as used herein refers to any use of a salvage pathway enzyme, monoclonal anti-SPE antibodies, or polyclonal anti-SPE antibodies, or other binding partners for the SPEs, to target diseased tissues, wherein diseased tissue proliferation is targeted, visualized, decreased or eliminated. It is contemplated that therapeutic applications can be used in conjunction with or in isolation from other currently-known or yet-to-be discovered therapeutic applications.

The terms "chimeric, humanized immunoglobulin" and "humanized antibody" are used in their ordinary meanings and include any immunoglobulin or antibody or fragment thereof, produced at least partly in a non-human mammal, wherein at least one portion is of human origin.

The term "detectable antibody" is used herein to describe an antigen-binding protein, including a polyclonal or monoclonal antibody, or recombinant antibody (such as a single chain antibody) or an antigen-binding fragment of an antibody molecule, or other protein that binds to a target antigen such as the SPEs discussed herein, that can be detected. "Detectable" means that it is directly detectable, for example via a label such as a chemiluminescent, fluorescent, chromogenic or radionuclide or enzyme attached thereto, or that it is indirectly detectable by way of a second antibody specific to it, which second antibody is itself detectable, directly or indirectly. In embodiments, an enzyme which mediates detection is covalently bound and reacts with a subject to form a detectable product.

The terms "therapeutic agent" and "biotherapeutic agent" are used in their ordinary sense and include the use of a moiety such as a MAb, pharmaceutical, protein or peptide, nucleic acid, etc. to treat or prevent disease or other abnormality in a mammal such as a human.

As used herein, a "cancer chemotherapeutic agent" is one which is more toxic to cancer cells than to normal cells. A cancer chemotherapeutic agent can be a nucleoside analog such as 5' fluorouracil, fludarabine, cladribine, cytarabine, gemcitabine, capecitabine, troxacitabine, zidovudine/lamivudine (Combivir®), emtricitabine (Emtriva®), emtricitabine (Epivir®), zalcitabine (Hivid®), zidovudine (Retrovir®), abacavir/zidovudine/lamivudine (Trizivir®), didanosine (Videx®, VidexEC®), tenofovir disoproxil fumarate (Viread®), stavudine (Zerit®), or abacavir (Ziagen®), or others known to the art. Alternatively, the cancer chemotherapeutic agent can be a cytotoxic agent, including but not limited to pokeweed antiviral protein (PAP), ricin, abrin, gelonin, saporin, and alpha-sarcin, or other toxin used in routine treatments, especially antineoplastic treatments. In addition, the cancer chemotherapeutic agent can be a compound such as doxorubicin, daunomycin, daunorubicin, vinblastine, cis-platin and related compounds, and camptothecin, among others known to the art.

The term "complement dependent cell lysis (CDC)" as used herein refers to a system of serum proteins activated by antibody-antigen complexes, which helps eliminate selected cells by directly causing their lysis or by promoting their phagocytosis. The term "antibody-dependent cellular cytotoxicity (ADCC)" refers to a mechanism of cell-mediated immunity whereby an effector cell of the immune system actively lyses a target cell that has been bound by specific antibodies. Salvage pathway enzyme-specific antibody molecules complexed with cognate enzymes on the cancer cell surface contribute to killing of cancer cells via these mechanisms.

In the present context, salvage pathway enzymes are nucleotide salvage pathway enzymes, especially thymidine kinase (TK1), adenine phosphoribosyltransferase (APRT), hypoxanthine-guanine phosphoribosyltransferase (HGPRT), and deoxycytidine kinase (dCK).

Immunotoxins

Certain embodiments herein include the use of an immunotoxin linked to the anti-TK1 MAb and/or to a monoclonal antibody or other antibody specific to APRT, HGPRT and/or dCK. First of all, the immunotoxin should be specific and should not react with tissues that do not express the target antigen to the extent that it is detrimental to the target mammal. Pastan et al. (1986) Cell 47: 641. Binding to tissues that do not express antigen can be reduced by removal of the nonspecific natural cell-binding subunits or domains of the biotherapeutic moiety, e.g., a plant glycoprotein toxin or antiviral agent. Furthermore, because plant glycoprotein toxins contain mannose oligosaccharides that bind to cells of the reticuloendothelial system and, in some cases, also contain fucose residues that are recognized by the receptors on hepatocytes, deglycosylation of plant toxins can be required to avoid rapid clearance and potential cytotoxic effects on these cells. Secondly, the linkage of the toxin to the antibody should not substantially impair the capacity of the antibody to bind to the antigen. Third, the immunotoxin should be effectively internalized into the endosomic vesicles. Thus, toxins directed by monoclonal antibodies to surface receptors that are normally internalized can be more active than those directed toward noninternalizing cell surface molecules. Fourth, the active component of the toxin should translocate into the cytoplasm. Finally, for in vivo therapy, the linkage between the MAb and the toxin should be sufficiently stable to remain intact while the immunotoxin passes through the tissues of the mammal to its cellular site of action.

An array of toxins of bacterial and plant origin are coupled to MAbs for production of immunotoxins. The strategy is to select from nature a cytotoxic protein and then to modify the cytotoxic protein so that it will no longer indiscriminately bind and kill normal cells, but will instead kill only the cells expressing the antigen bound by the MAb. To be optimally effective, internalization of relatively small numbers of cytotoxic molecules should be lethal to target cells, as there are limited receptor sites on the cell surface for a given MAb. The toxins produced by certain bacteria and plants that inactivate cellular protein synthesis meet this criterion as, unlike most chemotherapeutic agents which act in a stoichiometric manner, they are catalytic in their lethal activity. In general, less than ten toxin molecules in the cytoplasm of a cell are sufficient to kill the cell.

Two classes of toxins that inactivate protein synthesis have been widely employed in the construction of immunotoxins. The first class consists of intact toxins, such as intact ricin, which toxins cannot be safely applied in vivo because of lethal toxicity. Other toxins include the hemitoxins. Lethally inhibiting protein synthesis in a complementary manner, hemitoxins covalently modify the ribosome such that it can no longer productively interact with elongation factor 2. This latter family of toxins includes pokeweed antiviral protein (PAP), ricin, abrin, gelonin, saporin, and alpha-sarcin. The ribosome-inactivating proteins derived from plants consist of either two chains, including a binding chain and catalytic chain (e.g., ricin), or a single catalytic chain alone (e.g., PAP or saporin).

In certain embodiments, anti-salvage pathway enzyme antibody immunotoxin constructs for use in the present method are formed by linking an effective cytotoxic or anti-cancer amount of immunotoxin molecules to anti-salvage pathway enzyme antibody(ies). For example, a reagent useful in the present methods includes one to two immunotoxin molecules per anti-salvage enzyme antibody molecule. An exemplary composition includes about a 1:1 mixture of a) one molecule of immunotoxin/molecule of anti-salvage enzyme antibody, and b) two molecules of immunotoxin/molecule of anti-salvage enzyme antibody. A composition useful in the present methods contains mainly one or two immunotoxin molecules per intact anti-salvage enzyme monoclonal antibody molecule, free anti-salvage pathway enzyme monoclonal antibody, and free immunotoxin.

The activity of an immunotoxin is initially assessed by measuring its ability to kill cells with target antigens on their surfaces. Because toxins act within the cells, receptors and other surface proteins that naturally enter cells by endocytosis usually are appropriate targets for immunotoxins, while surface proteins that are fixed on the cell surface are not. However, if several antibodies recognizing different epitopes on the same cell surface protein are available, it is useful to test them all. This is because some antibodies, e.g., by producing a conformational change in the target protein, can more efficiently induce internalization or direct intracellular routing to an appropriate location for toxin translocation. May et al., Cell Immunol., 135, 490 (1991). Also, if the receptors are efficiently internalized, an immunotoxin can be employed that does not bind as strongly to the receptor, due to the chemical modification(s) needed to prepare the immunotoxins (Willingham et al. (1987) Proc. Natl. Acad. Sci. USA 84: 2474).

Monoclonal Antibodies

Monoclonal antibodies useful in the present methods and compositions can be produced using well known hybridoma fusion techniques (G. Kohler and C. Milstein, Eur. J. Immunol., 6, 511 (1976); M. Shulman et al., Nature, 276, 269 (1978)), as well as by the methods as described in U.S. Pat. No. 5,698,409, which is incorporated herein by reference. Embodiments of the methods, kits and compositions use one or more monoclonal antibodies directed against TK1, APRT, HGPRT and/or dCK, and/or complexes of any of them with each other or with other proteins. U.S. Pat. No. 5,698,409 describes a purified mammalian thymidine kinase 1 (TK1) from Raji cells. Raji cells are an immortalized human lymphoma cell line, available from ATCC as cell line #CCL-86. U.S. Pat. No. 5,698,409 also describes a monoclonal antibody to TK1. Methods are also known for the isolation of APRT, HGPRT and dCK. One or more of TK1-specific antibody or other SPE-specific antibody(ies) can be used in immunoaffinity methods for isolating an SPE complex from the cell surface of cancer cells, from spent medium from cultured cancer cells or serum of cancer patients, for example.

The SPE protein(s) can also be prepared by chemical synthesis of all or part of a published protein sequence. For example, the protein sequence for human TK1 has been determined from the full length cDNA (MGC Program Team, 2002, PNAS 99(26):16899-16903). The published protein sequence can be used to generate peptides that include all or part of the complete target protein. These peptides can then be used to generate MAbs by means as described herein.

Alternatively, the SPEs can be produced recombinantly using its coding sequence. The protein sequence for human TK1 are found in the Genbank database (http://www.ncbi.nlm.nih.gov/protein), as, for example, Accession No. NP_003249.3. The protein sequence for human APRT is found the Genbank database as, for example, Accession No. P07741.2. HGPRT is found in Genbank database as, for example, Accession No. P00492.2. In some embodiments, it is preferred to humanize the salvage enzyme-specific MAb. The humanized antibody can comprise portions derived from an immunoglobulin of nonhuman origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin herein is an immunoglobulin containing one or more immunoglobulin chains comprising a CDR (complementarity determining region) of nonhuman origin (e.g., one or more CDRs derived from an antibody of nonhuman origin) and a framework region derived from a light and/or heavy chain of human origin (e.g., CDR-grafted antibodies with or without framework changes). Chimeric or CDR-grafted single chain antibodies are also encompassed by the term humanized immunoglobulin.

Also included herein are humanized antibodies which have been veneered or reshaped. For example, the rodent variable region is compared to the consensus sequence of the protein sequence subgroup to which it belongs and the selected human constant region accepting-framework is compared with its family consensus sequence. Idiosyncratic residues are replaced by more commonly occurring human residues.

Such humanized immunoglobulins can be produced using synthetic and/or recombinant nucleic acids to prepare genes encoding the desired humanized chain. For example, nucleic acid sequences coding for humanized variable regions can be constructed using polymerase chain reaction (PCR) mutagenesis methods to alter DNA sequences encoding a human or humanized chain, such as a DNA template from a previously humanized variable region (see e.g., Kamman et al. (1989) Nucl. Acids Res. 17: 5404; Sato et al. (1993) Cancer Research 53: 851-856; Daugherty et al. (1991) Nucleic Acids Res. 19(9): 2471-2476 (1991); and Lewis and Crowe (1991) Gene 101: 297-302). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213; Knappik et al., WO 97/08320).

Alternatively, humanized antibodies can be conveniently prepared by injection of purified salvage pathway enzyme into SCID (severe combined immunodeficiency) mice or other SCID animal which has accepted xenografts of adult human peripheral blood leukocytes as described in U.S. Pat. No. 5,476,996, which is incorporated herein by reference in its entirety. By this treatment, human immune function is introduced into the SCID animal which can be used to produce humanized antibodies.

Monoclonal antibodies (MAbs) are produced by the fusion of spleen lymphocytes with malignant cells (myelomas) of bone marrow primary tumors. Milstein (1980) Sci. Am. 243: 66. The procedure yields a hybrid cell line, or hybridoma, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen can be distinct from each other depending on the determinant that induced their formation. However, all of the antibodies produced by a given clone are identical. Furthermore, hybridoma cell lines can be reproduced indefinitely, are easily propagated in vitro and in vivo, and can yield monoclonal antibodies in extremely high concentrations. Spleen lymphocytes are desirably obtained for use in fusions after stimulation of the immune system with an antigen of interest, especially a nucleotide salvage enzyme of a cancer cell, especially on the cancer cell surface.

Modes of Administration and Dosage of Anti-Salvage Pathway Enzyme MAb or Anti-Salvage Pathway Enzyme Antibody-Immunotoxins The dosage of the antibodies hereof in the compositions hereof can be varied widely, in accord with the size, age and condition of the mammal and the disease. Dosages are administered with a frequency based on the plasma half-life of the antibodies in a given patient. Higher doses can be employed in some cases, and the doses can readily be adjusted to provide appropriate amounts of the antibodies to children.

The anti-salvage pathway enzyme MAb or anti-salvage pathway enzyme antibody-immunotoxin hereof, or a combination thereof, can be formulated as a pharmaceutical composition and administered to a human or other mammal with cancer, preferably as a unit dosage form comprising an effective amount of one or more of the anti-salvage pathway enzyme MAb or anti-salvage pathway enzyme antibody immunotoxin in combination with a pharmaceutically acceptable carrier or vehicle, and/or in combination with other therapeutic agents.

The anti-salvage pathway enzyme antibody or other salvage enzyme specific antibody immunotoxin can be parenterally administered, i.e., intravenously, or subcutaneously by infusion or injection. Solutions or suspensions of the biotherapeutic agent can be prepared in water, or a physiological salt solution such as isotonic saline or PBS, optionally mixed with a nontoxic surfactant. However, as apparent to the health practitioner, other delivery methods can be used, including but not limited to topical, mucosal, intratumoral or inhalation methods.

Although the anti-salvage pathway enzyme MAb, or other nucleotide salvage pathway enzyme-specific antibody biotherapeutic agent can be administered as a liquid composition as described herein, it can be administered with a variety of other carriers. For example, dispersions can also be prepared in glycerol, liquid polyethylene glycols, DMA, vegetable oils, triacetin, and mixtures thereof. These preparations can also contain a preservative to prevent the growth of microorganisms. Additionally, more specific delivery of the anti-salvage pathway enzyme MAb or anti-salvage pathway enzyme antibody biotherapeutic agent to the lungs can be accomplished via aerosol delivery systems.

The compositions suitable for injection or infusion can include sterile aqueous solutions or dispersions or sterile powders comprising the anti-salvage pathway enzyme MAb or other salvage enzyme specific antibody biotherapeutic agent which are adapted for the extemporaneous preparation of sterile injectable or infusible solutions or dispersions. In all cases, the ultimate composition should be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusible solutions are prepared by incorporating the anti-salvage pathway enzyme MAb, other anti-salvage pathway enzyme antibody or other salvage enzyme specific antibody biotherapeutic agent in the required amount in the appropriate solvent with various of the other ingredients enumerated above, and as required, followed by filter sterilization. In the case of sterile powders for the preparation of sterile injectable or infusible solutions, the preferred methods of preparation are vacuum drying and the freeze drying techniques, which yield a powder of the active ingredient plus any additional desired ingredient present in the previously sterile-filtered solutions.

Suitable formulations for the anti-salvage pathway enzyme MAb, anti-salvage pathway enzyme antibody or other salvage pathway enzyme specific biotherapeutic agent include those suitable for oral, rectal, nasal, topical (including, ocular, and sublingual) or vaginal administration or in a form suitable for administration by inhalation or insufflation. The formulations can be prepared by any of the methods known in the art of pharmacy. Such methods include the step of bringing into association the biotherapeutic agent with liquid carriers or finely divided solid carriers or both and then, if necessary, shaping the product into the desired formulation. The biotherapeutic agents hereof can also be formulated for intranasal or ocular administration. In this form of administration, the active ingredients can be used as a liquid spray or dispersible powder or in the form of drops. Drops, for example, eye drops, can be formulated with an aqueous or non-aqueous base also comprising one or more dispersing agents, solubilizing agents or suspending agents. Liquid sprays are conveniently delivered from pressurized packs. In certain embodiments, the pharmaceutical composition also includes a pharmaceutically acceptable liquid carrier adapted for parenteral administration; for example, the liquid carrier can be isotonic saline. Alternatively, the administration can be oral, topical, mucosal, via inhalation or other means known to the art.

For administration by inhalation, a biotherapeutic agent as provided herein is conveniently delivered from an insufflator, nebulizer or a pressurized pack or other convenient means of delivering an aerosol spray. Pressurized packs can comprise a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount.

Alternatively, for administration by inhalation of insufflation, the biotherapeutic agent can take the form of a dry powder composition, for example, a powder mix of the compound or a suitable powder base such as lactose or starch. The powder composition can be presented in unit dosage form in, for example, capsules or cartridge or e.g., gelatin or blister packs from which the powder can be administered with the aid of an inhaler or insufflator.

The antibodies specific to anti-salvage pathway enzymes and complexes containing any of them, are well suited to formulation in controlled release dosage forms. The formulations can be so constituted that they release the active dry ingredient only or preferably in a particular physiological location, optionally over a period of time. The coatings, envelopes, and protective matrices can be made, for example, from polymeric substances or waxes. The compositions can also be delivered via patches for transdermal delivery, subcutaneous implants, infusion pumps or via release from implanted depot sustained release dosage forms.

The dosage of the antibodies hereof in the compositions hereof can be varied widely, in accord with the size, age and condition of the mammal and the disease. Dosages are administered with a frequency based on the plasma half-life of the antibodies in a given patient. Higher doses can be employed in some cases, and the doses can readily be adjusted to provide appropriate amounts of the antibodies to children.

Utilizing Salvage Enzyme Specific Antibody(ies) to Target and Destroy Cancerous Cells A variety of therapeutic applications are enabled based on the knowledge that TK1 and other salvage pathway enzymes are found on the surface of cancerous cells. An anti-cancer drug can selectively target and kill cells expressing TK1 (and/or one or more of APRT, HGPRT and dCK) on the cell surface. This embodiment is exemplified by the therapeutic application of anti-salvage pathway enzyme antibodies and/or other SPE-binding molecules, which can comprise anti-SPE antibodies or other SPE-binding molecules coupled with anti-tumor agents. An anti-tumor agent is coupled to the anti-salvage pathway enzyme antibody, which enhances the cytotoxic effects of the anti-salvage pathway enzyme antibody, and thus the killing of tumor cells relative to the killing of normal cells.

Therapeutic Site-Directed Surgery

Another therapeutic application contemplated herein is the use of anti-TK1 or other salvage enzyme specific antibody(ies) to facilitate site-directed surgery. Dye and isotope-directed surgeries are techniques known to those skilled in the art. Because salvage enzyme specific antibody(ies) adhere to the surface of cancerous cells, anti-salvage pathway enzyme-specific antibodies can be used to clearly mark cancerous tissues so that the malignant tissues can be identified, visually or otherwise, by a surgeon who can then excise or destroy the tissue utilizing minimally invasive surgical techniques. An appropriate dye is attached to the anti-salvage pathway enzyme MAb. For example, anti-salvage pathway enzyme antibodies are labeled with PET isotopes ($^{18}$F, $^{124}$I, or $^{76}$Br) or a radio-opaque dye, e.g., an iodine compound, barium or barium sulfate or gastrografin and others known to the art.

Diagnosis and Prognosis

Injectable anti-SPE antibodies and other SPE-binding molecules can be used in diagnostic and prognostic applications. In one embodiment, anti-salvage pathway enzyme specific antibodies tagged to a radioactive or a radio-opaque dye are injected into the patient. After the antibody has bound neoplastic tissue, it is visualized using well known techniques such as PET, MRI, CT, SPECT, and others known to the art (see for example, Sharma et al. (2002) J. Magnetic Resonance Imaging 16:336-351). The location and extent of spread of the disease facilitates medical diagnosis and prognosis of cancer type, location, and stage.

Kits which Utilize Monoclonal Antibodies for Therapeutic Purposes

Further provided herein are methods and kits for performing methods for detecting cancer cell surface and/or released salvage pathway enzymes and their complexes or for treating cancer. A kit for performing the above methods can comprise one or more salvage enzyme specific antibodies. In an embodiment, the monoclonal antibody is conjugated with or packaged in conjunction with other agents, for example immunotoxins or commercially available complement, that when used has therapeutic effects on the intended patients.

The subjects of this disclosure can be further understood by the non-limiting examples which follow.

EXAMPLES

Materials and Methods

Cell Culture: Myeloblastic cells derived from promyelocytic leukemia (HL-60), T-cell leukemia (Jurkat), lymphoblastoid cells derived from Burkitt's lymphoma (Raji), normal lymphocytes from healthy individuals, spindle shaped cells previously described as derived from ductal carcinoma (MDA-MB-435), lung adenocarcinoma (NCI-H23), lung carcinoma (NCI-H460), tumorigenic epithelial cells derived from colorectal adenocarcinoma (SW620), breast adenocarcinoma (MDA-MB-231), malignant melanoma (A375), oral adenosquamous carcinoma (CAL 27), prostate adenocarinoma (PC-3), prostate carcinoma (DU 145) and hepatocellular carcinoma (HepG2) cells were cultured in accordance to guidelines set forth by American Type Culture Collection (ATCC), and prepared for a flow-cell cytometry assay using antibody staining for each of the salvage pathway enzymes.

Cell Culture: malignant melanoma cells (A-375), oral adenosquamous carcinoma cells (CAL27), spindle-shaped cells previously described as derived from ductal carcinoma (MDA-MB-435S), breast adenocarcinoma cells (MDA-MB-231 and MCF7), lung carcinoma cells (A549), lung adenocarcinoma cells (NCI-H23), non-small cell bronchioalveolar carcinoma cells (NCI-H358), large-cell lung carcinoma cells (NCI-H460), prostate carcinoma cells (DU 145), prostate adenocarcinoma cells (PC-3), tumorigenic epithelial cells derived from colorectal adenocarcinoma (SW620), myeloblastic cells derived from promyelocytic leukemia (HL-60), T-cell leukemia cells (Jurkat), lymphoblastoid cells derived from Burkitt's lymphoma (Raji), esophageal adenocarcinoma cells (OE33), cervical adenocarcinoma cells (HeLa), and hepatocellular carcinoma cells (Hep G2) were cultured in accordance to guidelines set forth by American Type Culture Collection (ATCC), and prepared for a flow-cell cytometry assay using antibody staining for each of the salvage pathway enzymes.

A Flow Cytometry assay was performed as follows: for cancer cells that grow in suspension, [samples of $1\times10^6$ unpermeabilized] cells in exponential growth phase were centrifuged at 210 550 g for 20 15 min at 25° C. and then collected and re-suspended in PBS at ~7.2 pH and 4° C. (wash buffer). Samples of $1\times10^6$ unpermeabilized cells were placed in 1.5 1.7 ml tubes. For adherent cancer cell lines, the cells were first washed with sterile PBS to remove excess media. The cells were either disassociated from the wall of the flask by scraping, the use of trypsin, or a non-enzymatic cell disassociation solution. The cells were then centrifuged and resuspended so that samples of $1\times10^6$ unpermeabilized cells could be placed in 1.7 mL tubes. Samples were then washed. All washes were carried out by adding 1 mL wash buffer to each sample, centrifuging the sample at 210 420 g. for 15 min at 4° C., and decanting the supernatant. Samples were then resuspended in 100 μL of PBS and incubated at 4° C. for 10 min with 10 μl of human FcR blocking reagent (MACS Miltenyi Biotec, Bergisch Gladbach, Germany) to eliminate non-specific binding to Fc receptors. Cells were then incubated with 2 μg of the primary antibody for 12 min at 4° C. and then washed to eliminate excess antibody. The primary antibodies used were an anti-TK1 mouse monoclonal antibody known as CB001, an anti-TK1 rabbit polyclonal antibody purchased from Bethyl Laboratories (Montgomery Tex.) an anti-APRT rabbit polyclonal purchased from Abcam (Cambridge, Mass.), an anti-HGPRT rabbit polyclonal also purchased from Abcam, and an anti-dCK rabbit polyclonal purchased from Abcam. After centrifuging and decanting the supernatant, each sample was re-suspended in [re-suspension of each sample in] 100 μL of PBS. Cells were incubated with the secondary antibody goat anti-mouse or goat anti-rabbit conjugated to fluorescein isothiocyanate (FITC) purchased from Sigma Aldrich (St. Louis, Mo.) for 12 min at 4 degrees C. and then washed. The samples were then centrifuged, decanted and re-suspended in 250 μL of PBS and analyzed using flow cytometry for cell surface staining. Permeableized cells were excluded using propidium iodide staining (PI).

Raji Extract: Raji extract was obtained, by growing and harvesting Raji cells during the exponential phase of growth (~1.5 million cells per ml) with 95% viability. Cells were centrifuged at 550×g for 12 minutes. The cell pellet was re-suspended in 500 μl of Tris-HCl (7.8 pH). Then the samples were preserved by freezing at −20° C. Samples were thawed, homogenized and aliquoted into 1.5 ml eppendorf tubes by placing 800 μl in each tube. Samples were then frozen and thawed quickly 3 times using liquid nitrogen and a water bath set at 37° C. The samples were centrifuged at 12,000 rpm for 1 hr, and the supernatants were collected and analyzed.

Normal and Cancer Serum

Serum samples were obtained from patients diagnosed with cancer before, during, and after treatment. Serum samples were also obtained from normal non-cancer patients as controls. Samples were obtained with appropriate institutional approval and informed consent.

Co-Immunoprecipitation and Western Blot Analyses

Co-Immunoprecipitation assays (IP) were carried out using cancer serum samples with an Invitrogen Immunoprecipitation kit and antibodies to the different salvage pathway enzymes for each serum sample. Western blotting using these IP samples were run to see protein associations between different salvage pathway enzymes.

ELISA

An ELISA was performed on the samples, taking care to observe the following procedures: Work was done in a 96-well flat bottom with lid tissue culture plate. High-Bind plates from Greiner (Kaysville, Utah) were used. When pipetting the reagents into the plate care was taken not to scrape the bottom with the pipette tip, rather the reagents were allowed to fall into each plate without touching the plate with the tip. PBS was prepared with the following reagents: 128 g of NaCl, 3.2 g of KCl, 23.04 g of $Na_2HPO_4$, 3.84 g of $KH_2PO_4$. The reagents were mixed in approximately 3 L of distilled $H_2O$ and stirred until dissolved, then the plate was filled with distilled $H_2O$ until to a total volume of 16 L. The pH was then adjusted to 7.4 using HCl. The materials were refrigerated, rather than being stored at room temperature.

For the ELISA, a 96-well plate was coated with 10 μg antibody/ml PBS of the antibody known as "Buster." Buster is a polyclonal antibody made in a rabbit using amino acid SEQ ID NO:1. The antibody was unconjugated, 50 μl of the solution was used per well. The plate was incubated overnight (12 hrs+) at 4 degrees C. A plate sealer was used, and removed after the overnight incubation. The plate was flicked to remove the capture antibody and then three washes were performed with PBS by filling each well using a squirt bottle and then flicking to dump PBS. The 96-well plate was coated with 300 μl of freshly prepared block solution (4% BSA in Protein-free T20 Blocking Buffer from Thermo Scientific) and incubated for 1 hr at room temperature. During the last 10 minutes of the block incubation, the serum samples were readied by thawing them and diluting them appropriately. After flicking the plate to remove the block solution from the 96-well plate, three washes with PBS by filling each well were performed using a squirt bottle and then the plates were flicked to dump PBS.

50 μl of undiluted serum was placed into the plates or appropriate dilutions (in Block solution). 50 μl of Raji Extract was used for a positive control, and 50 μl of block solution was used as a negative control. The underside of the plates were tapped slightly against the countertop to ensure equal distribution of the sample on the bottom of the wells. The plates were then left to incubate at room temperature for 1 hr. About 10 min. before incubation was finished the 1:500 primary antibody solutions were prepared by diluting the antibody it in the block solution. After the 1 hr incubation with serum samples, four washes with PBS were performed as described above.

50 μl of primary antibody 1:500 solution was placed in each well. A 1:500 antibody solution was prepared by diluting 2 μl of primary antibody into 1 ml of block solution. The plates were left to incubate for 1 hr at room temperature. About 10 min. before the incubation was finished 1:1000 solutions of secondary antibody (typically goat anti-rabbit HRP conjugated antibody) were prepared in block solution. After the 1 hr incubation with the primary antibody solutions, five washes with PBS were performed as described above. 50 μl of 1:1000 secondary antibody solutions was placed in each well, and the plates were left to incubate for 1 hr at room temperature. 5 min. before the incubation was finished tetramethylbenzidine (TMB) substrate solution was prepared by placing the appropriate amount of TMB (Promega TMB One Solution Cat. #G7431) in a conical vial. The TMB was taken from a reservoir so a multipipetter could be used.

After the 1 hr incubation with the secondary antibody, five washes with PBS were performed as described above. A multipipetter was used for the next step because it is time-sensitive. 50 μl of TMB substrate solution was placed into the 96-well plate and allowed to incubate for 30 min. it reacts with horseradish peroxidase (HRP), turning the solution blue. Immediately after the incubation with TMB, the reaction was quenched with 50 μl of 1 M Phosphoric Acid ($H_3PO_4$). This stopped the reaction and turned it yellow. The plates were read at 450 nm using absorbance in a typical plate reader. To measure for one of the four SPEs, a capture antibody specific to the SPE desired is used, followed by a primary antibody specific to TK1, such as Buster, is used.

Raji Cells were grown to a very confluent state (~1.5 million cells per ml), changing the media 24 hours before extraction, achieving ~95% viability. The cells (50 ml of cells) were centrifuged at 1800 rpm for 12 min. The supernatant was removed, making sure to get rid of all the supernatant by rolling a Kimwipe and carefully absorbing any supernatant left in the conical vial, and making sure not to touch the pellet with the Kimwipe. 500 µl of tris HCl that previously adjusted to a pH of 7.80 was added and the cells were frozen for preservation at −20 degrees C. The preserved pellets, were mixed by thawing them and then aspirating them up and down. All the unlysed extract was combined into a large conical vial and aliquotted into 1.5 eppendorf tubes by placing 800 µl of unlysed extract into each eppendorf tube. The tubes were frozen and thawed 3 times by placing the eppendorf tubes in liquid nitrogen and then thawing them in the water bath at 37 degrees C. After thawing the extract was vortexed well before re-freezing with liquid nitrogen. After the third freeze/thaw cycle, the extracted was thoroughly vortexed and centrifuged at 12,000 rpm for 1 hour in a small least 4 experimental runs. The fact that TK1 is present in high percentages on the surface of cancer cells and not on normal cells suggests that it can be used as a target for cancer therapy.

Table 1 shows all the average SPE binding for all the cell lines tested, with P values, using normal lymphocytes as the control population. This clearly shows the significance of the elevation of the SPEs. This table demonstrates that even when normal lymphocytes are stimulated to divide they do not express large quantities of the SPEs on their cell surface when compared to cancer cells. The protein complex association was investigated using Western Blotting fluorescent microscopy immunohistochemistry and the 'Sandwich ELISA' described herein.

TABLE 1

Average SPE binding, all cell lines, normal lymphocyte control

| Cell Line | TK binding | n= | p= | APRT Binding | n= | p= | HGPRT binding | n= | p= | dCK binding | n= | p= |
|---|---|---|---|---|---|---|---|---|---|---|---|---|
| Normal Lymphocytes | 16.4 | 3 | n/a | 2.8 | 4 | n/a | 2.4 | 4 | n/a | 3.7 | 4 | n/a |
| Stimulated Lymphocytes | 16.6 | 7 | 0.3765026 | 7.7 | 4 | 0.2182047 | 2.9 | 4 | 0.5322583 | 3.8 | 4 | 0.90530968 |
| A-375 | 85.7 | 5 | 1.099E−05 | 82.5 | 4 | 0.0008976 | 7.1 | 5 | 0.0138219 | 41.4 | 4 | 0.00103475 |
| CAL27 | 91.1 | 5 | 2.129E−05 | 85.6 | 3 | 6.384E−05 | 20.9 | 3 | 0.0361869 | 41.3 | 4 | 0.00158377 |
| MDA-MB-435S | 78.3 | 6 | 9.288E−06 | 90.9 | 6 | 1.38E−09 | 14.7 | 6 | 0.0034532 | 21.3 | 4 | 0.01371382 |
| MDA-MB-231 | 65.6 | 3 | 0.0029203 | 83.2 | 2 | 0.0455074 | 20.6 | 2 | 0.0771782 | 33.7 | 2 | 0.06540404 |
| MCF7 | 74.2 | 1 | 0 | 76.2 | 1 | 0 | 45.9 | 1 | 0 | 55.8 | 1 | 0 |
| A549 | 78.6 | 4 | 0.0006131 | 89.5 | 4 | 0.0002182 | 40.2 | 4 | 0.0163838 | 16.8 | 3 | 0.1126427 |
| NCI-H23 | 60.7 | 4 | 0.0002732 | 82.9 | 3 | 0.0007304 | 17.7 | 2 | 0.1008188 | 34.9 | 2 | 0.01464973 |
| NCI-H358 | 63.8 | 3 | 0.0012836 | 89.9 | 4 | 7.374E−05 | 32.9 | 3 | 0.0477256 | 45.9 | 3 | 0.00434016 |
| NCI-H460 | 93.9 | 6 | 0.00061 | 97.4 | 5 | 1.34E−10 | 20.2 | 4 | 0.0067685 | 69.2 | 3 | 0.01263248 |
| DU 145 | 85 | 2 | 0.1085602 | 79.4 | 3 | 0.0066512 | 21.9 | 2 | 0.0998879 | 25 | 2 | 0.28024812 |
| PC3 | 49.6 | 6 | 0.000407 | 38.9 | 3 | 0.022646 | 22.2 | 3 | 0.0460461 | 43.8 | 3 | 0.04406085 |
| SW620 | 60.6 | 4 | 0.0008851 | 7.4 | 4 | 0.0023661 | 7.3 | 4 | 0.037737 | 33.2 | 6 | 8.1978E−05 |
| HL-60 | 94.3 | 14 | 0.0004507 | 58.6 | 2 | 0.1502517 | 66.3 | 2 | 0.1368011 | 75.2 | 2 | 0.14513011 |
| Jurkat | 92 | 23 | 0.0008501 | 47.4 | 3 | 0.0400784 | 45.1 | 3 | 0.0199999 | 44.7 | 3 | 0.0039878 |
| Raji | 97.5 | 19 | 0.0010497 | 87.2 | 4 | 0.0003143 | 83.5 | 4 | 0.0003374 | 85.5 | 4 | 0.00025528 |
| OE33 | 81.6 | 1 | 0 | 82.9 | 1 | 0 | 36.3 | 1 | 0 | 35.7 | 1 | 0 |
| HeLa | 32 | 2 | 0.0270334 | 34.2 | 2 | 0.0667978 | 10.5 | 2 | 0.0861392 | 13.2 | 2 | 0.14852355 |
| Hep G2 | 48.8 | 1 | 0 | 10.7 | 1 | 0 | 15.4 | 1 | 0 | 35.3 | 1 | 0 | centrifuge. The supernatant, which is the raji extract, was then collected with a pipette and placed in a 50 ml conical vial. All the supernatants in the 50 ml conical vial were combined so the raji extract became uniform, then aliquotted into 1.5 ml eppendorf tubes and preserved at −20 degrees C.

Normal Lymphocytes for Flow Cytometry Test

Normal lymphocytes were obtained from whole blood from volunteer subjects. Leukocytes and monocytes were separated using centrifugation through Lymphocyte Separation Media (LSM). Blood was collected and diluted at a 1:1 ratio with Hanks solution. Then the blood and Hanks dilution was carefully pipetted onto LSM and then centrifuged for 15 minutes at 550×g. Then the lymphocytes were collected and prepared for flow cytometry analysis.

Results and Discussion

Results obtained demonstrate significantly elevated staining of the salvage pathway enzymes on the surface of cancer cells and negligible staining on the surface of normal lymphocytes. This indicates therapeutic intervention is accomplished by specifically targeting the salvage pathway enzymes on the surface of cancer cells. For example, flow cytometry analysis of staining with anti-APRT-specific and anti-TK1-specific antibodies indicate the mean binding on the surface of Raji cells were 88.9% and 73.7%, respectively.

Figure 2:
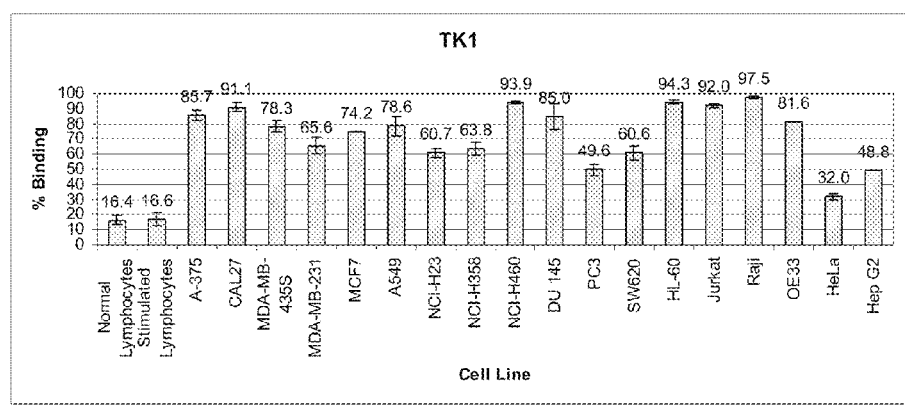
FIG. 2 shows the composite results of repeated flow cytometry experiments to evaluate anti-TK1 binding on the surface of normal lymphocytes, lymphocytes stimulated with phytohaemaglutinin (PHA), malignant melanoma cells (A-375), oral adenosquamous carcinoma cells (CAL27), spindle-shaped cells previously described as derived from ductal carcinoma (MDA-MB-435S), breast adenocarcinoma cells (MDA-MB-231 and MCF7), lung carcinoma cells (A549), lung adenocarcinoma cells (NCI-H23), non-small cell bronchioalveolar carcinoma cells (NCI-H358), large-cell lung carcinomacells (NCI-H460), prostate carcinoma cells (DU 145), prostate adenocarcinoma cells (PC-3), tumorigenic epithelial cells derived from colorectal adenocarcinoma (SW620), myeloblastic cells derived from promyelocytic leukemia (HL-60), T-cell leukemia cells (Jurkat), lymphoblastoid cells derived from Burkitt's lymphoma (Raji), esophageal adenocarcinoma cells (OE33), cervical adenocarcinoma cells (HeLa), and hepatocellular carcinoma cells (Hep G2). In this example, TK1 was stained using a rabbit polyclonal antibody specific to TK1 from Bethyl Labs. In all cases, the cancer cell lines stained from 32.0% to 95.7% whereas the normal controls showed surface cell staining of 16.4% to 16.6% ($p<0.05$). The antibodies only bind when the salvage pathway enzyme is associated with the plasma membrane.
Figure 3:
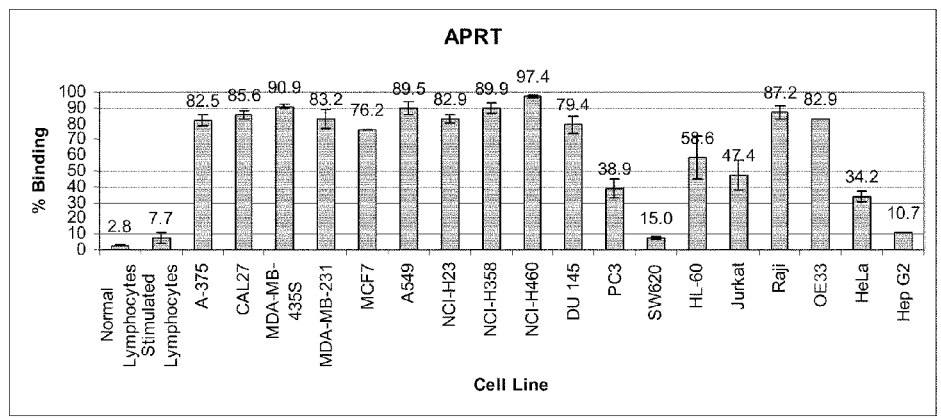
FIG. 3 shows the composite results of repeated flow cytometry experiments to evaluate anti-APRT binding on the surface of normal lymphocytes, lymphocytes stimulated with PHA, malignant melanoma cells (A-375), oral adenosquamous carcinoma cells (CAL27), spindle-shaped cells previously described as derived from ductal carcinoma (MDA-MB-435S), breast adenocarcinoma cells (MDA-MB-231 and MCF7), lung carcinoma cells (A549), lung adenocarcinoma cells (NCI-H23), non-small cell bronchioalveolar carcinoma cells (NCI-H358), large-cell lung carcinoma cells (NCI-H460), prostate carcinoma cells (DU 145), prostate adenocarcinoma cells (PC-3), tumorigenic epithelial cells derived from colorectal adenocarcinoma (SW620), myeloblastic cells derived from promyelocytic leukemia (HL-60), T-cell leukemia cells (Jurkat), lymphoblastoid cells derived from Burkitt's lymphoma (Raji), esophageal adenocarcinoma cells (OE33), cervical adenocarcinoma cells (HeLa), and hepatocellular carcinoma cells (Hep G2). In this example, TK1 was stained using a rabbit polyclonal antibody from Abcam. In all but two cancer cell lines, APRT stained from 34.2% to 97.4% whereas the normal controls showed surface cell staining of 2.8% to 7.7%. The two cancer cell lines with the lowest APRT staining still showed statistically significant elevation compared to normal controls (p<0.05). The antibodies only bind when the salvage pathway enzyme is associated with the plasma membrane.
Figure 4:
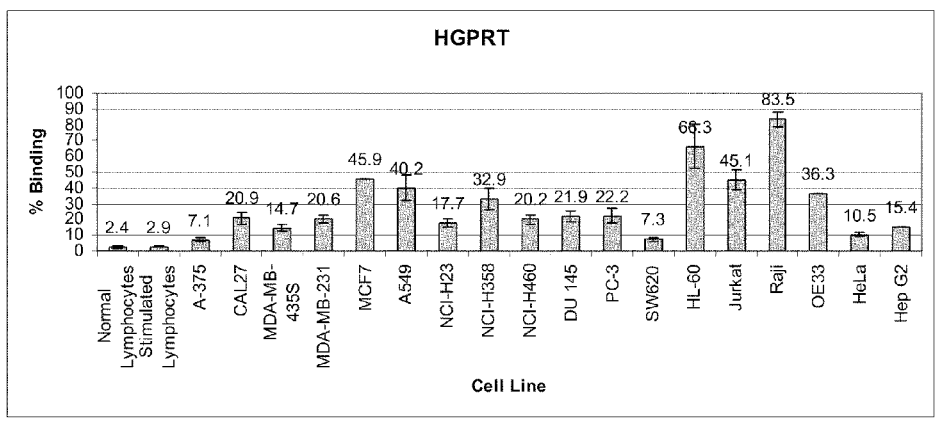
FIG. 4 shows the composite results of repeated flow cytometry experiments to evaluate anti-HGPRT binding on the surface of normal lymphocytes, lymphocytes stimulated with PHA, malignant melanoma cells (A-375), oral adenosquamous carcinoma cells (CAL27), spindle-shaped cells previously described as derived from ductal carcinoma (MDA-MB-435S), breast adenocarcinoma cells (MDA-MB-231 and MCF7), lung carcinoma cells (A549), lung adenocarcinoma cells (NCI-H23), non-small cell bronchioalveolar carcinoma cells (NCI-H358), large-cell lung carcinoma cells (NCI-H460), prostate carcinoma cells (DU 145), prostate adenocarcinoma cells (PC-3), tumorigenic epithelial cells derived from colorectal adenocarcinoma (SW620), myeloblastic cells derived from promyelocytic leukemia (HL-60), T-cell leukemia cells (Jurkat), lymphoblastoid cells derived from Burkitt's lymphoma (Raji), esophageal adenocarcinoma cells (OE33), cervical adenocarcinoma cells (HeLa), and hepatocellular carcinoma cells (Hep G2). In this example, HGPRT was stained using a rabbit polyclonal antibody from Abcam. In all cases, the cancer cell lines stained from 7.3% to 83.5% whereas the normal controls showed surface cell staining of 2.4% to 2.9%, a statistically significant elevation (p<0.05). The antibodies only bind when the salvage pathway enzyme is associated with the plasma membrane.
Figure 5:
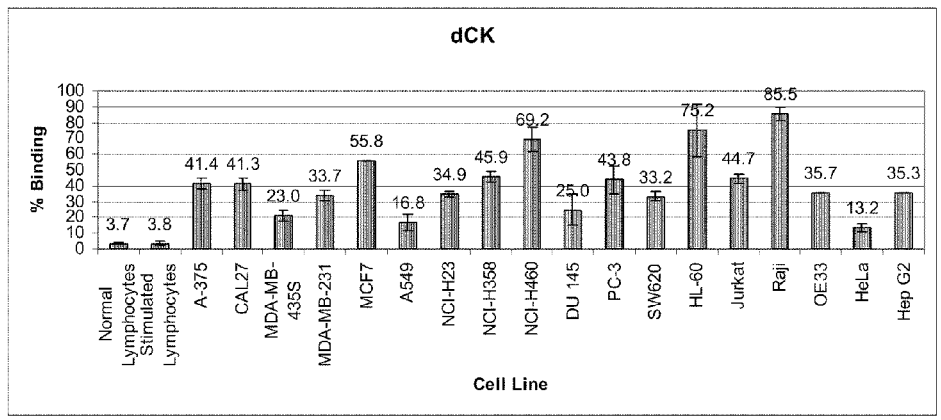
FIG. 5 shows the composite results of repeated flow cytometry experiments to evaluate anti-dCK binding on the surface of normal lymphocytes, lymphocytes stimulated with PHA, malignant melanoma cells (A-375), oral adenosquamous carcinoma cells (CAL27), spindle-shaped cells previously described as derived from ductal carcinoma (MDA-MB-435S), breast adenocarcinoma cells (MDA-MB-231 and MCF7), lung carcinoma cells (A549), lung adenocarcinoma cells (NCI-H23), non-small cell bronchioalveolar carcinoma cells (NCI-H358), large-cell lung carcinoma cells (NCI-H460), prostate carcinoma cells (DU 145), prostate adenocarcinoma cells (PC-3), tumorigenic epithelial cells derived from colorectal adenocarcinoma (SW620), myeloblastic cells derived from promyelocytic leukemia (HL-60), T-cell leukemia cells (Jurkat), lymphoblastoid cells derived from Burkitt's lymphoma (Raji), esophageal adenocarcinoma cells (OE33), cervical adenocarcinoma cells (HeLa), and hepatocellular carcinoma cells (Hep G2). In this example, dCK was stained using a rabbit polyclonal antibody from Abcam. In all cases, the cancer cell lines stained from 13.2% to 85.5% whereas the normal controls showed surface cell staining of 3.7% to 3.8%, a statistically significant elevation (p<0.05). The antibodies only bind when the salvage pathway enzyme is associated with the plasma membrane.
Figure 6:
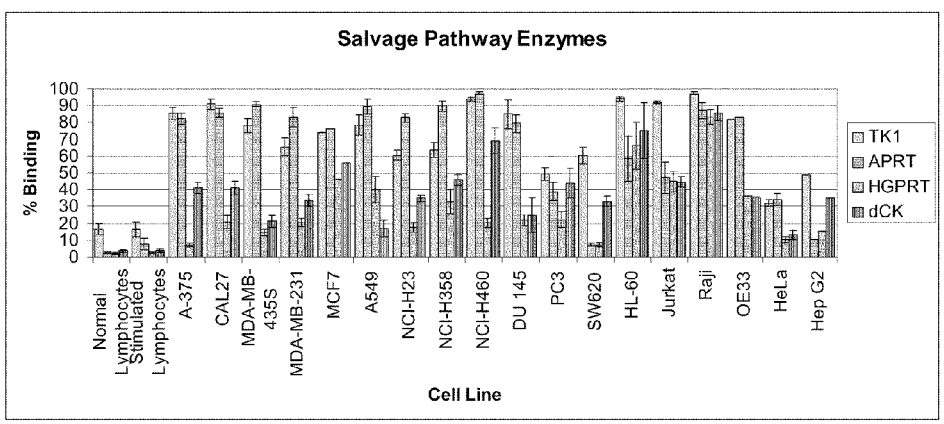
FIG. 6 shows the composite results of repeated flow cytometry experiments to evaluate anti-TK1, anti-APRT, anti-HGPRT, and anti-dCK binding on the surface of normal lymphocytes, lymphocytes stimulated with PHA, malignant melanoma cells (A-375), oral adenosquamous carcinoma cells (CAL27), spindle-shaped cells previously described as derived from ductal carcinoma (MDA-MB-435S), breast adenocarcinoma cells (MDA-MB-231 and MCF7), lung carcinoma cells (A549), lung adenocarcinoma cells (NCI-H23), non-small cell bronchioalveolar carcinoma cells (NCI-H358), large-cell lung carcinoma cells (NCI-H460), prostate carcinoma cells (DU 145), prostate adenocarcinoma cells (PC-3), tumorigenic epithelial cells derived from colorectal adenocarcinoma (SW620), myeloblastic cells derived from promyelocytic leukemia (HL-60), T-cell leukemia cells (Jurkat), lymphoblastoid cells derived from Burkitt's lymphoma (Raji), esophageal adenocarcinoma cells (OE33), cervical adenocarcinoma cells (HeLa), and hepatocellular carcinoma cells (Hep G2). In all cases, the cancer cell lines had statistically significant elevations in SPE binding (p<0.05). The antibodies only bind when the salvage pathway enzymes are associated with the plasma membrane. This figure demonstrates that all four salvage pathway enzymes are on the surface of cancer cells and not on the surface of normal cells. This allows all four salvage pathway enzymes to be used to specifically target cancer cells. Thus, all four salvage pathway enzymes can be used as targets for the therapeutic treatment of cancer or as markers for the identification of cancer cells compared to normal cells, assessing the prognosis of a patient or assessing the progress of a therapy by observing (relative) levels of one or more salvage pathway enzymes relatively to normal cells or in comparison to a previous value.
Figure 7:
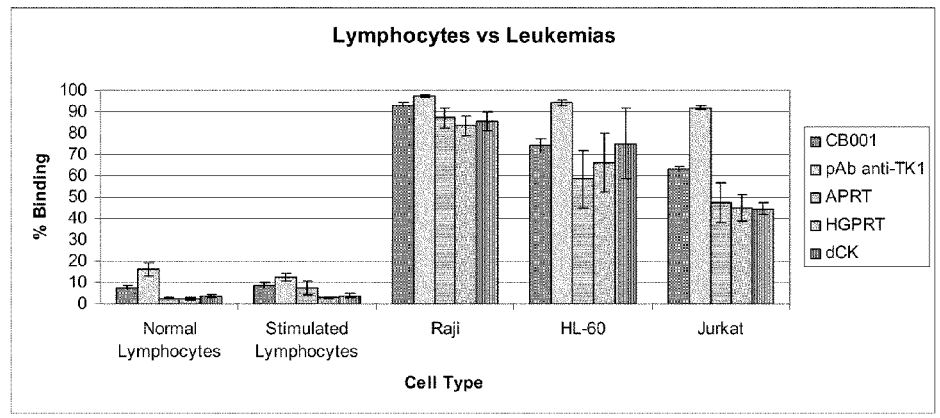
FIG. 7 shows the composite results from repeated flow cytometry experiments using antibodies to the salvage pathway enzymes to evaluate TK1, APRT, HGPRT, and dCK binding on the surface of myeloblastic cells derived from promyelocytic leukemia (HL-60), T-cell leukemia cells (Jurkat), and lymphoblastoid cells derived from Burkitt's lymphoma (Raji), compared with normal lymphocytes and normal lymphocytes stimulated with PHA. The antibodies would only bind if the HGPRT, APRT, TK1 and dCK proteins were present on the plasma membrane. This figure demonstrates that all four salvage pathway enzymes are significantly elevated on the surface of lymphoma and leukemic cells compared to the surface of normal cells (p<0.05). This allows all four salvage pathway enzymes to be used to specifically target cancer cells. Thus, all four salvage pathway enzymes can be used as targets for the therapeutic treatment of lymphoma and leukemia or as markers for the identification of cancer cells compared to normal cells, assessing the prognosis of a patient or assessing the progress of a therapy by observing (relative) levels of one or more salvage pathway enzymes relatively to normal cells or in comparison to a previous value.
Figure 8:
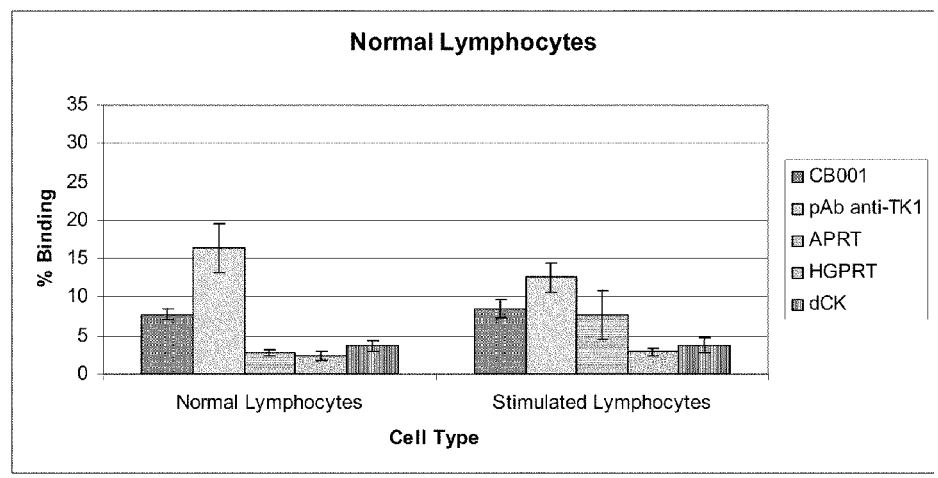
FIG. 8 shows the composite results from repeated flow cytometry experiments using antibodies to the salvage pathway enzymes to evaluate their surface binding on normal lymphocytes and normal lymphocytes stimulated with PHA. The antibodies would only bind if the HGPRT, APRT, TK1 and dCK proteins were present on the plasma membrane. This figure demonstrates that even when normal lymphocytes are stimulated with PHA to rapidly divide like replicating cancer cells, there was no significant elevation of SPE on the plasma membrane surface (p>0.20)
Figure 9:
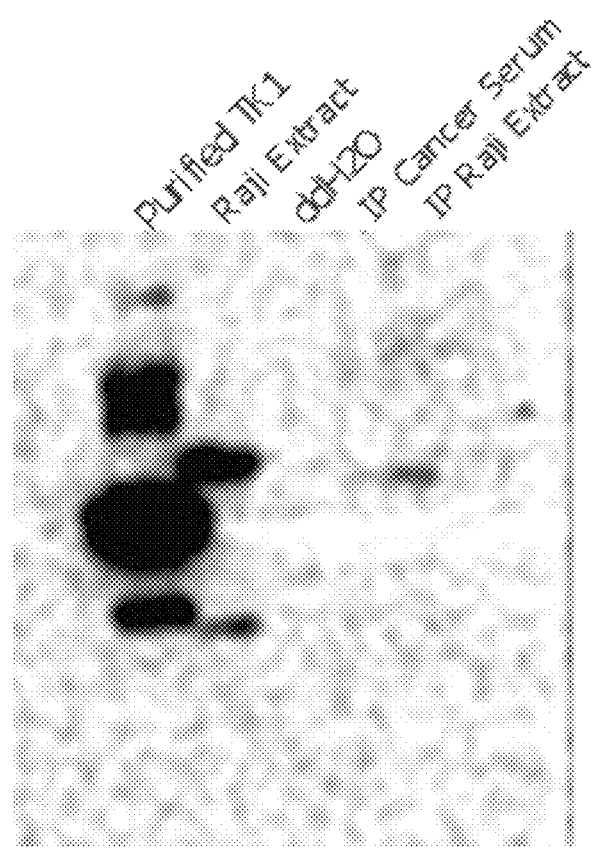
FIG. 9. Western blot of and co-Immunoprecipitation using beads coated with anti-HGPRT antibody, then probed with anti-TK1 antibody. (Ladder not depicted) Lane 1 consists of purified TK1 as a positive control, Lane 2 is unmodified Raji extract, Lane 3 is a negative control of double-distilled water (ddH$_2$O), Lane 4 is Co-IP product from column (anti HGPRT antibody) when cancer serum is passed through it and stained in a Western blot using anti TK1 antibody. Lane 5 is Co-IP product from column when Raji Extract is passed through it. The fact that there was a band seen in cancer serum when staining with antiTK1 antibody indicates that there was a complex in the serum that can be pulled out using an antibody to HGPRT, that stains with an antibody to TK1.
Figure 10A:
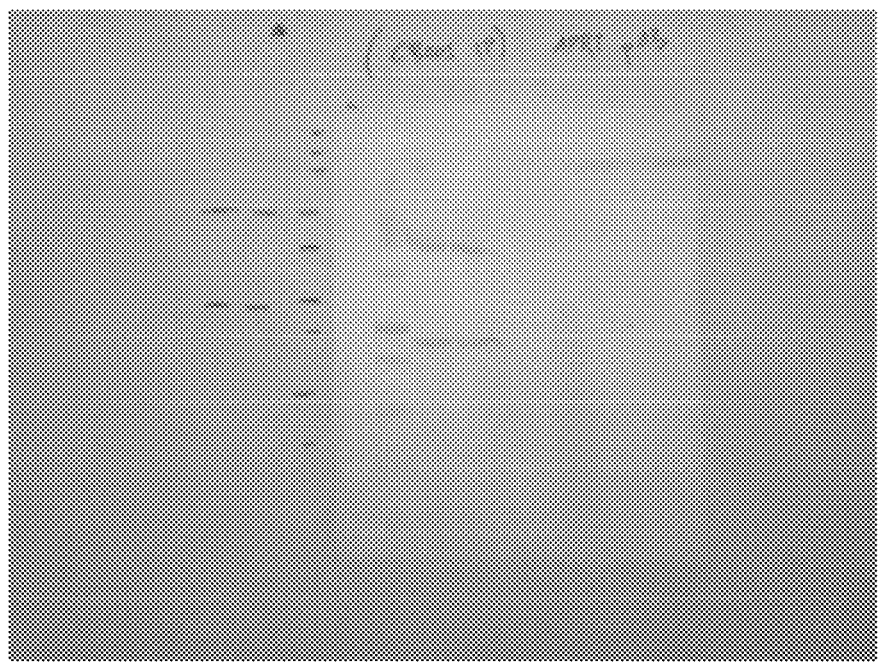
FIGS. 10A-C illustrate the results for Western blots on cancer and normal serum samples. Lane 1: molecular weight markers, Lane 2: Cancer serum (CB001 immunoprecipitation (IP) pull down), Lane 3: Raji extract (CB001 IP pull down), Lane 4: Normal serum 113 A, Lane 5: Cancer serum, Lane 6: Double distilled H$_2$O control. These results confirm that the four salvage pathway enzymes formed a complex in the serum. These blots were performed on serum samples that had been immunoprecipitated using an antibody to TK1 (CB001) and then stained separately with antibodies against APRT, HGPRT, dCK, and TK1. In each case the anti-TK1 antibody precipitated a complex associated with TK1. This complex was stained with each of the antibodies to the other three salvage pathway enzymes (APRT, HGPRT and dCK). This experiment has been repeated using anti-APRT as the immunoprecipitating (pull down) antibody. The same results were obtained for the complex pulled out using anti-APRT and stained with antibodies against HGPRT, dCK, APRT and TK1. This complex is seen diagnostically in the serum of cancer patients.
Figure 10B:
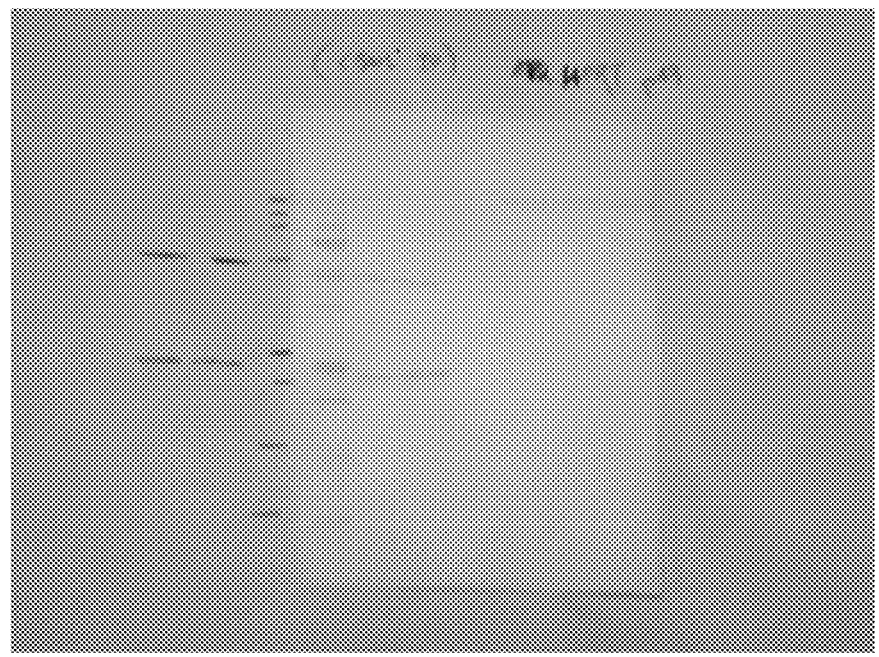
Figure 10C:
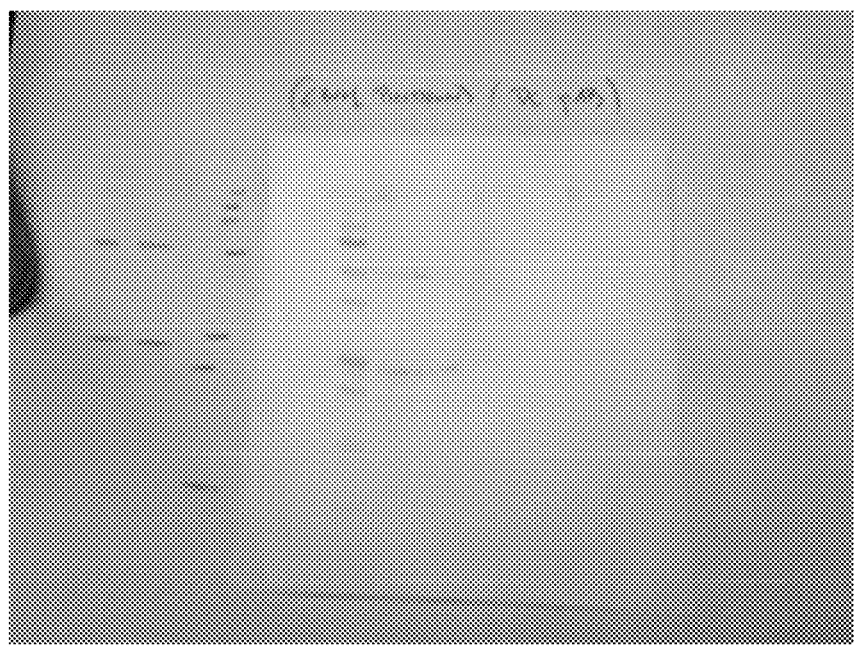
Figure 11:
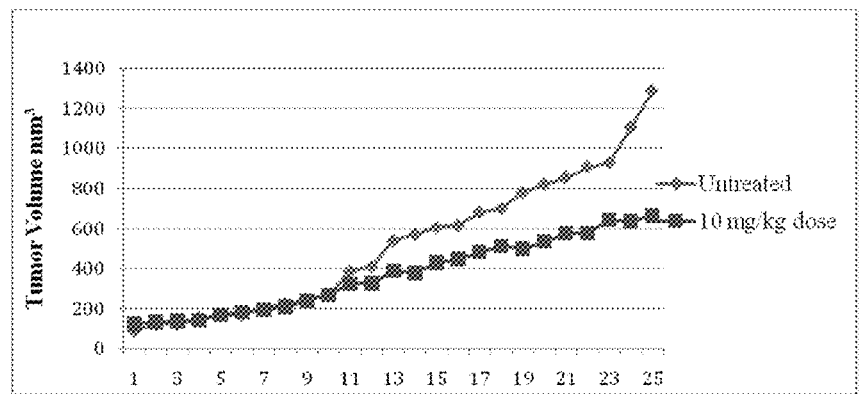
FIG. 11 shows the results of a blind xenograft study, which was performed on nude mice. One million MDA-MB-435 cells (a human melanoma/breast cancer cell line) were injected into the dorsal side of each mouse. Thirty-two mice were used, 16 treated with an anti-salvage pathway enzyme antibody and 16 untreated. CB001, a monoclonal antibody specific for human TK1, was administered intraperitoneally three times over ten days, and the tumor volumes were measured regularly. The results show that there was significant reduction in tumor volume in antibody-treated mice as compared to untreated controls. The mice showed no observable negative side effects from the treatment.
Figure 12:
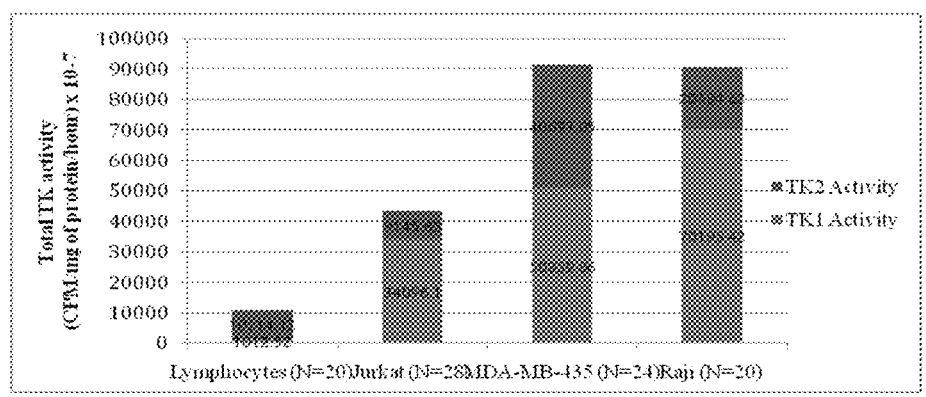
FIG. 12 provides the results of an experiment in which plasma membranes were separated and assayed for TK activity using a radioassay. Both human isozymes of TK (TK1 and TK2) were measured. This indicated the presence of TK1 on the surface of cancer cells (breast cancer, a lymphoblastoid derivative, and lymphoma). Minimal levels of TK1 were found on the surface of normal lymphocytes. TK1 and TK2 values for each cell type were as follows: Lymphocytes, 1012.52 and 10114.12; Jurkat cells, 34096.1 and 9145.63; MDA-MB-435 cells, 50859.86 and 40697.05; and Raji cells, 70195.42 and 20484.62.
Figure 13:
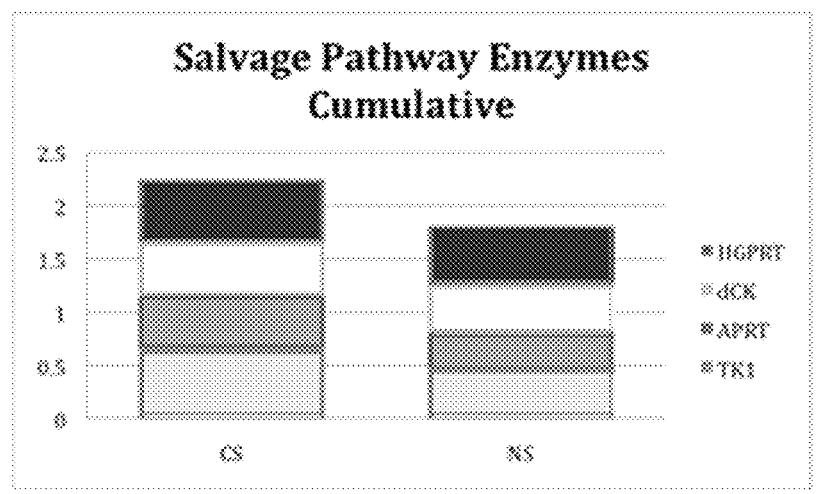
FIG. 13 illustrates the additive results of the four salvage pathway enzymes (TK1, APRT, HGPRT, and dCK) measured by immunoassay in three normal serum samples and three cancer serum samples on the ELISA platform. Each salvage pathway enzyme's contribution to the additive result is shown. The levels of the four salvage pathway enzymes were measured in cancer serum and compared to normal serum using a sandwich ELISA for each of the different SPEs. Cancer serum absorbance was 2.25 while normal serum was 1.81 (difference of 0.44). This indicates that cumulative totals of the salvage pathway enzymes give more accurate information than measuring single salvage pathway enzymes alone.
Figure 14:
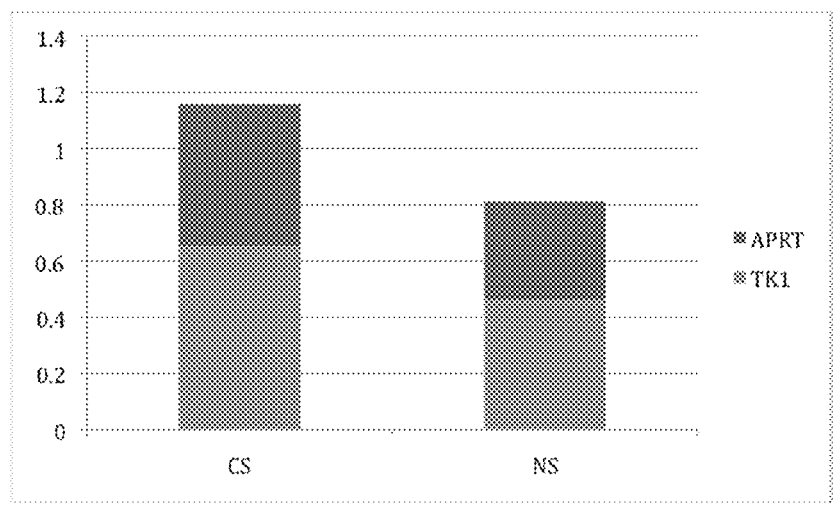
FIG. 14 shows the cumulative value of TK1 and APRT can be used to detect cancer better than either enzyme alone. Cancer serum was compared to normal serum in a sandwich ELISA specific for either TK1 or APRT. The difference between cancer and normal serum was approximately double for the enzymes cumulatively than for either enzyme alone. TK1 distinguished cancer from normal by 0.189 while APRT distinguished cancer from normal by 0.157. However, the cumulative absorbance of TK1 and APRT distinguished cancer from normal by 0.346.
Figure 15:
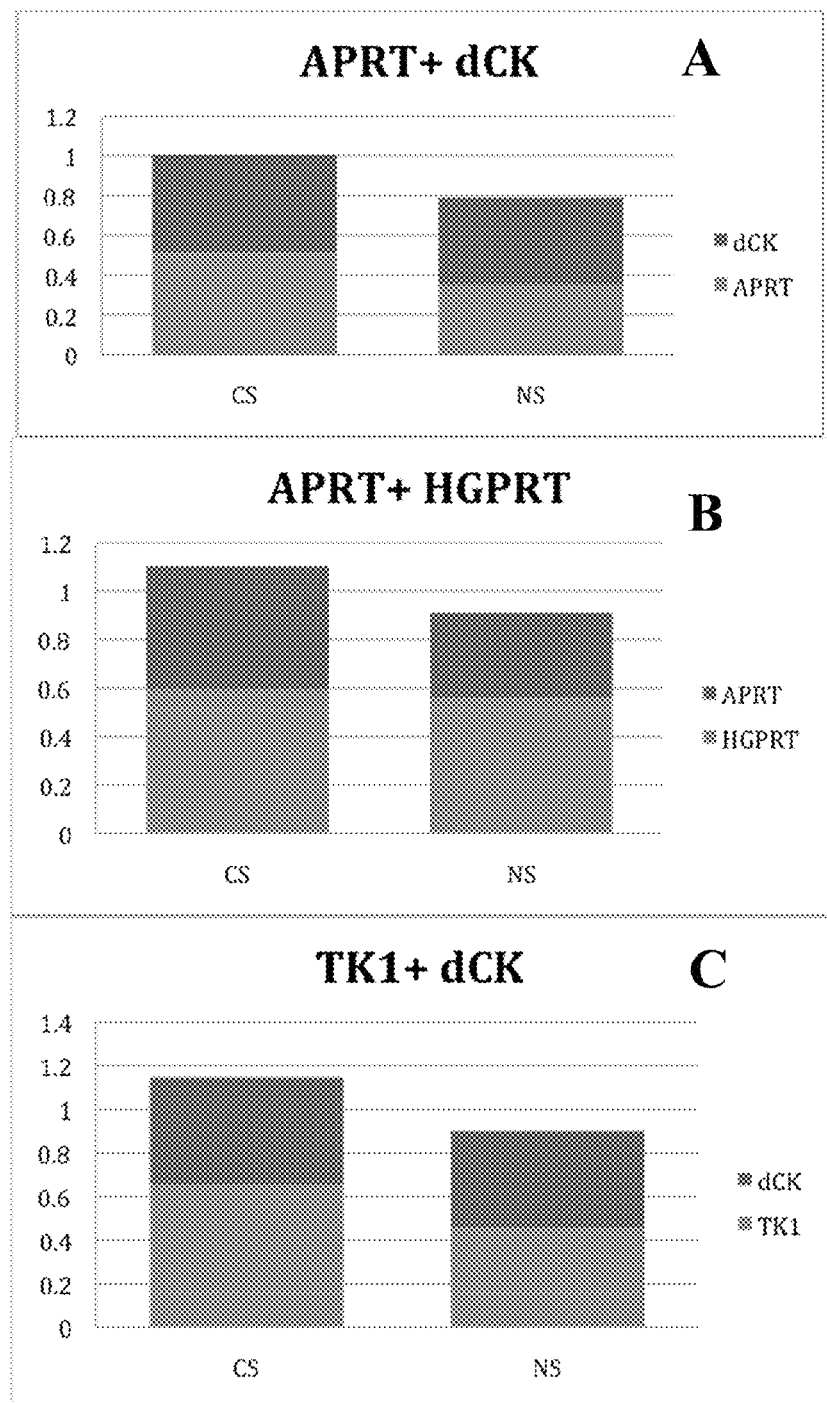
FIG. 15: Similar results to those shown in FIG. 2 were found among all the salvage pathway enzymes. Cancer and normal serums were compared using sandwich ELISAs for the respective enzymes. A) APRT alone distinguished cancer serum from normal serum by an absorbance of 0.157 while dCK distinguished cancer serum from normal serum by 0.055, but when these SPEs were used together the difference increased to 0.212. B) The cumulative score of APRT and HGPRT distinguished cancer from normal by 0.193 (whereas the difference for APRT was 0.157 and HGPRT was 0.036). C) The cumulative score of dCK and TK1 distinguished cancer from normal by 0.244 (whereas the difference for dCK was 0.055 and TK1 was 0.189). Similar results were found among all combinations of salvage pathway enzymes.
Figure 16:
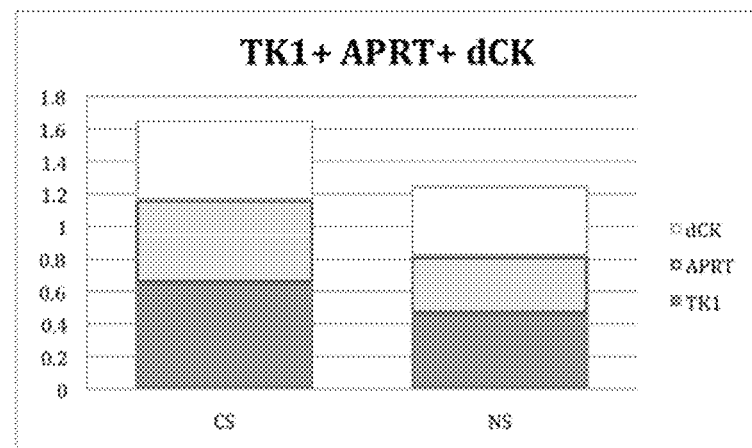
FIG. 16: Three salvage pathway enzymes detected cancer better than any enzyme alone or in combination with one other enzyme. TK1, APRT, and dCK combined were able to distinguish cancer from normal by 0.401. This is almost double the difference of two salvage pathway enzymes.
Figure 17:
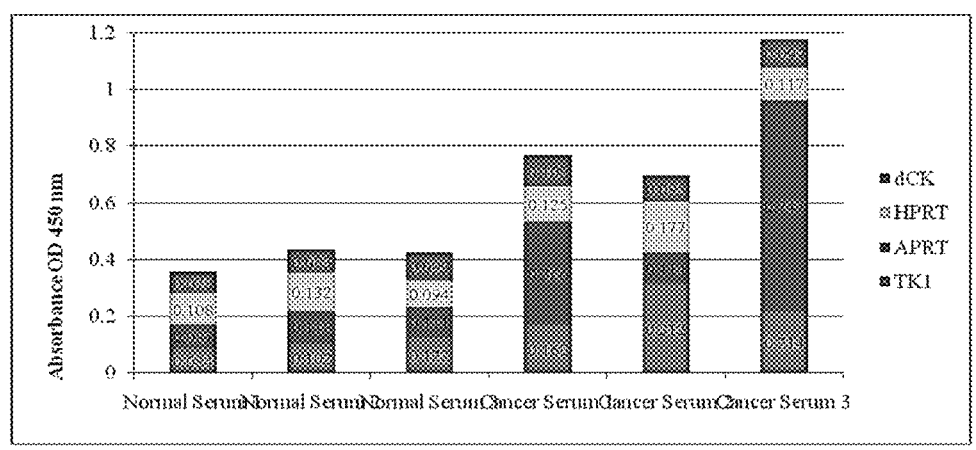
FIG. 17. This illustrates the diagnostic improvement gained by measuring all four SPEs in serum from normal and cancer patients. Individual serum samples from three normal and three cancer patients were measured for all four SPEs using ELISA. In these histograms, the values for TK1, APRT, HGPRT and dCK were as follows: normal serum 1, 0.084, 0.087, 0.108 and 0.078; normal serum 2, 0.102, 0.118, 0.132 and 0.083; normal serum 3, 0.122; 0.111, 0.094 and 0.099; cancer serum 1, 0.168, 0.366, 0.125 and 0.108; cancer serum 2, 0.312, 0.114, 0.177 and 0.095; and cancer serum 3, 0.214, 0.747, 0.117 and 0.099. The first three bars to the left are data from three normal serum samples, while the three bars to the right represent data from three cancer serum samples.
Figure 18:
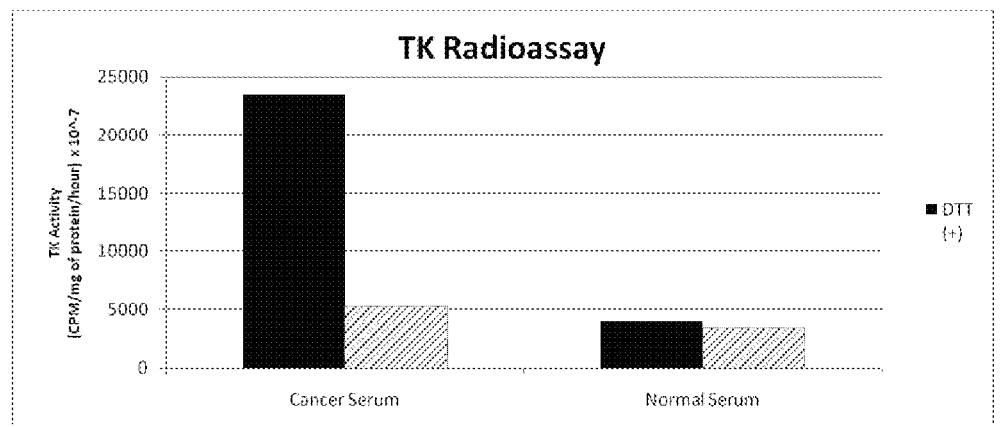
FIG. 18 shows the results of the TK1 radioassay on serum from cancer and control patients before and after treating the serum with 1,4-dithiothreitol (DTT) to break down the salvage pathway complex. The radioassay utilizes the natural biochemical pathway in which thymidine kinase is involved in the cell. It measures the conversion of radioactive deoxythymidine to deoxythymidine monophosphate (dTMP) by thymidine kinase. This information was used to deduce the levels of the salvage pathway enzyme's activity.
Figure 19:
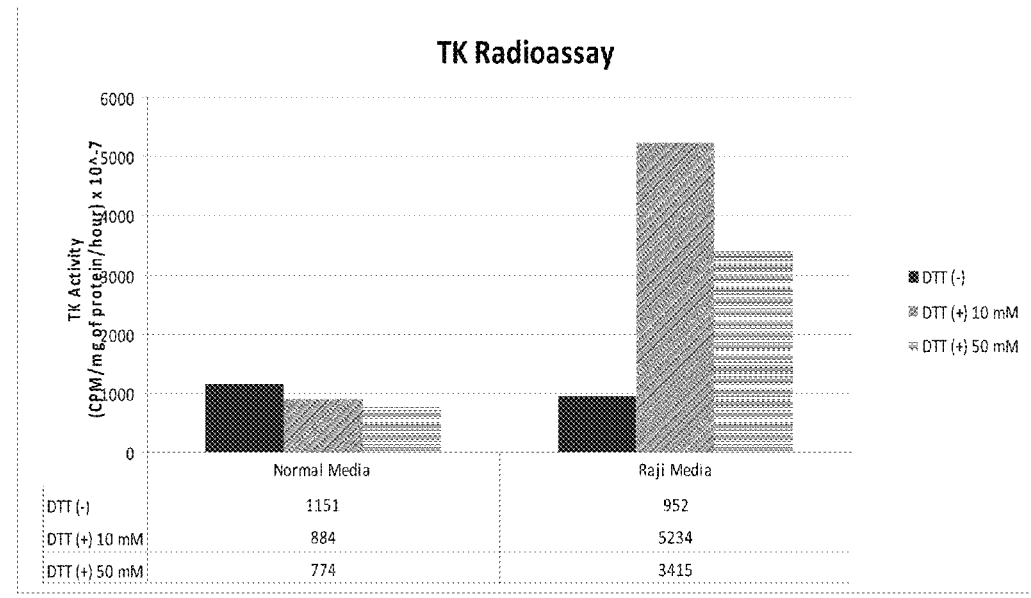
FIG. 19 provides the results of TK1 analysis via TK radioassay of media from Raji cells and normal media before and after treatment with DTT to break down the salvage pathway complex. Note that excess of DTT reduced the activity of TK1
Figure 20:
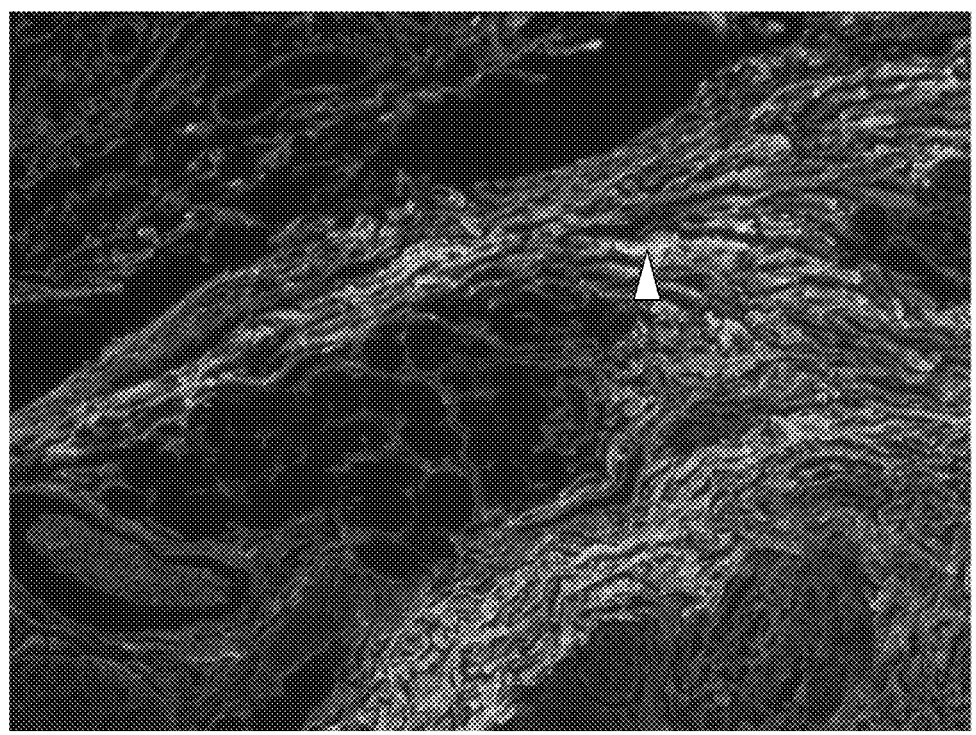
FIG. 20: TK1 and APRT localized together in lung cancer tissue. Lung cancer tissue was sectioned and stained with both a mouse monoclonal TK1 antibody and rabbit polyclonal APRT antibody. TK1 was subsequently labeled with a rhodamine antibody while APRT was labeled with a FITC antibody. It was clear that TK1, which stained red, and APRT, which stained green, were co-localized in some locations, which appeared as yellow, but were also found separately in areas of red or green only. Controls were run in which the anti-mouse rhodamin was paired with the rabbit polyclonal and the anti-rabbit FITC was paired with the mouse monoclonal. In both cases there was minimal staining which appeared significantly different from the experimental sample.
Figure 21:
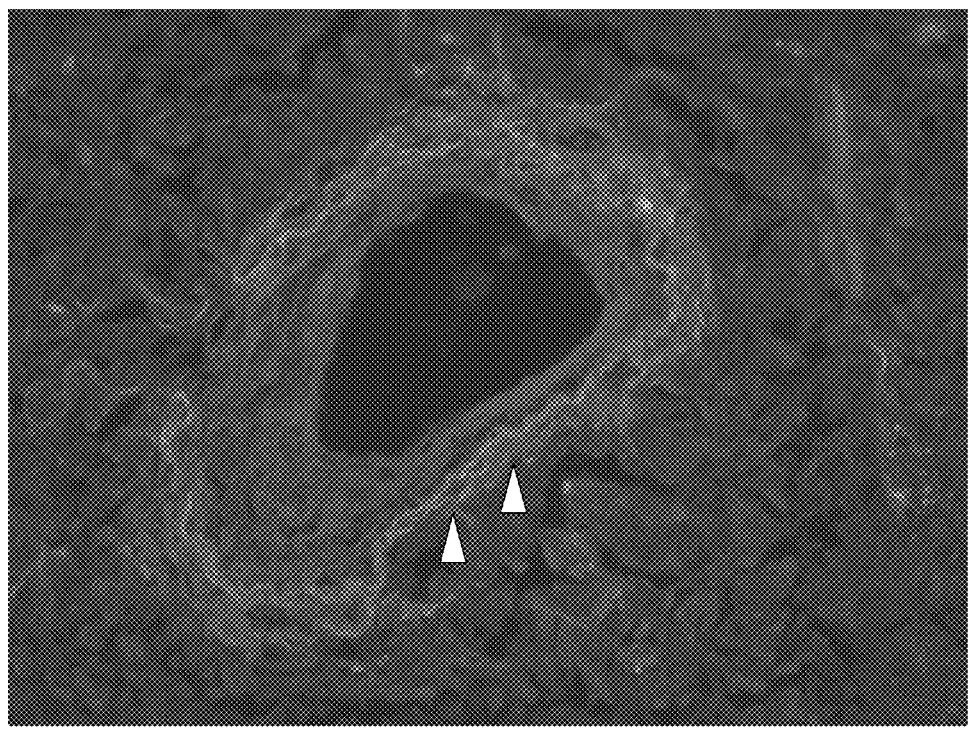
FIG. 21: TK1 and dCK localization. Lung cancer tissue was stained with TK1 mouse monoclonal rhodamin antibody and a dCK rabbit polyclonal fluorescein isothiocyanate (FITC) antibody similar to the process of FIG. 5. dCK showed markedly lower staining levels when compared to APRT, and did not appear to localize together with TK1 in this tissue. Interestingly TK1 and dCK were frequently seen in the same areas of the tissue, but did not co-localize.
Figure 22A:
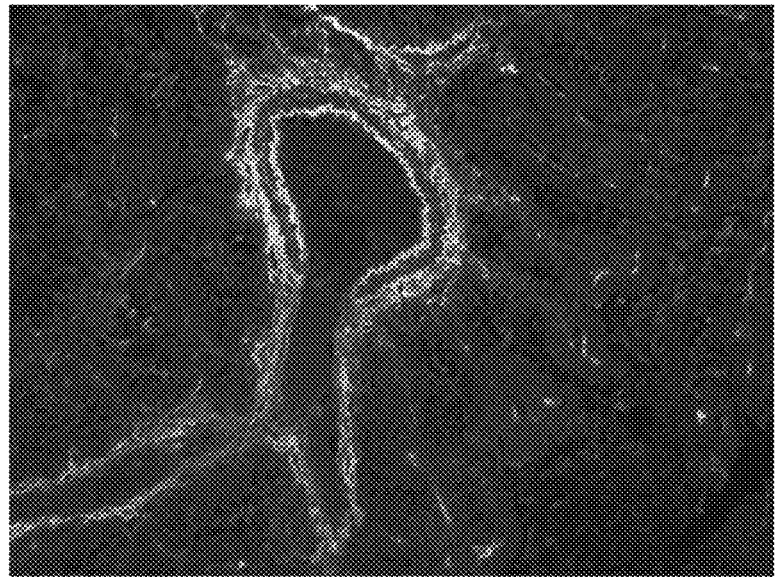
FIG. 22: TK1 and HGPRT co-localization in lung cancer tissue. Lung cancer tissue was stained similar to the process of FIGS. 5 and 6 with a TK1 mouse monoclonal rhodamine antibody and HGPRT rabbit polyclonal FITC antibody. TK1, which stained red, and HGPRT, which stained green, did appear to localize in some areas, but they were also found separately. A and B represent two different areas of the same tissue.
Figure 22B:
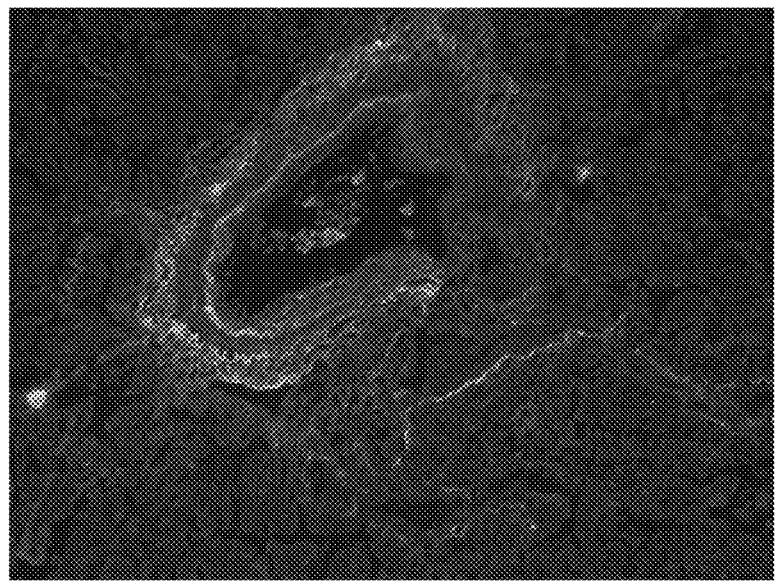
Figure 23A:
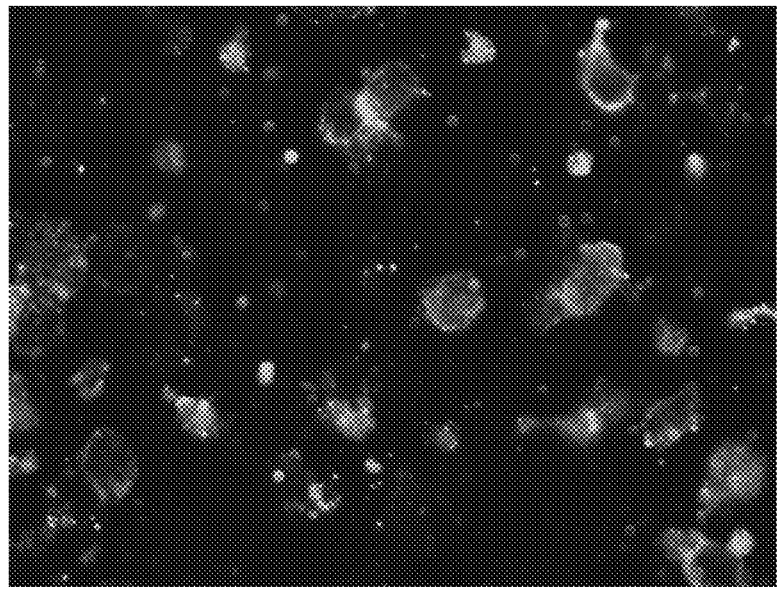
FIGS. 23A-L demonstrate binding on the plasma membrane by antibodies against the four SPEs. The cells were various types of live cancer cells, stained on their surface using a primary antibody against the different SPEs, and stained using a secondary antibody conjugated with FITC. This demonstrates binding on the plasma membrane, illustrating the presence of each of the four salvage pathway enzymes on the plasma membrane of different cancer cells and not on the surface of normal cells.
Figure 23B:
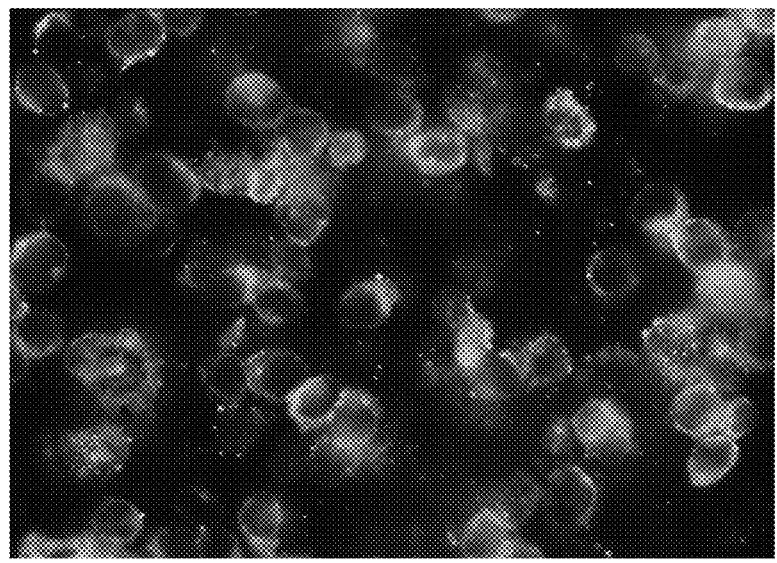
Figure 23C:
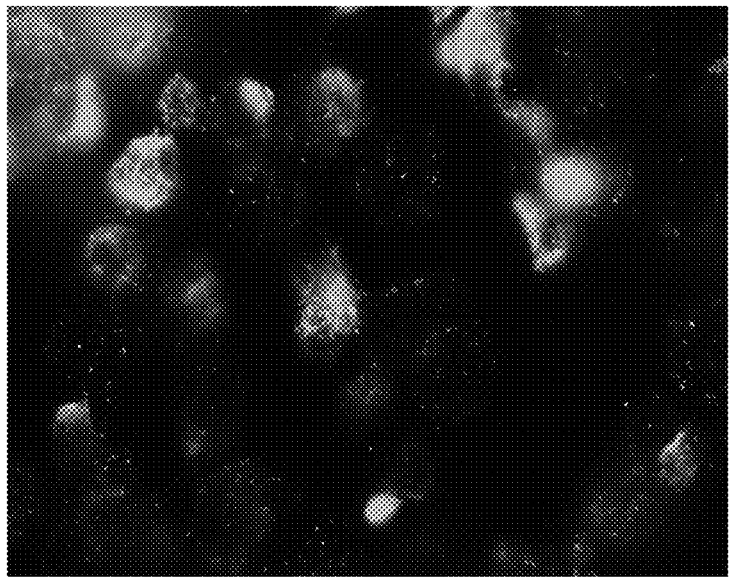
Figure 23D:
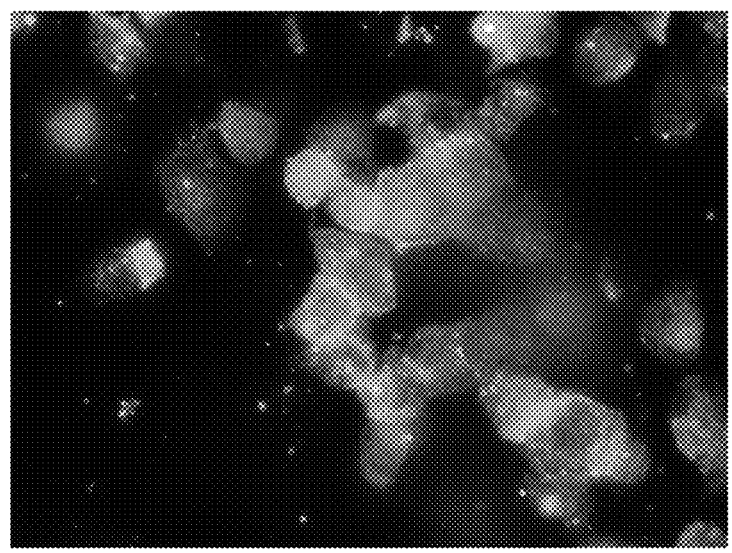
Figure 23E:
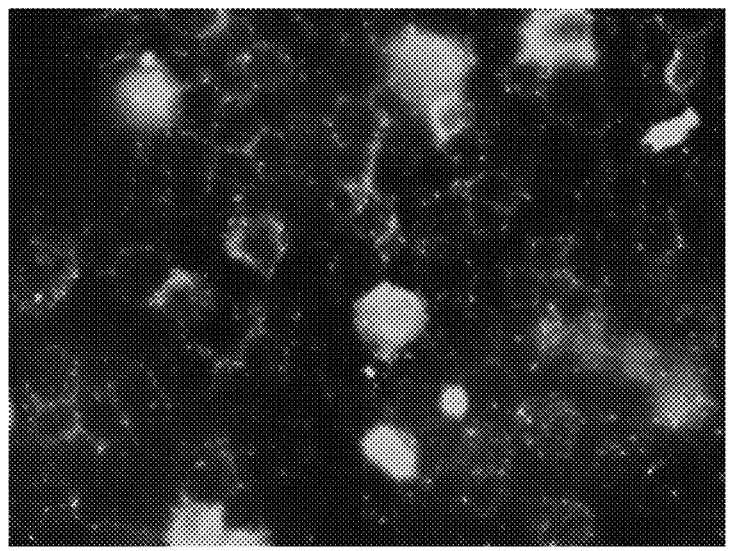
Figure 23F:
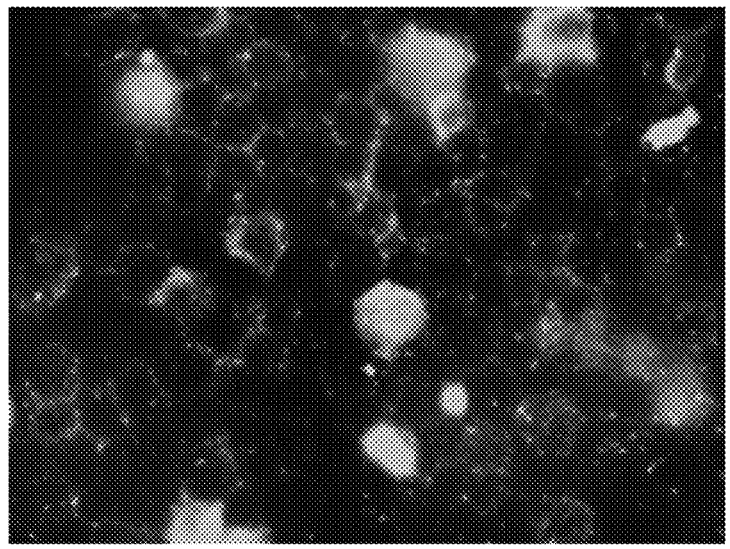
Figure 23G:
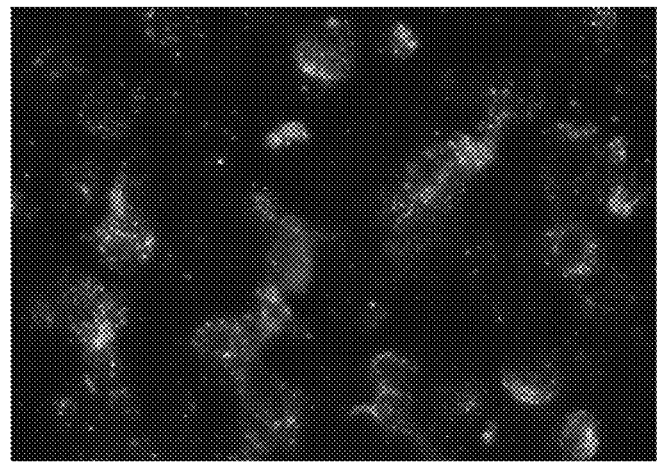
Figure 23H:
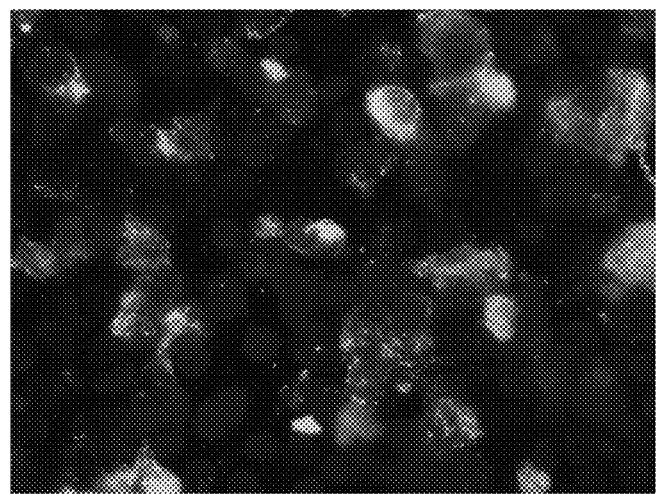
Figure 23I:
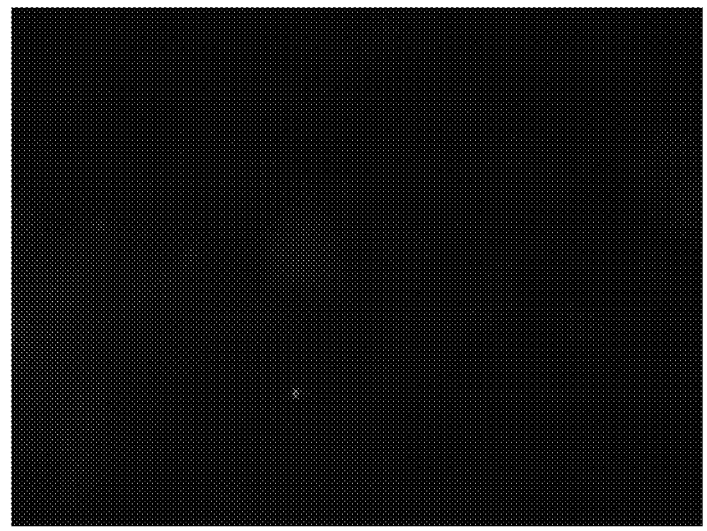
Figure 23J:
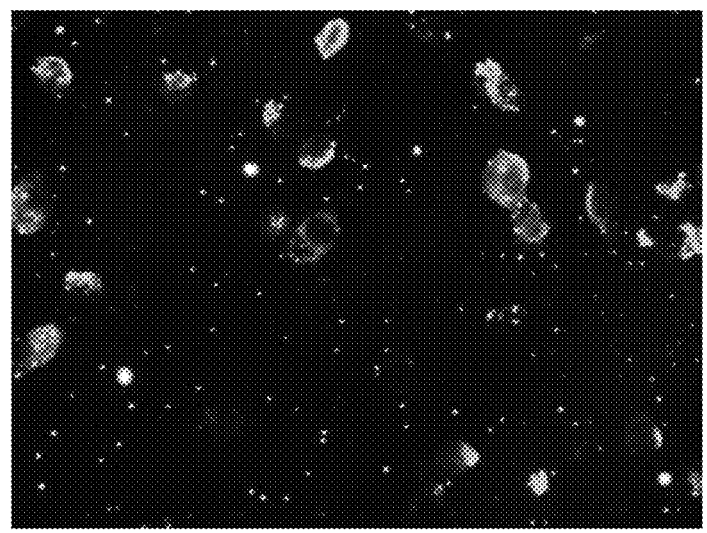
Figure 23K:
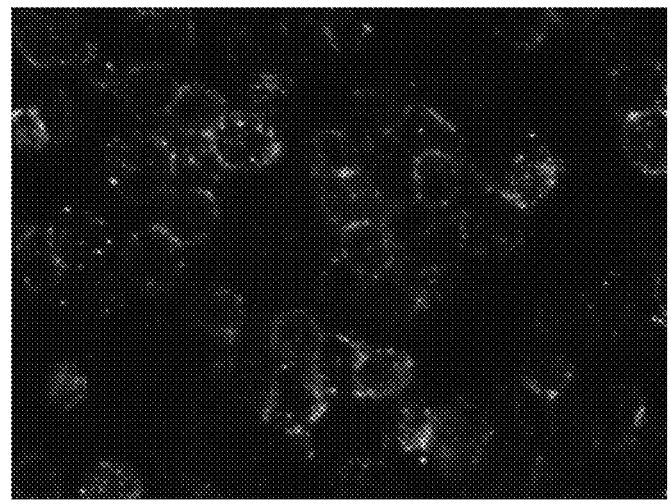
Figure 23L:
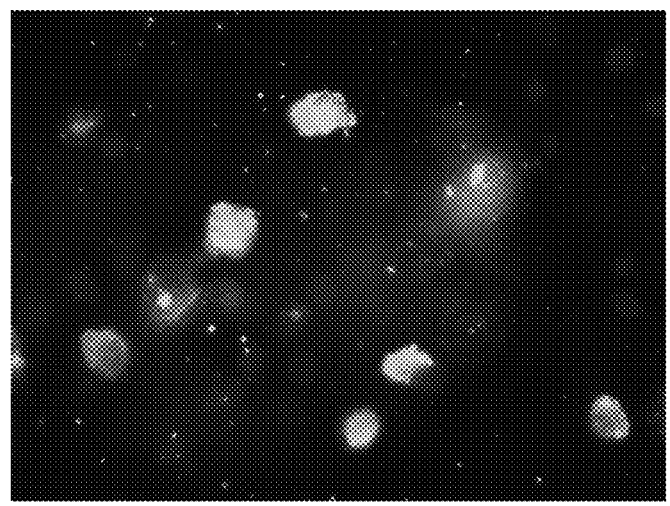

FIG. 2 shows the results obtained using flow cytometry analysis of different cancer cell types. These are repeats of at The complex can be, for example, immunoprecipitated using a first antibody to a salvage pathway enzyme, e.g., TK1 or HGPRT, and detected via directly or indirectly detectable antibody to one or more other salvage pathway enzymes, or via directly or indirectly detectable antibody specific to the first antibody. It was also demonstrated that the nucleotide salvage pathway enzymes are present in the plasma membrane of cancer cells, but not in the plasma membrane of normal cells. This was initially suggested from the flow cytometry data and confirmed by isolating the plasma membranes and analyzing for salvage pathway enzyme activity via flow cytometry for all four enzymes in many different cancer cell types. Transmission electron microscopy provided further evidence of the presence of salvage pathway enzymes on the plasma membrane (data not shown).

The fluorescence microscopy overlay pictures of stained cells show that the proteins appear to be forming a complex or forming clumps very close to each other on the surface of cancer cells The flow cytometry results indicate that all four salvage pathway enzymes are present on the surface of cancer cells and are not found in similar quantities on normal cells. Without wishing to be bound by any particular theory, it is also believed that the salvage pathways enzymes form a complex on the cancer cell surface, and that the same or a similar complex occurs in the serum of cancer patients.

Extractions of plasma membranes from different cancer cells have been carried out, and the resulting material has been assayed for TK1 activity using an activity assay (TK1 radioactive assay), the results of which indicate that these enzymes are present and active in the plasma membranes of cancer cells and not present or at significantly lower levels in the membranes of normal cells.

The cancer sera were also tested using the ELISA, which confirmed that these proteins are highly expressed by cancer cells. Sera from many types of cancer patients were tested to determine whether ELISA of the salvage pathway enzymes could be used as an effective prognostic test. The results indicate that all these proteins are highly expressed in cancer sera. The levels vary but TK1 and APRT have been more highly expressed than HGPRT and dCK although this is not always the case. These results again confirm the presence of all four salvage pathway enzymes in a complex in the sera of cancer patients and indicate that measurements of all four enzymes or combinations of any of the four give a better indication of cancer, and cancer progression than measurements of a single salvage pathway enzyme. Our results indicate a more definitive result is obtained by measuring all four salvage pathway enzymes or combinations of different ones than by measuring only one salvage pathway enzyme.

Targeting this multienzyme complex and the individual SPEs allows for improved methods and compositions for diagnosing, assessing prognosis, monitoring the success of treatment, and targeting cancer cells for visualization or cancer treatment, e.g., with cytotoxic agents.

All references throughout this application, for example patent documents including issued or granted patents or equivalents; patent application publications; and non-patent literature documents or other source material; are incorporated by reference herein in their entireties for purposes of written description and enablement, as though individually incorporated by reference, to the extent each reference is not inconsistent with the disclosure in this application (i.e., a reference that is inconsistent herewith is incorporated by reference except for the inconsistent portions of the reference).

Patents and publications mentioned in the specification reflect the level of skill of those skilled in the art to which the methods, kits and compositions pertains. References cited herein are incorporated by reference herein in their entireties to indicate the state of the art, in some cases as of their filing date, and it is intended that this information can be employed herein, if needed, to exclude (e.g. to disclaim) specific embodiments that are in the prior art. For example, when a composition is claimed, it should be understood that compositions known in the prior art, including compositions disclosed in the references are not intended to be claimed.

When a Markush group or other grouping is used herein, all individual members of the group and all combinations and subcombinations possible of the group are intended to be individually included in the disclosure.

When an "antibody" or "binding molecule" or other molecule is referred to herein in the singular, the plural is included when these terms are used in connection with the description of the methods described herein to refer to molecules that bind SPEs. The singular form of these terms can include molecules that bind multiple different SPEs, unless the context indicates that a binding molecule to only a single SPE is being referred to.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individually or in any combination.

One of ordinary skill in the art will appreciate that assay formats, detection and assessment methods, and/or samples other than those specifically exemplified can be employed in the practice of the invention without resort to undue experimentation. All art-known functional equivalents, of any such methods, input materials, and salvage pathway enzyme-specific binding molecules, are intended to be included in the scope of the appended claims.

Whenever a range is given in the specification, for example, a temperature range, a time range, concentration range, or a composition range, all intermediate ranges and subranges, as well as all individual values included in the ranges given are intended to be included in the disclosure, and the end point values of the ranges are also intended to be included.

As used herein, "comprising" is synonymous with "including," "containing," or "characterized by," and is inclusive and open-ended and does not exclude additional, unrecited elements or method steps. As used herein, "consisting of" excludes any element, step, or ingredient not specified in the claimed element. As used herein, "consisting essentially of" does not exclude materials or steps that do not materially affect the basic and novel characteristics of the claim. Any recitation herein of the term "comprising," particularly in a description of components of a composition or in a description of elements of a device, is understood to encompass those compositions and methods consisting essentially of and consisting of the recited components or elements. The methods, kits and compositions illustratively described herein can be practiced in the absence of any element or elements, limitation or limitations which is not specifically disclosed herein.

In general the terms and phrases used herein have their art-recognized meaning, which can be found by reference to standard texts, journal references and contexts known to those skilled in the art. Although the present specification contains certain specific examples and descriptions, these should not be construed as limiting in scope but as merely providing illustrations of some of the embodiments of the present methods, kits and compositions. For example, the scope should be determined by the appended claims and their equivalents, rather than by the examples given herein. It will be understood by those of skill in the art that numerous and various modifications can be made without departing from the spirit of what is claimed. Therefore, it should be clearly understood that the forms of the methods and compositions disclosed herein are illustrative only and are not intended to limit the scope hereof.

REFERENCES

Abram, W. P. et al. (1985), "Leukocyte thymidine kinase activities in cancer patients," Cancer Prevention and Detection 8, (5/6), 589.

Armstrong, B. et al. (1990), "Selective inhibition of thymidine kinase isozymes by (E)-5-(2-Bromovinyl)-2-deoxyuridine," Biochemical Society Transactions 18:270.

Balzarini et al. (1982), "Role of Thymidine Kinase in the Inhibitory Activity of 5-Substituted-2'-Deoxyuridines on the Growth of Human and Murine Tumor Cell Lines: Biochem. Pharmacal. 31(6):1089-1095.

Baron et al. (1990), "A Rapid Two-Step Purification of Rat Liver Fetal Thymidine Kinase: Preparative Biochem. 20 (3-4):241-256.

Barrett, I. T. (1983), "Textbook of Immunology," p. 249.

Beckman et al. (2007), Cancer, 109:170-179.

Boivin et al. (2002), "Intranasal Herpes Simplex Virus Type 2 Inoculation Causes a Profound Thymidine Kinase Dependent Cerebral Inflammatory Response in the Mouse Hindbrain," Eur. J. Neurosci. 16(1):29-43.

Bradshaw. H. D. Jr. (1983), "Molecular Cloning and Cell-Specific Regulation of a Functional Human Thymidine Kinase Gene: Proc. Natl. Acad. Sci. USA 80:5588-5591.

Bristow, H. et al. (1988), "Leakage of thymidine kinase from proliferating cells," Biochemical Society Transactions, 16:55-56.

Bronzert et al. (1981), "Purification and Properties of the Estrogen-Responsive Cytoplasmic Thymidine Kinase from Human Breast Cancer," Cancer Res. 41:604-610.

Carter et al. (1992), "Humanization of an anti-p185$^{Her2}$ antibody for human cancer therapy," Proc. Natl. Acad. Sci. USA, 89:4285-4289.

Cespdes et al. (2006), Clin. Transl. Oncol. 8(5):318-329.

Chatterjee et al. (1994), Cancer Immunol. Immunother., 38:75-82.

Co et al. (1994), "A Humanized Antibody Specific for the Platelet Integrin gpllb/llla," Journal of Immunology, 152: 2968-2976.

Cruse et al. (2004), "Atlas of Immunology," Second Edition, CRC Press, pp 282 and 640.

Daugherty et al. (1991), "Polymerase Chain Reaction Facilitates the Cloning, CDR-Grafting, and Rapid Expression of a Murine Monoclonal Antibody Directed Against the CD18 Component of Leukocyte Integrins," Nuc. Acids Res. 19(9):2471-2476.

Dennis, (2006), Nature 442:739-741

Ellims et al. (1982), "Human Thymidine Kinase: Purification and Some Properties of the TK1 Isoenzyme from Placenta: Mol. Cell. Biochem. 45:113-116.

Flemington (1987), "Sequence, Structure and Promoter Characterization of the Human Thymidine Gene," Gene 52:267-277.

Fujimori et al. (1990), J. Nuc. Med. 31:1191-1198.

FUNDAMENTAL IMMUNOLOGY (1996), 242 (William E. Paul, M. D. ed.), 3d ed.

Gan et at. (1983), "Human Thymidine Kinase," J. Biol. Chem. 258:7000-7004.

Ghaleb, A. H. et al. (2005), "The Comet Assay to Determine the Mode of Cell Death for the Ultrasonic Delivery of Doxorubicin to Human Leukemia (HL-60 Cells) from Pluronic P105 Micelles," Technology in Cancer Research & Treatment 4(6):1-15.

Goding et al. (1980), "Antibody Production by Hybridomas," J. Immunol. Methods 39:285-308.

Gronowitz et al. (1984), "Application of an In Vitro Assay for Serum Thymidine Kinase: Results on Viral Disease and Malignancies in Humans," Int. J. Cancer 33:5-12.

Habteyesus et al. (1991), "Deoxynucleoside Phosphorylating Enzymes in Monkey and Hannigan et al. (1993) "Thymidine Kinase: The Enzymes and Their Clinical Usefulness: Cancer Biother. 8 (3):187-197.

Hannigan, B. M. et al. (1985), Lymphocyte DNA synthesis in malignancy. Biochemical Society Transactions 14:81-82.

He et al. (2002), Cell Prolif. 35(2):69-81.

He, Q. et al. (2000), "The clinical significance of thymidine kinase 1 measurement in serum of breast cancer patients using anti-TK1 antibody," The International Journal of Biological Markers, 15(2):139-146.

Hengstschlager et al. (1993), "Cytofluorometric Assay for the Determination of Thymidine Uptake and Phosphorylation in Living Cells," Cytometry 14: 39-445.

Hengstschlager et al. (1994,) "A Common Regulation of Genes Encoding Enzymes of the Deoxynucleotide Metabolism is Lost After Neoplastic Transformation," Cell Growth Differ. 5(12):1389-1394.

Hengstschlager et al. (1994), "Different Regulation of Thymidine Kinase During the Cell Cycle of Normal Versus DNA Tumor Virus-Transformed Cells: J. Biol. Chem. 269: 13836-13842.

Hickey, I. et al. (1986), "Azacytidine induces reversion of thymidine kinase deficiency in friend erythroleukemia cells," Exp. Cell Res. 164:251-255.

Hoper, M. et al. (1991), "The value of prognostic indicators in predicting metastatic spread of breast cancer," Journal of Pathology 163(2):180.

Habteyesus A, et al. (1991), "Deoxynucleoside phosphorylating enzymes in monkey and Human Tissues Show Great Similarities, While Mouse Deoxycytidine Kinase has a Different Substrate Specificity," Biochem. Pharmacol. 42(9): 1829-36.

Jain (July 1994), Scientific American pp. 58-65.

Jansson et al. (1992), "Mammalian Thymidine Kinase 2, Direct Photoaffinity Labeling with [32P]dCTP of the Enzyme from Spleen, Liver, Heart and Brain," Eur. J. Biochem. 206(2):485-490.

Kauffman et al. (1991), "Cell cycle regulation of thymidine kinase: Residues near the carboxyl terminus are essential for the specific degradation of the enzyme at mitosis," Mol. Cell Biol. 11:2538-2446.

Kohler et al. (1976), "Derivation of Specific Antibody-Producing Tissue Culture and Tumor lines by Cell Fusion," Eur. J. Immuno!. 6:511-519.

Lau et al. (1984), "Direct Isolation of the Functional Human Thymidine Kinase Gene with a Cosmid Shuttle Vector," Proc. Natl. Acad. Sci. USA 81:414-418.

May et al. (1991), "Intracellular Routing Rather than Cross-Linking or Rate of Internalization Determines the Potency of Immunotoxins Directed Against Different Epitopes of slgD on Murine B Cells: Cell Immunol. 135:490-500.

McKenna et al. (1988), "Thymidine Kinase Activities in Mononuclear Leucocytes and Serum from Breast Cancer Patients," Br. J. Cancer 57:619-622.

McKenna, P. G. et al. (1988), "Serum total thymidine kinase levels in the management of breast cancer," Thymidine Kinase, a Marker for Neoplastic and Viral Diseases, Book chapter.

McKenna, P. G. et al. (1988), "Thymidine kinase activities in mononuclear leukocytes and serum from breast cancer patients," British Journal of Cancer 57:619-622.

McKenna, P. G., et al. (1985)," Elevated thymidine kinase levels in mononuclear leukocytes of cancer patients. Journal of Clinical Hematology and Oncology 15:71-76.

Munch-Peterson et al. (1990), "Thymidine Kinase in Human Leukemia—Expression of Three Isoenzyme Variants in Six Patients with Chronic Myelocytic Leukemia," Leuk. Res. 14:39-45.

Munch-Peterson et al. (1991), "Diverging Substrate Specificity of Pure Human Thymidine Kinases 1 and 2 Against antiviral Dideoxynucleosides," J. Bioi. Chem. 266:9032-9038.

Munch-Peterson et al. (1993), "Reversible ATP-Dependent Transition Between Two Forms of Human Cytosolic Thymidine Kinase With Different Enzymatic Properties: J. Biol. Chem. 268(21):15621-15625.

Nesterova, M. et al. (2006), "Autoantibody biomarker opens a new gateway for cancer diagnosis," Biochimica et Biophysica Acta 1762:398-403.

Nevin, G. et al. (1992), "Thymidine kinase activities in effusions from patients with lung cancer," Journal of Tumor Marker Oncology, 7(4):35-39.

Nevin, G. B. et al., (1988), "Thymidine kinase activities in pleural effusions," British Journal of Cancer 58:252-255.

O'Neill K. L. (2001), "Thymidine Kinase: diagnostic and prognostic potential (review) Expert Rev. Mol Diagn. 1(4): 428-433.

O'Neill, K. L et al. (2007), "Thymidine Kinase 1-A prognostic and diagnostic indicator in ALL and AML patients," Leukemia 21, 560-563.

O'Neill, K. L. et al. (1987), "Elevated serum and mononuclear leukocyte thymidine kinase activities in patients with cancer," Irish Medical Journal 80:264-265.

O'Neill, K. L. et al. (1989), "Thymidine kinase (Tk) isozyme levels in tumors and serum samples from breast cancer patients," Proc Int. Soc. Onco. Dev. Bio. and Med. 17:89.

O'Neill, K. L. et al. (1995), "A review of thymidine kinase: the future of breast cancer prognosis," The Breast, 4:79-83.

O'Neill, K. L. (1992), "Breast tumor thymidine kinase levels and disease recurrence," The Journal of Medical Laboratory Sciences 49:244-247.

O'Neill, K. L. et al. (1985), "Lymphocyte thymidine kinase levels in cancer patients and control patients," Heredity 54:424-425.

O'Neill, K. L. et al. (1986), "Deoxythymidine kinase activities in sera from cancer and non-cancer patients," Tumour Biology, 7:236.

O'Neill, K. L. et al. (1986), "Isozymes of leukocyte thymidine kinase in malignancy," Biological Chemistry 367: 238.

O'Neill, K. L. et al. (1986), "Serum thymidine kinase levels in cancer patients," Irish Journal of Medical Science 155:272-274.

O'Neill, K. L. et al. (1987), "Serum thymidine kinase levels in cancer patients," Internal Medicine Digest 3:13-14.

O'Neill, K. L. et al. (1990), "Tumour thymidine kinase levels, estrogen receptor status and recurrence, in breast cancer patients," British Journal of Cancer 62(12):28.

O'Neill, K. L. et al. (1992), "Can thymidine kinase levels in breast tumors predict disease recurrence?," Journal of The National Cancer Institute 84(23):1825-1828.

O'Neill, K. L. et al. (1988), Elevated levels of thymidine kinase in serum and mononuclear leukocytes from patients," Tumour Biology 8:303-304.

Oldham et al. (1993), "Whats the Score," Cancer Biother. 8(3):187-188.

O'Neill et at (1987), "Elevated Serum and Mononuclear Leukocyte Thymidine Kinase Activities in Patients with Cancer," Irish Med. J. 80(9):264-265.

O'Neill et at (1992), "Can Thymidine Kinase Levels in Breast Tumors Predict Disease Recurrence: J. Nat. Cancer Inst. 84(23):1825-1828, 1829-1836.

Pearce, R. H. et al. (1985), "The influence of thymidine kinase on lymphocyte proliferation," British Society for Immunology, (Summer conference, book of abstracts), p 36, London.

Robertson, J. F. R. et al. (1990), "Thymidine kinase in breast cancer," British Journal of Cancer 62:663-667.

Robertson, J. F. R. et al. (1988), "Serum thymidine kinase—a marker for breast cancer," Breast Cancer Research and Treatment 12:134.

Robertson, J. F. R. et al. (1988), "Serum thymidine kinase in advanced breast cancer, British Journal of Surgery 75:1271.

Robertson, J. F. R. et al. (1989), "Serum thymidine kinase—a tumour marker in advanced breast cancer," British Journal of Cancer 60:487.

Robinson et al. (2004) "Improving Monoclonal Antibodies for Cancer Therapy," Drug Development Research, 61:172-187.

Rudnick et al., (2009), Can. Biotherp. & Radiopharm. 24:155-162.

Salfeld (2007), Nature Biotech. 25(12):1369-1372

Seaver et al. (1994), "Monoclonal Antibodies in Industry: More Difficult Than Originally Thought," Genetic Eng. News pp. 10, 21.

Sherley et at (1988), "Human Cytosolic Thymidine Kinase," J. Biol. Chem. 263:375-391.

Stewart, L. H. et al. (1992), "Why do most primary neoplasm first appear around the ureteric orifices?," Journal of Biomedical Sciences 3(1):13-17.

Stewart, L. H. et al. (1993), "Why do most primary bladder neoplasms occur around the ureteric orifices?," British Journal of Urology 71:34-37.

Stites et al. (1991), "Basic and Clinical Immunology," Seventh Edition, p. 584.

Tamiya et al. (1989), "Co-Purification of Thymidylate Kinase and Cytosolic Thymidine Kinase from Human Term Placenta by Affinity Chromatography: Biochem. Biophys. Acta 995:28-35.

Taylor, M. H. et al. (2002), "Radiation induced apoptosis in MOLT-4 cells requires de novo protein synthesis independent of de novo RNA synthesis," FEBS letters 514:119-20.

Thomas, W. M. et al. (1995), "Serum thymidine kinase in colorectal neoplasia," European Journal of Surgical Oncology 21:632-634.

Thurber et al. (2008), (Adv. Drug Deliv. Rev. 60:1421-1434.

Topolcan et at. (2005), "Changes of Thymidine Kinase (TK) During Adjuvant and Palliative Chemotherapy," Anticancer Res. 25:1831-1834.

Voskoglou-Nomikos (2003), Clin. Can. Res. 9:4227-4239.

Willingham et at. (1987), "Pseudomonas Exotoxin Coupled to a Monoclonal Antibody Against Ovarian Cancer Inhibits the Growth of Human Ovarian Cancer Cells in a Mouse Model," Proc. Natl. Acad. Sci. USA 84:2474-2478.

Wu, Chuanjing et al. (2003), "Production and characterization of a novel chicken IgY antibody raised against C-terminal peptide from human thymidine kinase 1," Journal of Immunological Methods, 277(1-2):157-169.

Yagihashi, Atsuhito et al. (2005), "Detection of autoantibodies to survivin and livin in sera from patients with breast cancer," Clinica Chimica Acta 362:125-130.

Zhang, H. (2001), "A Monoclonal Antibody Specific for Human Thymidine Kinase 1," Hybridoma 20(1):25-34.

Zhang, H. et al. (2001), Thymidine Kinase Immunoassay: A potential marker for breast cancer," Cancer Detection and Prevention 25(1):8-15.

Zhang, Jian-Ying et al. (2003), "Enhancement of Antibody Detection in Cancer Using Panel of Recombinant Tumor-associated Antigens," Cancer Epidemiology, Biomarkers & Prevention 12:36-143.

U.S. Patent Publication Nos.:

20030148410, published August, 2003 of Berger et al 20070003990, published January, 2007 of Schlegel et al.

20100143290, published Jun. 10, 2010 of Lallatin 20100143244, published Jun. 10, 2010 of Lallatin U.S. Pat. No. 4,317,877, issued March, 1982 to Balis et al.

U.S. Pat. No. 4,474,893, issued October, 1984 to Reading

U.S. Pat. No. 4,722,899, issued February, 1988 to Hamaoka et al.

U.S. Pat. No. 4,816,567, issued March, 1989 to Cabilly et al.
U.S. Pat. No. 5,476,996, issued December, 1995 to Wilson et al.
U.S. Pat. No. 5,514,548, issued May, 1996 to Krebber et al.
U.S. Pat. No. 5,698,409, issued December, 1997 to O'Neill, K. L.
U.S. Pat. No. 5,869,045, issued February, 1999 to Hellstrom et al.
U.S. Pat. No. 6,083,707, issued July, 2000 to Eriksson et al.
U.S. Pat. No. 6,331,415, issued December, 2001 to Cabilly et al.
U.S. Pat. No. 6,372,217, issued April 2002 to Uckum
U.S. Pat. No. 7,311,906, issued December 2007 to Lallatin et al.
U.S. Pat. No. 7,837,998, issued November 2010 to Lallatin et al.
International Patent Publication Nos.:
WO9306213, published April, 1993 of Hoogenboom et al.
WO9708320, published Mar. 6, 1997 of Knappik et al.
European Patent Nos.:
EP0042482, published Dec. 30, 1981 of Balis et al.
EP0454478, published October, 1991 of Mitsushima et al.
EP0255431, published Oct. 23, 1991 of Jouim

The invention claimed is:

1. A method for diagnosing the presence of cancer in a biological sample from a human with a sandwich ELISA comprising:
   a. coating a surface of well with one or more capture antibodies that bind specifically to human TK1 molecule;
   b. contacting the sample with the surface coated well with the one or more capture antibodies to capture TK1 molecules from the sample on the surface;
   c. contacting the surface having captured TK1 molecules with one or more detection antibodies that bind specifically to human TK1 molecule;
   d. determining the amount of detection antibodies bound, wherein one or both of capture antibodies and detection antibodies comprising antibodies that specifically bind to the target consisting SEQ ID NO. 1 amino-acid sequence on human TK1 molecule, wherein cancer is diagnosed when the amount human TK1 in the sample as measured by the amount of bound detection antibodies are present in a cancer-diagnostic amount, an amount greater than the average range of TK1 in a sample of the same material taken from a normal human that does not have cancer.

---

SEQUENCE LISTING

```
<160> NUMBER OF SEQ ID NOS: 2

<210> SEQ ID NO 1
<211> LENGTH: 100
<212> TYPE: PRT
<213> ORGANISM: Human

<400> SEQUENCE: 1

Gln Tyr Lys Cys Leu Val Ile Lys Tyr Ala Lys Asp Thr Arg Tyr Ser
1               5                   10                  15

Ser Ser Phe Cys Thr His Asp Arg Asn Thr Met Glu Ala Leu Pro Ala
            20                  25                  30

Cys Leu Leu Arg Asp Val Ala Gln Glu Ala Leu Gly Val Ala Val Ile
            35                  40                  45

Gly Ile Asp Glu Gly Gln Phe Phe Pro Asp Ile Val Glu Phe Cys Glu
        50                  55                  60

Ala Met Ala Asn Ala Gly Lys Thr Val Ile Val Ala Ala Leu Asp Gly
65                  70                  75                  80

Thr Phe Gln Arg Lys Pro Phe Gly Ala Ile Leu Asn Leu Val Pro Leu
                85                  90                  95

Ala Glu Ser Val
            100

<210> SEQ ID NO 2
<211> LENGTH: 300
<212> TYPE: DNA
<213> ORGANISM: Human

<400> SEQUENCE: 2
cagtacaagt gcctggtgat caagtatgcc aaagacactc gctacagcag cagcttctgc       60
acacatgacc ggaacaccat ggaggcactg cccgcctgcc tgctccgaga cgtggcccag      120
gaggccctgg gcgtggctgt cataggcatc gacgaggggc agttttttccc tgacatcgtg      180 gagttctgcg aggccatggc caacgccggg aagaccgtaa ttgtggctgc actggatggg      240
accttccaga ggaagccatt tggggccatc ctgaacctgg tgccgctggc cgagagcgtg      300
```

2. An antibody that specifically binds to the target consisting SEQ ID NO. 1 amino-acid sequence on human TK1 molecule.

* * * * *